US008486647B2

(12) United States Patent
Alessandri Haber et al.

(10) Patent No.: US 8,486,647 B2
(45) Date of Patent: Jul. 16, 2013

(54) NEUROPEPTIDE RELEASE ASSAY FOR SODIUM CHANNELS

(75) Inventors: Nicole M. Alessandri Haber, Rye, NY (US); Lynn Macdonald, White Plains, NY (US); Michael L. LaCroix-Fralish, Sleepy Hollow, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 25 days.

(21) Appl. No.: 13/236,117

(22) Filed: Sep. 19, 2011

(65) Prior Publication Data

US 2012/0083000 A1    Apr. 5, 2012

Related U.S. Application Data

(63) Continuation-in-part of application No. 13/155,491, filed on Jun. 8, 2011.

(60) Provisional application No. 61/485,488, filed on May 12, 2011, provisional application No. 61/352,920, filed on Jun. 9, 2010.

(51) Int. Cl.
    *C07K 14/705* (2006.01)
    *C07K 19/00* (2006.01)
    *C12N 15/62* (2006.01)
    *G01N 33/567* (2006.01)

(52) U.S. Cl.
    USPC ......... 435/7.21; 435/69.7; 436/501; 536/23.4

(58) Field of Classification Search
    None
    See application file for complete search history.

(56) References Cited

U.S. PATENT DOCUMENTS

| 7,195,879 B2 | 3/2007 | Dubin et al. |
| 7,423,121 B2 | 9/2008 | Korsgaard |
| 7,615,569 B2 | 11/2009 | Fulp et al. |
| 7,670,771 B2 | 3/2010 | Leppert et al. |
| 7,705,158 B2 | 4/2010 | Wang et al. |
| 7,754,440 B2 | 7/2010 | Adorante et al. |
| 2009/0298095 A1 | 12/2009 | Hoke et al. |
| 2010/0297674 A1 | 11/2010 | Shekdar |
| 2010/0323359 A1 | 12/2010 | Macdonald et al. |
| 2011/0016541 A1 | 1/2011 | Weinstein et al. |
| 2011/0306654 A1 | 12/2011 | Macdonald et al. |
| 2011/0312533 A1 | 12/2011 | Shekdar et al. |

FOREIGN PATENT DOCUMENTS

| WO | 2007109324 A2 | 9/2007 |
| WO | 2010022055 A2 | 2/2010 |
| WO | 2010087864 A1 | 8/2010 |
| WO | 2011022634 A2 | 2/2011 |
| WO | 2011032112 A2 | 3/2011 |
| WO | 2012099983 A1 | 7/2012 |

OTHER PUBLICATIONS

Wood, JN et al. 1990. Novel cell lines display properties of nociceptive sensory neurons. Proc. R. Soc. Lond. 241:187-194.

Dugandzija-Novakovic, S. et al. 1995. Clustering of Na+ Channels and Node of Ranvier Formation in Remyelinating Axons. J. Neurosci. 15(1):492-503.

Klugbauer, N. et al. 1995. Structure and functional expression of a new member of the tetrodotoxin-sensitive voltage-activated sodium channel family from human neuroendocrine cells. EMBO J. 14(6):1084-1090.

Sah, Dwy et al. 1997. Biopotent progenitor cell lines from the human CNS. Nature Biotech. 15:574-580.

Toledo-Aral, JJ et al. 1997. Identification of PN1, a predominant voltage-dependent sodium channel expressed principally in peripheral neurons. PNAS 94:1527-1532.

Catterall, WA 2000. From Ionic Currents to Molecular Mechanisms: The Structure and Function of Voltage-Gated Sodium Channels. Neuron 26:13-25.

Goldin, AL et al. 2000. Nomenclature of Voltage-Gated Sodium Channels. Neuron (Letter to the Editor) 28:365-368.

Goldin, AL 2001. Resurgence of Sodium Channel Research, Annu. Rev. Physiol. 63:871-894.

Catterall, WA et al. 2003. International Union of Pharmacology. XXXIX. Compendium of Voltage-Gated Ion Channels: Sodium Channels. Pharmacol. Rev. 55:575-578.

Yu, FH and WA Catterall. 2003. Overview of the voltage-gated sodium channel family. Genome Biol. 4:2076.1-207.7.

Nassar, MA et al. 2004. Nocicpetor-specific gene deletion reveals a major role for Nav1 7 (PN1) in acute and inflammatory pain. PNAS 101(34):12706-12711.

Wood, JN et al. 2004. Voltage-Gated Sodium Channels and Pain Pathways. J Neurobiol 61(1):55-71.

Catterall, WA et al. 2005. International Union of Pharmacology. XLVII. Nomenclature and Structure-Function Relationships of Voltage-Gated Sodium Channels. Pharmacol. Rev. 57:379-409.

Mechaly, I et al. 2005. Molecular diversity of voltage-gated sodium channel alpha subunits expressed in neuronal and non-neuronal excitable cells. Neurosci 130:389-396.

Nassar, MA at al, 2005. Neuropathic pain develops normally in mice lacking both Nav1.7 adn Nav1.8. Molecular Pain I:24, 9 pages.

(Continued)

*Primary Examiner* — John Ulm
(74) *Attorney, Agent, or Firm* — Veronica Mallon; Veleta Gregg

(57) ABSTRACT

Methods and compositions for using genetically modified non-human animals are provided, wherein the genetic modification comprises a humanization of the one or more extracellular pore loops of a $Na_V1.7$ channel protein or a complete humanization of an endogenous $Na_V1.7$ gene. Methods for using isolated DRG cultures from genetically modified non-human animals are also provided, wherein the isolated DRG express a human or chimeric $Na_V1.7$ protein on the surface, in particular measuring primary nociceptive activation through the release of calcitonin gene-related peptide (CGRP) in isolated DRG in vitro, and wherein the isolated DRG cultures are capable of generating action potentials and communicating through an excitable signal via the expressed human or chimeric $Na_V1.7$ protein the cell surface. In vivo and in vitro methods for characterizing $Na_V1.7$-specific antagonists and evaluation of corresponding therapeutic potential for $Na_V1.7$-mediated disease are also provided.

27 Claims, 15 Drawing Sheets

OTHER PUBLICATIONS

Stirling, LC et al. 2005. Nociceptor-specific gene deletion using heterozygous Nav1.8-Cre recombinase mice. Pain 113:27-36.

Yeomans, DC et al. 2005. Decrese in Inflammatory Hyperalgesia by Herpes Vector-mediated Knockdown of Nav1.7 Sodium Channels in Primary Afferents. Human Gene Therapy 16:271-277.

Cox, JJ et al. 2006. An SCN9A channelopathy causes congenital inability to experience pain. Nature 444 (7121):894-898.

Rogers, M et al. 2006. The role of sodium channels in neuropathic pain. Seminars in Cell & Developmental Biology 17:571-581.

Catterall, WA et al. 2007. Voltage-gated ion channels and gating modifier toxins. Toxicon 49:124-141.

Chen, W et al. 2007. Immortilization and characterization of a nociceptive dorsal root ganglion sensory neuronal line. J Pheripheral Nervous System 12:121-130.

Dib-Hajj, SD et al. 2007. From genes to pain: Nav1.7 and human pain disorders. Trends in Neurosci 30 (11):555-563.

Goldberg, YP et al. 2007. Loss-of-function mutations in the Nav1.7 gene underlie congenital indifference to pain in multiple human populations. Clin Genet 71:311-319.

Harvey, VL and AH Dickenson. 2008. Mechanisms of pain in non-malignant disease. Current Opinion in Supportive and Palliative Care 2:133-139.

Dib-Hajj, SD et al. 2009. Voltage-Gated Sodium Channels: Therapeutic Targets for Pain. Pain Medicine 10 (7):1260-1269.

Nilsen, KB et al. 2009. Two novel SCN9A mutations causing insensitivity to pain. Pain 143:155-158.

Priest, BT 2009. Future potential and status of selective sodium channel blockers for the treatment of pain. Current Opinion in Drug Discovery & Development 12(5):682-692.

Clare, JJ 2010. Targeting voltage-gated sodium channels for pain therapy. Expert Opin Investig Drugs 19(1):45-62.

Dib-Hajj, SD et al. 2010. Sodium Channels in Normal and Pathological Pain. Annu Rev Neurosci 33:325-347.

Fischer, TZ and SG Waxman 2010. Familial pain syndromes from mutations of the Nav1.7 sodium channel. Ann NY Acad Sci 1184:196-207.

Lampert, A et al. 2010. Sodium channelopathies and pain. Pflugers Arch 460(2)249-263.

Oku, R., M. Satoh, N. Fujii, A. Otaka, H. Yajima, and H. Takagi. (1987) Calcitonin gene-related peptide promotes mechanical nociception by potentiating release of substance P from the spinal dorsal horn in rats. Brian Research 403:350-354.

Lou, Y.P., A. Franco-Cereceda, and J. M. Lundberg. (1992) Different Ion channel mechanisms between low concentrations of capsaicin and high concentrations of capsaicin and nicotine regarding peptide release from pulmonary afferents. Acta Physiol. Stand. 146:119-127.

Lundberg, J.M., A. Franco-Cereceda, K. Alving, P. Delay-Goyet, and Y. Lou. (1992) Release of calcitonin-gene related peptide from sensory neurons. Annals of the New York Academy of Sciences 657:187-193.

Poyner, D.R. (1992) Calcitonin gene-related peptide: multiple actions, multiple receptors. Pharmac. Ther. 56:23-51.

Nicol, G.D. and M. Cui. (1994) Enhancement by prostaglandin E2 of bradykinin activation of embryonic rat sensory neurons. Journal of Physiology 480(Pt 3):485-492.

Vasko, M.R., W.B. Campbell, and K. J. Waite. (1994) Prostaglandin E2 enhances bradykinin-stimulated release of neuropeptides from rat sensory neurons in culture. Journal of Neuroscience 14(8): 4987-4997.

Noda, K., Y. Ueda, K. Suzuki, and K. Yoda. (1997) Excitatory effects of algesic compounds on neuronal processes in murine dorsal root ganglion cell culture. Brain Research 751:348-351.

Ai, X., S.E. MacPhedran, and A.K. Hall. (1998) Depolarization stimulates initial calcitonin gene-related peptide expression by embryonic sensory neurons in vitro. Journal of Neuroscience 18(22):9294-9302.

Averbeck, B., I. Izydorczyk, and M. Kress. (2000) Inflammatory mediators release calcitonin gene-related peptide from dorsal root ganglion neurons of the rat. Neuroscience 98(1)135-140.

Salmon, A., M. Imad Damaj, L. M. Marubio, M.P. Epping-Jordan, E. Merlo-Pich, and J. Changeux. (2001) Altered neuroadaptation in opiate dependence and neurogenic inflammatory nociception in alpha CGRP-deficient mice. Nature 4(4):357-358.

Southall, M.D. and M.R. Vasko. (2001) Prostaglandin receptor subtypes, EP3C and EP4, mediate the prostaglandin E2-induced cAMP production and sensitization of sensory neurons. Journal of Biological Chemistry 276 (19):16083-16091.

Strecker, T., K. Messlinger, M. Weyand, P.W. Reeh. (2005) Role of different proton-sensitive channels in releasing calcitonin gene-related peptide from isolated hearts of mutant mice. Cardiovascular Research 65:405-410.

Ruparel, N.B., A.M. Patwardhan, A.N. Akopian, and K.M. Hargreaves. (2008) Homologous and heterologous desensitization of capsaicin and mustard oil responses utilize different cellular pathways in nociceptors. Pain 135:271-279.

Spitzer, M.J.S., P.W. Reeh, and S.K. Sauer. (2008) Mechanisms of potassium- and capsaicin-induced axonal calcitonin gene-related peptide release: involvement of L- and T-type calcium channels and TRPV1 but not sodium channels. Neuroscience 151:836-842.

Yue, X., S. Tumait, E. Navratilova, D. Strop, P.A. St John, T.W. Vanderah, W.R. Roeske, H.I. Yamamura, and E.V. Varga. (2008) Sustained morphine treatment augments basal CGRP release from cultured primary sensory neurons in a Raf-1 dependent manner. European Journal of Pharmacology 584:272-277.

Momin, A. and P.A. McNaughton. (2009) Regulation of firing frequency in nociceptive neurons by pro-inflammatory mediators. Exp. Brain Res. 196:45-52.

Schmutzler, B.S., S. Roy, and C.M. Hingtgen. (2009) Glial cell line-derived neurotrophic factor family ligands enhance capsaicin-stimulated release of calcitonin gene-related peptide from sensory neurons. Neuroscience 161:148-156.

Tumati, S., H.I. Yamamura, T.W. Vanderah, W.R. Roeske, and E.V. Varga. (2009) Sustained morphine treatment augments capsaicin-induced calcitonin gene-related peptide release from primary sensory neurons in a protein kinase A- and Raf-1-dependent manner. Journal of Pharmacology and Experimental Therapeutics 330(3):810-817.

Tumati, S., W.R. Roeske, T.W. Vanderah, and E.V. Varga. (2010) Sustained morphine treatment augments prostaglandin E2-evoked calcitonin gene-related peptide release from primary sensory neurons in a PKA-dependent manner. European Journal of Pharmacology 648:95-101.

Schmutzler, B.S., S. Roy, S.K. Pittman, R.M. Meadows, and C.M. Hingtgen. (2011) Ret-dependent and Ret-independent mechanisms of Gfl-induced sensitization. Molecular Pain 7:1-22.

Supowit, S.C., H. Zhao, K.A. Katki, P. Gupta, and D.J. DiPette. (2011) Bradykinin and prostaglandin E1 regulate calcitonin gene-related peptide expression in cultured rat sensory neurons. Regulatory Peptides 167:105-111.

NEUROPEPTIDE RELEASE ASSAY FOR SODIUM CHANNELS

This application is a continuation-in-part of U.S. Ser. No. 13/155,491 filed 8 Jun. 2011, which claims benefit under 35 USC §119(e) of U.S. Provisional Patent Application Ser. No. 61/485,488, filed 12 May 2011, and of U.S. Provisional Patent Application Ser. No. 61/352,920, filed 9 Jun. 2010; this application also claims benefit under 35 USC §119(e) of U.S. Provisional Patent Application 61/485,488 filed 12 May 2011; each application of which is herein specifically incorporated by reference in its entirety.

FIELD OF INVENTION

Genetically modified non-human animals are provided that express human voltage-gated sodium ($Na_V$) channels or fragments thereof, in particular $Na_V1.7$ (Scn9A). Genetically modified mice useful for the identification and testing of antagonists for treating chronic pain states or disorders associated with aberrant $Na_V1.7$ activity and/or function are provided. Methods for making genetically modified non-human animals that express human $Na_V1.7$ protein, and, alternatively, that express a partially human $Na_V1.7$ protein, are provided. Non-human animals are provided that do not express an endogenous $Na_V1.7$ protein.

BACKGROUND

Sodium channels are integral membrane proteins that form ion channels in the plasma membrane of excitable cells. They are classified as voltage-gated sodium ($Na_V$) channels, which permit the influx of $Na^+$ ions that mediate action potentials in excitable cells; and ligand-gated sodium channels, which bind a ligand that triggers the influx of ions leading to similar action potentials.

$Na_V$ channels, like calcium and potassium channels, are composed of a very large and complex α-subunit on the surface of the cell which includes four domains (DI-DIV), each with six transmembrane α-helix segments (S1-S6) and including a pore that allows the influx of $Na^+$ ions into the cell (FIG. 1; see also Clare 2010 Expert Opin. Investig. Drugs 19(1): 45-62). For $Na_V$ channels, a single gene encodes all of these domains. Transmembrane segment 4 (S4) within each domain of $Na_V$ channels contains positively charged amino acids (FIG. 1) that act as a voltage sensor. The intracellular loop that connects Domains III and IV contains sequences that are reportedly involved in inactivation. $Na_V$ channels interact with other proteins on the cell surface termed β-subunits, which are involved in channel kinetics and voltage-dependent gating functions. $Na_V$ channels reportedly exhibit diverse functional properties and distinct expression patterns, which imply specialized functions among the channels and predisposes some for roles in transmitting specific signals, for example, pain signals.

In spite of many efforts to elucidate the properties and functions of human $Na_V$ channels, the large size and complex nature of their structure makes it difficult to study the global aspects of their biological activity and their involvement in the pain response. This difficulty is increased by the fact that global deletion is lethal; Scn9A$^{-/-}$ pups die shortly after birth, apparently due to a failure to feed. Therefore, there is a need in the art for compositions and methods that supplement and enhance current in vitro systems (for example, in vitro-transfected cells containing constructs expressing human $Na_V$ channels in culture) by employing more biologically sensible approaches to making non-human animals and cells that include whole human $Na_V$ channels or chimeric $Na_V$ channels containing specific human fragments associated with $Na_V$ channel activation and that can function in facilitating the pain response.

SUMMARY OF INVENTION

Genetically engineered non-human animals, tissues, and cells are provided that express a human $Na_V$ α-subunit, or a functional fragment thereof, on the surface of a cell. In various embodiments, the $Na_V$ α-subunit is a $Na_V1.7$ α-subunit.

In one aspect, genetically engineered non-human animals are provided that express a $Na_V1.7$ α-subunit on the surface of a cell provide an in vivo system to identify antagonists of the channel, and to identify therapeutic agents for the treatment of pain disorders or syndromes, such as, for example, chronic pain, erythromelalgia (IEM) and paroxysmal extreme pain disorder (PEPD).

In one aspect, genetically engineered non-human animals are provided that express a $Na_V1.7$ α-subunit on the surface of a cell and provide a system to selectively test efficacy and toxicity of a therapeutic on mutant or variant forms of human $Na_V1.7$. In one embodiment, the therapeutic agent is a compound that functions as a sodium channel blocker. In a specific embodiment, the compound is a synthetic compound. In one embodiment, the synthetic compound is selected from lidocaine, mexiletine, carbamazepine, amitryptiline and biphenyl pyrazoles, or a combination thereof. In another embodiment, compound is a toxin. In a specific embodiment, the toxin is selected from tetrodotoxin and neosaxitosin or a combination thereof.

In one embodiment, genetically engineered non-human animals are provided that express a $Na_V1.7$ α-subunit on the surface of a cell and provide a system to selectively test functionality (e.g., efficacy) and/or toxicity of combinations of therapeutic agents on mutant or variant forms of a human $Na_V1.7$. In one embodiment, the combination of therapeutic agents comprises provide a synergistic effect upon administration to the genetically engineered non-human animal. In a specific embodiment, the combination of therapeutic agents comprises at least two of a synthetic compound, a naturally occurring toxin, or a protein (e.g., an anti-$Na_V$ antibody).

In one aspect, genetically engineered mice are provided that express a human $Na_V$ channel protein, specifically a human $Na_V1.7$ α-subunit. The mice are genetically engineered to include all or substantially all of a human $Na_V1.7$ gene.

In one embodiment, the human $Na_V1.7$ gene replaces an endogenous mouse $Na_V1.7$ gene at the endogenous mouse $Na_V1.7$ locus.

In one aspect, genetically engineered mice are provided that express a chimeric $Na_V1.7$ α-subunit, wherein the mice include a mouse $Na_V1.7$ α-subunit engineered with one or more extracellular pore loops containing a corresponding sequence from a human $Na_V1.7$ gene.

In one embodiment, the chimeric $Na_V1.7$ α-subunit comprises an extracellular pore loop connecting transmembrane segments 5 and 6 of Domain I that comprises the corresponding sequence from the human $Na_V1.7$ gene. In another embodiment, the chimeric $Na_V1.7$ α-subunit comprises an extracellular pore loop connecting transmembrane segments 5 and 6 of Domain III that comprises the corresponding sequence from the human $Na_V1.7$ gene.

In one aspect, a genetically engineered mouse is provided that comprises substantially all of the human genomic DNA that encodes a $Na_V1.7$ protein. In another aspect, the genetically modified mouse comprises a portion of human genomic DNA, and the mouse expresses a chimeric $Na_V1.7$ protein.

In one embodiment, the portion of human genomic DNA comprises human sequence that encodes the extracellular pore loop connecting transmembrane segments 5 and 6 of Domain I of the human $Na_V1.7$ gene. In another embodiment, the portion of human genomic DNA comprises human sequence that encodes the extracellular pore loop connecting transmembrane segments 5 and 6 of Domain III of the human $Na_V1.7$ gene.

In one aspect, a genetically engineered mouse is provided that is capable of expressing a human or a chimeric $Na_V1.7$ protein on the surface of a cell of the mouse.

In one embodiment, the $Na_V1.7$ is chimeric and comprises a human extracellular pore loop. In a specific embodiment, the human extracellular pore loop is the loop connecting transmembrane segments 5 and 6 of Domain I. In another specific embodiment, the human extracellular pore loop is the loop connecting transmembrane segments 5 and 6 of Domain III.

In one embodiment, the cell is an excitable cell. In another embodiment the cell is a non-excitable cell. In a specific embodiment, the cell is a neuron. In a specific embodiment, the cell is a dorsal root ganglion (DRG) neuron. In another specific embodiment, the cell is a sympathetic ganglion neuron.

In one embodiment, the human or chimeric $Na_V1.7$ gene is operably linked to a human or mouse leader sequence. In one embodiment, the leader sequence is a mouse leader sequence.

In one embodiment, the human or chimeric $Na_V1.7$ gene is operably linked to a human or mouse promoter. In a specific embodiment, the promoter is an endogenous mouse $Na_V1.7$ gene promoter.

In one embodiment, the genetically modified mouse comprises a human $Na_V1.7$ gene locus that encodes a human $Na_V1.7$ protein. In another embodiment, the genetically modified mouse comprises a chimeric $Na_V1.7$ gene locus that comprises a human sequence that encodes an extracellular pore loop that is substantially human. In a specific embodiment, the human sequence encodes an extracellular pore loop connecting transmembrane segments 5 and 6 of Domain I of the chimeric $Na_V1.7$ protein. In another specific embodiment, the human sequence encodes an extracellular pore loop connecting transmembrane segments 5 and 6 of Domain III of the chimeric $Na_V1.7$ protein.

In one embodiment, the $Na_V1.7$ gene locus comprises a human genomic fragment comprising about 113 kb of DNA that encodes a human $Na_V1.7$ protein. In a specific embodiment, the $Na_V1.7$ gene locus comprises exons 2 to 28 of a human $Na_V1.7$ gene.

In another embodiment, the $Na_V1.7$ gene locus comprises a nucleic acid sequence of a human $Na_V1.7$ gene locus comprising about 10 kb of DNA that encodes an extracellular pore loop of a human $Na_V1.7$ protein. In a specific embodiment, the nucleic acid sequence comprises exons 7 to 9 of a human $Na_V1.7$ gene. In specific embodiment, the extracellular pore loop is the loop connecting transmembrane segments 5 and 6 of Domain I of a human $Na_V1.7$ protein.

In another embodiment, the $Na_V1.7$ gene locus comprises a human genomic nucleic acid sequence comprising about 2.8 kb of DNA that encodes an extracellular pore loop of a human $Na_V1.7$ protein. In a specific embodiment, the human genomic nucleic acid sequence comprises exons 23 to 25 of a human $Na_V1.7$ gene. In a specific embodiment, the extracellular pore loop is the loop connecting transmembrane segments 5 and 6 of Domain III of a human $Na_V1.7$ protein.

In one embodiment, the genetically modified mouse is capable of expressing a fully human $Na_V1.7$ protein. In another embodiment, the genetically modified mouse is capable of expressing a partially human $Na_V1.7$ protein. In a specific embodiment, the genetically modified mouse is capable of expressing a chimeric $Na_V1.7$ protein comprising an extracellular sequence from a human $Na_V1.7$ protein.

In one embodiment, the partially human $Na_V1.7$ protein comprises an extracellular pore loop that contains a human sequence. In a specific embodiment, the extracellular pore loop is selected from the group consisting of the loop connecting transmembrane segments 5 and 6 of Domain I, and the loop connecting transmembrane segments 5 and 6 of Domain III. In a specific embodiment, the human extracellular pore loop is the loop connecting transmembrane segments 5 and 6 of Domain I. In another embodiment, the human extracellular pore loop is the loop connecting transmembrane segments 5 and 6 of Domain III.

In one embodiment, the mouse comprises a cell that expresses a human $Na_V1.7$ protein. In another embodiment, the mouse comprises a cell that expresses a chimeric $Na_V1.7$ protein that comprises one or more human extracellular pore loops. In a specific embodiment, the human extracellular pore loops are selected from the group consisting of the loop connecting transmembrane segments 5 and 6 of Domain I, the loop connecting transmembrane segments 5 and 6 of Domain III, and a combination thereof. In a specific embodiment, the human extracellular pore loop is the loop connecting transmembrane segments 5 and 6 of Domain I. In another embodiment, the human extracellular pore loop is the loop connecting transmembrane segments 5 and 6 of Domain III. In one embodiment, the cell is an excitable cell. In another embodiment the cell is a non-excitable cell. In a specific embodiment, the cell is a neuron. In a specific embodiment, the neuron is a DRG neuron. In another specific embodiment, the neuron is a sympathetic ganglion neuron.

In one embodiment, the mouse comprises a combination of one or more embodiments and/or aspects described in this disclosure.

In one embodiment, the genetically modified mouse is a C57BL strain, in a specific embodiment selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola. In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain.

In one aspect, a mouse cell is provided that is isolated from a mouse as described herein. In one embodiment, the cell is an ES cell. In one embodiment, the cell is an excitable cell. In another embodiment, the cell is a non-excitable cell. In one embodiment, the cell is a neuron. In a specific embodiment, the neuron is a DRG neuron. In another specific embodiment, the neuron is a sympathetic ganglion neuron.

In one aspect, a cell is provided; wherein the cell bears a $Na_V1.7$ protein that comprises a human sequence corresponding to an extracellular pore loop of the $Na_V1.7$ channel protein.

In one embodiment, the cell is a neuronal cell. In a specific embodiment, the cell is selected from a dorsal root ganglion (DRG) cell, a trigeminal ganglion cell and a sympathetic ganglion neuron. In a specific embodiment, the cell is a DRG cell that expresses a $Na_V1.7$ protein that comprises a human loop selected from the loop connecting transmembrane segments 5 and 6 of Domain I, the loop connecting transmembrane segments 5 and 6 of Domain II, the loop connecting transmembrane segments 5 and 6 of Domain III, the loop connecting transmembrane segments 5 and 6 of Domain IV, and a combination thereof. In one embodiment, the human loop is the loop connecting transmembrane segments 5 and 6 of Domain I. In one embodiment, the human loop is the loop connecting transmembrane segments 5 and 6 of Domain III.

In one embodiment, the cell is immortalized.

In one aspect, a mouse embryo is provided, wherein the embryo comprises a donor ES cell that is derived from a mouse as described herein.

In one aspect, a targeting vector is provided, comprising a human genomic nucleic acid sequence containing a human $Na_V1.7$ gene or a fragment thereof and a selection cassette. In one aspect, a targeting vector is provided, comprising a ~113 kb human genomic nucleic acid sequence comprising exons 2 to 28 of a human $Na_V1.7$ gene and a hygromycin cassette. In another aspect, a targeting vector is provided, comprising a ~10 kb human genomic nucleic acid sequence comprising exons 7 to 9 of a human $Na_V1.7$ gene and a neomycin cassette. In another aspect, a targeting vector is provided, comprising a ~2.8 kb human genomic nucleic acid sequence comprising exons 23 to 25 of a human $Na_V1.7$ gene and a neomycin cassette.

In one aspect, a $Na_V1.7$ protein made by a mouse as described herein is provided, wherein the $Na_V1.7$ protein comprises a human sequence encoded by a fragment of a human $Na_V1.7$ gene selected from the group consisting of exons 2 to 28, exons 7 to 9, and exons 23 to 25 of a human $Na_V1.7$ gene. In one aspect, the fragment of the human $Na_V1.7$ gene is exons 2 to 28. In another aspect, the fragment of the human $Na_V1.7$ gene is exons 7 to 9. In another aspect, the human fragment of the human $Na_V1.7$ gene is exons 23 to 25.

In one embodiment, the $Na_V1.7$ protein is reconstituted in a vesicle. In one embodiment, the $Na_V1.7$ is present in a vesicle preparation from a mouse as described herein.

In one aspect, a method for making a mouse that expresses a fully or partially humanized $Na_V1.7$ protein on a surface of an excitable cell, is provided, comprising (a) genetically modifying a mouse ES cell by replacing one or more $Na_V1.7$ mouse DNA sequences with one or more human $Na_V1.7$ DNA sequences to form a mouse donor ES cell; (b) introducing the mouse donor ES cell into a host mouse embryo to form a modified embryo; (c) gestating the modified embryo in a suitable mouse; and, (d) obtaining a mouse pup that expresses the fully or partly humanized $Na_V1.7$ protein on the surface of an excitable cell of the mouse pup.

In one embodiment, the one or more human $Na_V1.7$ DNA sequences are selected from exons 2 to 28 of a human $Na_V1.7$ gene, exons 7 to 9 of a human $Na_V1.7$ gene and exons 23 to 25 of a human $Na_V1.7$ gene.

In one embodiment, the one or more human $Na_V1.7$ DNA sequences is all or substantially all of a human $Na_v1.7$ DNA sequence. In a specific embodiment, the sequence is exons 2 to 28 of a human $Na_V1.7$ gene. In another specific embodiment, the sequence is exons 7 to 9 of a human $Na_V1.7$ gene. In another specific embodiment, the sequence is exons 23 to 25 of a human $Na_V1.7$ gene.

In one aspect, a mouse is provided that expresses a human $Na_V1.7$ α-subunit from an endogenous mouse $Na_V1.7$ locus, wherein the mouse expresses an endogenous mouse $Na_V$ β-subunit, and wherein the mouse expresses an endogenous $Na_V$ protein selected from the group consisting of $Na_V1.6$, $Na_V1.8$, and $Na_V1.9$.

In one embodiment, the human $Na_V1.7$ α-subunit is a variant $Na_V1.7$ α-subunit, wherein the variant comprises an amino acid substitution that comprises a Q10R, I136V, F216S, S241T, N395K, V400M, L823R, I848T, L858H, L858F, A863P, V872G, F1449V, or a combination thereof.

In one embodiment, the human $Na_V1.7$ α-subunit is a variant $Na_V1.7$ α-subunit, wherein the variant comprises an amino acid substitution that comprises a R996C, V1298D, V1298F, V1299F, I1461T, F1462V, T1464I, M1627K, A1632E, or a combination thereof.

In one embodiment, the human $Na_V1.7$ α-subunit is a variant $Na_V1.7$ α-subunit, wherein the variant comprises an amino acid substitution that comprises a F1200L, I1235L, or a combination thereof.

In one embodiment, the human $Na_V1.7$ α-subunit is a truncated $Na_V1.7$ α-subunit, wherein the truncated $Na_V1.7$ α-subunit protein ends at an amino acid residue selected from 259, 277, 328, 459, 693, 767, 830, 897, 1488, 1659 and 1689. In a specific embodiment, the truncated $Na_V1.7$ α-subunit protein ends at amino acid residue 693. In another specific embodiment, the truncated $Na_V1.7$ α-subunit protein ends at amino acid residue 1488.

In one aspect, a method is provided for making a cell line from a cell that expresses a human $Na_V1.7$ sequence, comprising obtaining a cell that expresses a human $Na_V1.7$ sequence from a mouse as described herein, isolating and cloning the cell, and maintaining the isolated and cloned cell in culture. In one embodiment, the method further comprises immortalizing the cell. In one embodiment, the cell is a neuronal cell, e.g., a dorsal root ganglion (DRG) neuron.

In one aspect, a method for making an immortalized cell line from an isolated cell of a mouse as described herein is provided, comprising providing an isolated cell that expresses a human, chimeric or variant human $Na_V1.7$ channel, transfecting the isolated cell with a vector that encodes an oncogene and a selectable marker (e.g., neomycin), growing cells in culture under selection to allow for expansion of cells that have been transfected with the retroviral vector, selecting a transfected cell from the culture containing the vector, isolating cells containing the vector by trypsinization and limiting dilution of the transfected cell in culture, and creating a clonal cell line from the isolated clone that has survived selection by passage into a new culture.

In one embodiment, the isolated cell is a neuron. In one embodiment, the isolated cell is a DRG neuron.

In one embodiment, the human $Na_V1.7$ channel is encoded by exons 2-28 of a human $Na_V1.7$ gene. In another embodiment, the chimeric $Na_V1.7$ channel is encoded by a genomic sequence that comprises a sequence from a human $Na_V1.7$ gene that encodes an extracellular sequence from a human $Na_V1.7$ gene.

In one embodiment, the extracellular sequence encodes a pore loop sequence. In a specific embodiment, the pore loop sequence is selected from a loop connecting transmembrane segments 5 and 6 of Domain I and a loop connecting transmembrane segments 5 and 6 of Domain III. In a specific embodiment, the pore loop is the loop connecting transmembrane segments 5 and 6 of Domain I. In another embodiment, the pore loop is the loop connecting transmembrane segments 5 and 6 of Domain III.

In one aspect, a method for identifying an antagonist of a human $Na_V1.7$ protein is provided, comprising exposing a mouse as described herein to a suspected antagonist of human $Na_V1.7$, and determining an effect of the antagonist on $Na_V1.7$ function in the mouse.

In one embodiment, determining the effect of the antagonist comprises measuring the presence or absence of an action potential upon stimulation of a cell comprising the human $Na_V1.7$.

In one embodiment, the antagonist is specific for $Na_V1.7$ and does not exhibit antagonist activity with respect to $Na_V1.6$, $Na_V1.8$, and $Na_V1.9$.

In one aspect, a method is provided for determining binding activity of a therapeutic agent that binds a human $Na_V1.7$ sequence, comprising contacting the therapeutic agent to a cell that expresses a human $Na_V1.7$ sequence, and determining whether the therapeutic agent binds to the human $Na_V1.7$ sequence. In one embodiment, the cell is derived from a mouse as described herein.

In one embodiment, the cell is a neuronal cell. In a specific embodiment, the cell is selected from a dorsal root ganglion (DRG) cell, a trigeminal ganglion cell and a sympathetic ganglion neuron. In a specific embodiment, the cell is a DRG cell that expresses a $Na_V1.7$ protein that comprises a human loop selected from the loop connecting transmembrane segments 5 and 6 of Domain I, the loop connecting transmembrane segments 5 and 6 of Domain II, the loop connecting transmembrane segments 5 and 6 of Domain III, the loop connecting transmembrane segments 5 and 6 of Domain IV, and a combination thereof. In one embodiment, the human loop is the loop connecting transmembrane segments 5 and 6 of Domain I. In one embodiment, the human loop is the loop connecting transmembrane segments 5 and 6 of Domain III.

In one embodiment, the cell is immortalized.

In one embodiment, the therapeutic agent binds a human $Na_V1.7$ but does not bind a $Na_V1.7$ sequence selected from a mouse, rat, monkey, and a combination thereof.

In one embodiment, the therapeutic agent that binds the human $Na_V1.7$ sequence is selected from a benzodiazepine, a benzazepinone, a tetrodotoxin, a biphenyl pyrazole dicarboxamide, a sodium channel blocker (e.g., amitryptiline, mexiletine, lidocaine, carbamazepine, biphenyl pyrazoles), a piperidine T-type antagonist (e.g., Z123212), and analogs thereof.

In one embodiment, the therapeutic agent that binds the human $Na_V1.7$ sequence is selected from a binding protein that comprises an immunoglobulin $V_H$ and/or $V_L$ or $Na_V1.7$-binding fragment thereof, an antibody, a bispecific antibody, an immunoadhesin, a ligandbody, a peptibody, and a domain antibody (e.g. dAb). In a specific embodiment, the therapeutic agent comprises a human immunoglobulin or T cell receptor variable region. In a specific embodiment, the therapeutic agent is a human antibody.

In one aspect, an in vitro system for identifying an antagonist of a human $Na_V1.7$ protein is provided, comprising isolating a $Na_V1.7$-containing component from a mouse as described herein, exposing the component to a suspected antagonist of human $Na_V1.7$, and determining an effect of the antagonist on $Na_V1.7$ function. In one embodiment, the $Na_V1.7$-containing component is a membrane fraction. In one embodiment, the $Na_V1.7$-containing component is a cell. In one embodiment, the $Na_V1.7$-containing component is a tissue of the mouse.

In one embodiment, determining the effect comprises measuring the presence or absence of a $Na_V1.7$-dependent response in a cell derived from a mouse as described in this disclosure. In one embodiment, the response is an action potential.

In one aspect, a method for the identification of a modulator of a human, chimeric or variant $Na_V1.7$ channel is provided, comprising exposing a mouse as described herein to a test compound and detecting activity or inactivity of the $Na_V1.7$ channel. In one embodiment, the method comprises assaying test compounds that modulate sodium ion flux of the $Na_V1.7$ channel. In another embodiment, the method comprises employing patch clamp technology. In a specific embodiment, the method is used to identify physiologically active compounds useful for treatment of a disease condition of the brain. In one embodiment, the disease condition of the brain is selected from convulsions, seizures, panic disorders, hyperactivity disorders, depression, obsessive compulsive disorders, dementia, memory deficits, attention deficit, obesity, anxiety, eating disorders, drug addiction and misuse, altered sexual drive, Parkinson's disease and Alzheimer's disease. In another embodiment, the disease condition is related to a visceral response originating to the limbic system. In one embodiment, the visceral response is selected from respiration and gastrointestinal function.

In one embodiment, the modulator increases the activity of the $Na_V1.7$ channel. In another embodiment, the modulator decreases the activity of the $Na_V1.7$ channel.

In one embodiment, the human, chimeric or variant human $Na_V1.7$ channel is associated with a pain disorder. In a specific embodiment, the pain disorder is selected from congenital insensitivity to pain (CIP), erythromelalgia (IEM), and paroxysmal extreme pain disorder (PEPD).

In one aspect, a method for determining the probability of disease resulting from a variant $Na_V1.7$ channel is provided, comprising identifying mutations at one or more sites within a nucleic acid sequence of a $Na_V1.7$ gene isolated from a cell of a mouse as described herein that encodes an intracellular N-terminal region, an extracellular loop in domain I, an intracellular loop between domains I and II, an intracellular loop between domains II and III, an intramembrane region of domain II, or any combination thereof, wherein the identified mutations encode a $Na_V1.7$ channel protein that displays a change in function not observed in a nonvariant $Na_V1.7$ channel.

In one embodiment, the human, chimeric or variant human $Na_V1.7$ channel is associated with a pain disorder. In a specific embodiment, the pain disorder is selected from congenital insensitivity to pain (CIP), erythromelalgia (IEM), and paroxysmal extreme pain disorder (PEPD).

In one aspect, a method for selecting a batch or lot of a pharmaceutical preparation that contains a therapeutic agent that binds a human $Na_V1.7$ sequence is provided, comprising exposing a cell that bears a $Na_V1.7$ protein that comprises at least one contiguous human sequence to a sample of the batch or lot of the pharmaceutical preparation, determining whether the sample binds the cell, and selected a batch or lot that corresponds to the sample that bound the at least one contiguous human sequence. In one embodiment, the at least one contiguous human sequence encodes an extracellular pore loop of the $Na_V1.7$ protein. In a specific embodiment, the extracellular pore loop of the $Na_V1.7$ protein is selected from the loop connecting transmembrane segments 5 and 6 of Domain I, the loop connecting transmembrane segments 5 and 6 of Domain II, the loop connecting transmembrane segments 5 and 6 of Domain III, the loop connecting transmembrane segments 5 and 6 of Domain IV, and a combination thereof. In one embodiment, the extracellular pore loop is the loop connecting transmembrane segments 5 and 6 of Domain I. In one embodiment, the extracellular pore loop is the loop connecting transmembrane segments 5 and 6 of Domain III.

In one embodiment, the batch or lot of pharmaceutical preparation comprises a non-protein human $Na_V1.7$-binding compound. In one embodiment, the batch or lot of pharmaceutical preparation comprises a protein that binds to a human $Na_V1.7$. In a specific embodiment, the pharmaceutical preparation that comprises a protein includes an antibody.

In one embodiment, the cell that bears a $Na_V1.7$ protein that comprises at least one contiguous human sequence is in a mouse at the time that the sample of the batch or lot of the pharmaceutical preparation is exposed to the cell.

In one aspect, a method is provided for determining the efficacy of a $Na_V1.7$-binding protein for mediating a response resulting from a nociceptive stimulus, comprising exposing a mouse as described herein to the $Na_V1.7$-binding protein and measuring a nociceptive response of the mouse to the stimulus, wherein an attenuated nociceptive response of the mouse is an indicator of efficacy of the $Na_V1.7$-binding protein.

In one embodiment, the efficacy is determined for a batch or lot of pharmaceutical preparation. In a specific embodiment, the efficacy is determined as a quality assurance or quality control step in the manufacture of the pharmaceutical preparation for use in humans.

In one aspect, a method is provided for selectively engaging a target receptor on the surface of a neuronal cell, comprising: contacting an isolated cell from a mouse as described herein with one or more inflammatory mediators, thereby selectively engaging the target receptor; and, measuring the release of a neuropeptide.

In one embodiment, the method is employed as a functional assay to select an antagonist for the target receptor.

In one embodiment, the target receptor is a sodium channel. In a specific embodiment, the sodium channel is $Na_V1.7$.

In one embodiment, the neuronal cell is a dorsal root ganglion cell (DRG).

In one embodiment, the one or more inflammatory mediators are selected from prostaglandin $E_2$, bradykinin, capsaicin, protons, low pH, and a neurotrophic factor.

In one embodiment, the neuropeptide is calcitonin gene-related peptide (CGRP).

In one embodiment, a method is provided for selectively engaging a $Na_V1.7$ protein on the surface of a DRG, comprising exposing an isolated DRG from a mouse as described herein, to one or more inflammatory mediators thereby selectively engaging $Na_V1.7$ and measuring the release of CGRP.

In one embodiment, the one or more inflammatory mediators comprise prostaglandin $E_2$, bradykinin and capsaicin.

In one embodiment, the method is employed as a functional assay to select an antagonist for $Na_V1.7$. In a specific embodiment, the antagonist is an antibody.

In one aspect, a method for identifying a $Na_V1.7$ antagonist is provided, comprising: providing ex vivo a cell that expresses a human or chimeric $Na_V1.7$ protein; contacting the cell with an agent that binds to the human or chimeric $Na_V1.7$ protein; after a subsequent period of time, contacting the cell with one or more inflammatory mediators; after another subsequent period of time, determining the amount of calcitonin gene-related peptide (CGRP) released from the cell; and, comparing the amount of CGRP released from the cell in the presence of the agent that binds to the human or chimeric $Na_V1.7$ protein to a reference sample, wherein an increase in CGRP release over the reference sample indicates inhibition of $Na_V1.7$; and, determining if the agent inhibits the function of $Na_V1.7$.

In one embodiment, the agent is an antibody. In a specific embodiment, the antibody is human. In one embodiment, the agent is a peptide. In one embodiment, the agent is a non-proteinaceous organic compound. In one embodiment, the non-proteinaceous organic compound is selected from the group consisting of 2-alkyl-alkanoic acids (e.g., valproic acid and analogs thereof), 3-alkylamino-alkanoic acids (e.g., gabapentin and analogs thereof), 1-benzazapin-2-ones, bupivicaine, capsaicins, flecainide, flunarizine, lidocaine, mexiletine, phenyloin, propafefenone, prostaglandins, quinidine, saxitoxin, tetracaine, tetrodotoxin, and analogs thereof.

In one embodiment, the one or more inflammatory mediators are selected from prostaglandin $E_2$, bradykinin, capsaicin, protons, low pH, and a neurotrophic factor. In a specific embodiment, the one or more inflammatory mediators are prostaglandin $E_2$, bradykinin and capsaicin.

In one embodiment, the cell is a neuronal cell. In a specific embodiment, the neuronal cell is a dorsal root ganglion cell (DRG). In a specific embodiment, the cell is a mouse DRG cell. In one embodiment, the cell is isolated from a mouse as described herein. In a specific embodiment, the cell is an isolated DRG cell from a mouse as described herein.

In one embodiment, the amount of CGRP released in the presence of the agent that binds to the human or chimeric $Na_V1.7$ protein is about 1.5-fold, about 2-fold, about 3-fold, about 4-fold, about 5-fold, about, 6-fold, about 7-fold, about 8-fold, about 9-fold, about 10-fold, about 15-fold, or about 15-fold to about 20-fold higher than the reference sample. In a specific embodiment, the agent is a non-proteinaceous molecule. In one embodiment, the non-proteinaceous molecule is a toxin selected from tetrodotoxin and ProTx-II. In a specific embodiment, the agent is an antibody. In one embodiment, the antibody is an anti-$Na_V1.7$ antibody.

In one embodiment, the reference sample contains a sodium channel blocker. In a specific embodiment, the sodium channel blocker inhibits one or more functions of a sodium channel protein by binding to and inhibiting an extracellular pore opening of the channel protein. In one embodiment, the sodium channel blocker that inhibits one or more functions of a sodium channel protein by binding to and inhibiting an extracellular pore opening of the channel protein is an alkaloid-based toxin (e.g., tetrodotoxin or saxitoxin). In a specific embodiment, the sodium channel blocker inhibits one or more functions of a sodium channel by binding to and inhibiting an intracellular portion of the channel. In one embodiment, the sodium channel blocker that inhibits one or more functions of a sodium channel by binding to and inhibiting an intracellular portion of the channel is a local anesthetic (e.g., lidocaine). In one embodiment, the sodium channel blocker that inhibits one or more functions of a sodium channel by binding to and inhibiting an intracellular portion of the channel is an anticonvulsant (e.g., gabapentin, carbamazepine, clonazepam, divalproex, lamotrigine, phenyloin, oxcarbazepine, tiagabine, topiramate and valproic acid).

In one embodiment, the reference sample contains a toxin isolated from the venom of an arthropod, an invertebrate, a fish, or a reptile. In a specific embodiment, the toxic venom is derived from a tarantula (e.g., ProTx-II).

In one aspect, a method for identifying a $Na_V1.7$ antagonist is provided, comprising providing ex vivo a dorsal root ganglion (DRG) cell that expresses a human or chimeric $Na_V1.7$ protein, contacting the DRG with an agent that binds to the human or chimeric $Na_V1.7$ protein and waiting a first period of time, and, after the first period of time, contacting the DRG with one or more inflammatory mediators and waiting a second period of time, determining the amount of calcitonin gene-related peptide (CGRP) released from the DRG, comparing the amount of CGRP released from the DRG in the presence of the agent that binds to the human or chimeric $Na_V1.7$ protein to a reference sample, wherein an increase in CGRP release over the reference sample indicates inhibition of $Na_V1.7$, and determining if the agent inhibits the function of $Na_V1.7$ on the DRG.

In one embodiment, the agent is an antibody. In a specific embodiment, the antibody is human. In one embodiment, the agent is a peptide. In one embodiment, the agent is an organic compound.

In one embodiment, the one or more inflammatory mediators are prostaglandin $E_2$, bradykinin and capsaicin.

In one embodiment, the DRG is isolated from a member of the group consisting of human, mouse, rat, or monkey. In a specific embodiment, the DRG is isolated from a mouse as described herein. In one embodiment, the mouse comprises a nucleotide sequence encoding a human $Na_V1.7$ α-subunit or fragment thereof operably linked to a $Na_V$ promoter.

In one aspect, an ex vivo complex is provided; wherein the ex vivo complex comprises a mouse cell that expresses a $Na_V1.7$ protein comprising a mouse transmembrane domain and a human loop domain; and, a $Na_V1.7$ antagonist bound to the human loop. In one embodiment, the mouse cell is an immortalized cell. In one embodiment, the $Na_V1.7$ antagonist comprises an immunoglobulin variable domain that specifically binds a human $Na_V1.7$ loop but not a mouse $Na_V1.7$ loop.

In one aspect, an ex vivo complex is provided; wherein the ex vivo complex comprises a membrane or fragment thereof that comprises a $Na_V1.7$ protein that comprises a mouse transmembrane domain and a human loop domain; and, a $Na_V1.7$ antagonist bound to the human loop. In one embodiment, the $Na_V1.7$ antagonist comprises an immunoglobulin variable domain that specifically binds a human $Na_V1.7$ loop but not a mouse $Na_V1.7$ loop.

Any of the embodiments and aspects described herein can be used in conjunction with one another, unless otherwise indicated or apparent from the context. Other embodiments will become apparent to those skilled in the art from a review of the ensuing description. It is to be understood that both the foregoing general description and the following detailed description are exemplary and explanatory only and are not restrictive.

DETAILED DESCRIPTION

Figure 1:
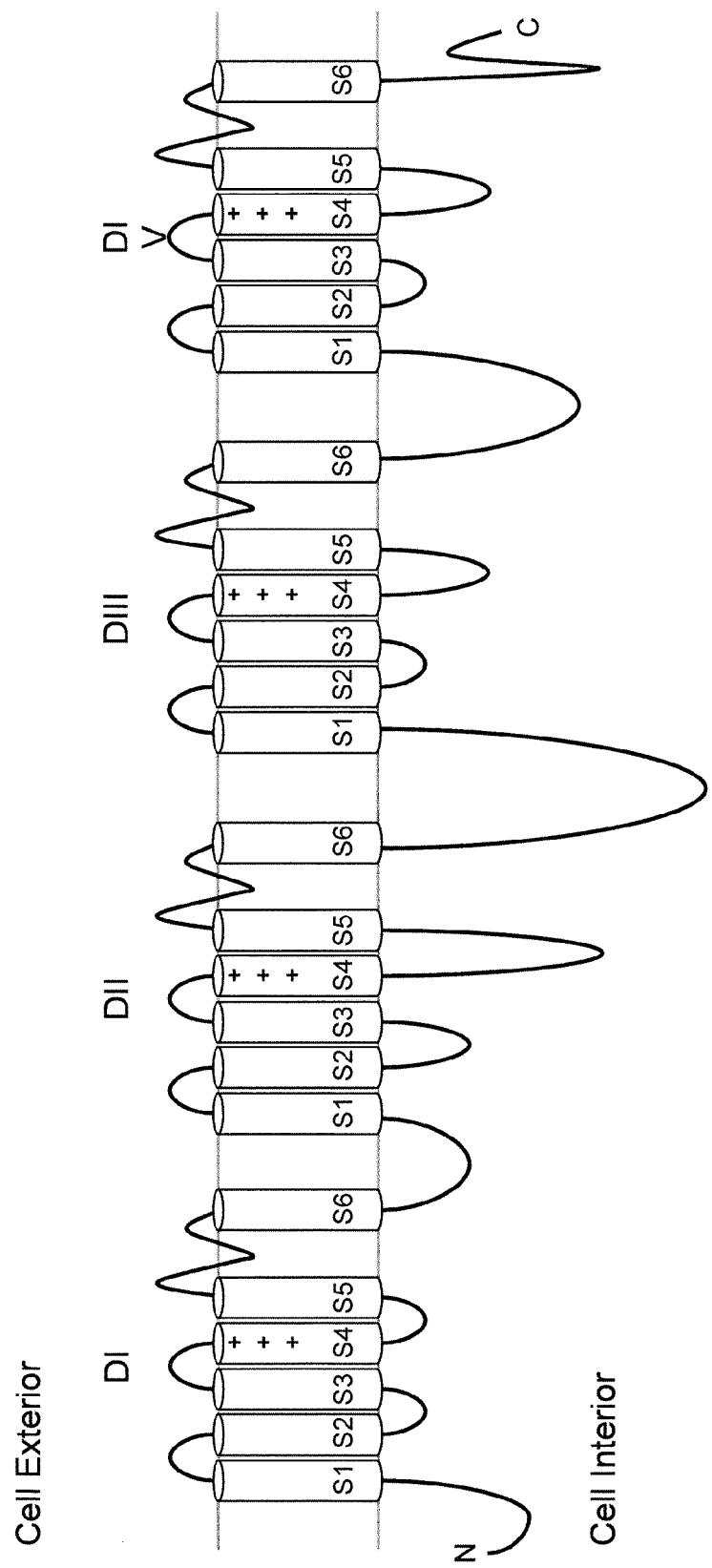
FIG. 1 shows a diagram of a $Na_V$ channel.

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The phrase "targeting vector" or "targeting construct" includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination.

Targeting regions that target using site-specific recombinase recognition sites (e.g., lox or FRT sites) are also included.

In a specific embodiment, the targeting construct further comprises a nucleic acid sequence or gene of particular interest, a selectable marker, control and or regulatory sequences, and other nucleic acid sequences that allow for recombination mediated through the exogenous addition of proteins that aid in or facilitate recombination involving such sequences. In another specific embodiment, the targeting construct further comprises a gene of interest, wherein the gene of interest is a heterologous gene that encodes a protein that has a similar function as a protein encoded by the endogenous sequence.

The term "replacement" includes wherein a DNA sequence is placed into a genome of a cell in such a way as to replace a sequence within a genome, at the locus of the genomic sequence, with a heterologous sequence (e.g., a human sequence in a mouse). The DNA sequence so placed may include one or more regulatory sequences that are part of source DNA used to obtain the sequence so placed (e.g., promoters, enhancers, 5'- or 3'-untranslated regions, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes a $Na_V$ channel, and the DNA fragment encodes one or more human $Na_V$ channels). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "$Na_V$ channel" includes a voltage-gated sodium channel, e.g., a $Na_V1.7$ channel. $Na_V$ channel genes include an α-subunit that is expressed on the surface of the cell and serves as a gate that allows the influx of $Na^+$ into the cell through a pore formed by transmembrane segments that are part of the α-subunit. The α-subunit associates with other subunits, e.g. β1, β2, β3 and β4, to carry out action potentials. There are several different $Na_V$ channel genes and they can be categorized by sensitivity to puffer fish toxin (tetrodotoxin, or TTX). TTX-sensitive channels, i.e. those blocked by low nanomolar TTX concentrations, include $Na_V1.1$, $Na_V1.2$, $Na_V1.3$, $Na_V1.4$, $Na_V1.6$ and $Na_V1.7$. TTX-resistant channels, i.e., those blocked by μM concentrations of TTX, include $Na_V1.5$, $Na_V1.8$ and $Na_V1.9$. Within the Nav channel genes, subtypes or mutants have been described in human subjects. By way of illustration, nucleotide and amino acid sequences of a human $Na_V1.7$ gene are provided in SEQ ID NOs: 42 and 43, respectively. Persons of skill upon reading this disclosure will recognize that one or more endogenous $Na_V$ channel genes in a genome (or all) can be replaced by one or more heterologous $Na_V$ channel genes (e.g., subtypes or mutants, genes from another species, chimeric forms, etc.).

The term "variants" includes variations of a normal sequence of a gene resulting in a series of different forms of the same gene. The different forms may comprise differences of up to, e.g., 20 amino acids in the sequence of a protein from a gene. For example, alleles can be understood to be alternative DNA sequences at the same physical gene locus, which may or may not result in different traits (e.g., heritable phenotypic characteristics) such as susceptibility to certain diseases or conditions that do not result in other alleles for the same gene or result in varying degrees in the other alleles.

An "excitable cell" includes a cell that is involved generating action potentials on stimulation. Exemplary excitable cells include neurons, myocytes and electrocytes. Excitable cells change the electrical potential of their membranes on stimulation in sudden and reversible manner to transmit electrical signals to other excitable cells thereby providing cell-to-cell communication. For example, voluntary muscle contraction is controlled by action potentials via neurons that innervate muscle fibers. In various embodiments, the genetically modified non-human animals of the present invention display action potentials controlled by the expression of the human and/or chimeric $Na_V1.7$ proteins on the surface of neurons in various types of tissues, e.g. muscle, within the non-human animal.

A "neuron" includes a nerve cell and is a specialized cell that exhibits, for example, electrical excitability. Neurons, as described herein, form complex membrane junctions with other neurons to form a contact thereby allowing one neuron to transmit signals to another. Such contacts between neurons are referred to in the art as synapses, which can be excitatory or inhibitory. Neurons can be a part of the central nervous system of an animal or be found in the periphery of the animal in other specialized nervous tissue, e.g. ganglia. For example, some neurons are situated in sensory organs such as the retina and cochlea.

The term "disruption" is used to refer to when a fragment of DNA recombines with an endogenous homologous sequence, e.g. a gene or gene locus. These sequence disruptions may include insertions, deletion, substitutions, replacements, missense, or a frameshift of DNA sequence, or any combination thereof. Insertions may include the insertion of entire genes or fragments of genes, e.g. exons, which may be of an origin other than the endogenous sequence. Disruption of an endogenous homologous sequence may alter the protein produced from a normal gene such that it is inhibited entirely or in part, or by the production of protein from a disrupted gene may be enhanced over the normal level of production from the non-disrupted endogenous homologous sequence. In one embodiment, the disruption results in a lack of functional protein produced from the endogenous homologous sequence. In another embodiment, the disruption has no significant effect on expression of the gene.

The phrase "endogenous locus" refers to the naturally occurring genetic locus found in a wild-type host animal that is to disrupted, deleted, replaced or altered. In one embodiment, the endogenous locus is deleted. In another embodiment, the endogenous locus is altered, wherein a portion of the endogenous locus is replaced with a heterologous sequence. In another embodiment, all or substantially all of the endogenous locus is replaced with a heterologous locus. In one embodiment, the heterologous locus is a human locus.

The term "heterologous" when used in conjunction with polypeptide or gene refers to a polypeptide having an amino acid sequence or a DNA encoding the polypeptide that is not found in the non-human host animal. Thus, a genetically modified mouse having a human $Na_V$ channel gene can be described as having a heterologous $Na_V$ channel gene. The replaced $Na_V$ channel gene can be detected using a variety of methods including, for example, PCR, Western blot, Southern blot, restriction fragment length polymorphism (RFLP), or a gain or loss of allele assay.

The phrase "endogenous promoter" refers to the promoter that is naturally associated, e.g., in a wild-type organism, with the polynucleotide sequence that encodes the endogenous protein.

The term "cell" includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The phrase "non-human animals" is intended to include any vertebrate such as cyclostomes, bony fish, cartilaginous fish such as sharks and rays, amphibians, reptiles, mammals, and birds. Suitable mammals include non-human primates, goats, sheep, pigs, dogs, cows, and rodents. Suitable non-human animals are selected from the rodent family including rat and mouse. In one embodiment, the non-human animals are mice.

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet, G. H., Cohen, M. A., and Benner, S. A. (1992) Exhaustive Matching of the Entire Protein Sequence Database, Science 256:1443-45, hereby incorporated by reference. In some embodiments, the substitution is a moderately conservative substitution wherein the substitution has a non-negative value in the PAM250 log-likelihood matrix.

The term "identity" when used in connection with a comparison of sequences, includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008).

The term "antibody", as used herein, is intended to refer to immunoglobulin molecules comprising four polypeptide chains, two heavy chains and two light chains inter-connected by disulfide bonds. Each heavy chain comprises a heavy chain variable region ($V_H$) and a heavy chain constant region ($C_H$). The heavy chain constant region comprises three domains for IgG, $C_H1$, $C_H2$ and $C_H3$ and a fourth domain, $C_H4$, in the case of IgM and IgE constant regions. Each light chain comprises a light chain variable region ($V_L$) and a light chain constant region. The light chain constant region comprises one domain of either a κ or λ type (Cκ or Cλ). The $V_H$ and $V_L$ regions can be further subdivided into regions of hypervariability, termed complementary determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The term "human antibody", as used herein, is intended to include antibodies having variable and constant regions derived from human germline immunoglobulin sequences, and may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

A "neutralizing" or "blocking" antibody, as used herein, is intended to refer to an antibody whose binding to a target molecule (e.g., $Na_V1.7$) results in inhibition of at least one function of the target molecule. For example, the inhibition caused by an $Na_V1.7$ neutralizing or blocking antibody need not be complete so long as it is detectable using an appropriate assay. Exemplary assays for detecting $Na_V1.7$ inhibition are described elsewhere herein.

The phrase "micromolar range" is intended to mean 1-999 micromolar; the phrase "nanomolar range" is intended to mean 1-999 nanomolar; the phrase "picomolar range" is intended to mean 1-999 picomolar.

$Na_V$ Channel Expression and Function

There are nine known members in the family of $Na_V$ channels. The gene names are SCN1A through SCN11A, and the respective proteins are designated $Na_V1.1$-$Na_V1.9$. Each have been further classified based on sensitivity to puffer fish toxin (tetrodotoxin, or TTX). The nine $Na_V$ channels have been reported to exhibit diverse functional properties and distinct expression patterns, which imply specialized functions among the channels. Expression of $Na_V$ channels can be detected, for example, in neurons of the central and peripheral nervous systems, cardiac myocytes, skeletal muscle, glia cells, and Schwann cells. $Na_V1.7$, a TTX-sensitive $Na_V$ channel also known as PN1 and SCN9A, has been detected in sympathetic neurons, Schwann cells, neuroendocrine cells and dorsal root ganglia (DRG). $Na_V1.7$ is almost exclusively expressed in DRG and concentrates in the tips of these specialized neurons. Such a distribution predisposes this channel for a role in transmitting pain signals.

$Na_V$ channels contain an α-subunit (FIG. 1) that forms a pore in the membrane of cells that allows the flow of $Na^+$ ions thereby mediating action potentials. This α-subunit also associates with one to two β-subunits, which function in the regulation of channel gating. The expression of the α-subunit on the surface of the cell appears to be required for channel function. $Na_V$ channels open and close through a pore, which is made up of the transmembrane segments 5 (S5) and 6 (S6) of each of the Domains (FIG. 1). It is through this pore formed by the cyclical arrangement of the four domains at the cell surface that $Na^+$ ions move into the cell and cause depolarization of the cell membrane. This action changes the electrochemical gradient of the cell and generates an action potential, which leads to the transmission of electrical signals between cells. Mutation studies have demonstrated that the amino acids making up the loops connecting the transmembrane segments both on the extracellular side and the intracellular side of the cell regulate the opening and closing of the channel in a gate-receptor type fashion. Such mutations alter and/or destabilize the state of the channel leaving the channel in a perpetual "on" or "off" state, therefore, causing what has been termed as channelopathies, e.g. hyperexcitability, which leads to severe and persistent pain states.

$Na_V1.7$ and Pain Pathways

Among the $Na_V$ channels, $Na_V1.7$ is associated with fast activation and inactivation, and has been postulated to act as a threshold channel. Genetic studies have linked $Na_V1.7$ to both severe pain as well as indifference to pain. For example, erythromelalgia (IEM) and paroxysmal extreme pain disorder (PEPD) result from $Na_V1.7$ mutations that increase channel activity by either shifting channel activation to a more negative potential or impairing inactivation. Other mutations have been described that lead to a non-functional $Na_V1.7$ protein and thus a complete absence of pain, called congenital indifference to pain (CIP). CIP mutations, while impairing the ability to smell, appear to have no effect on motor, cognitive and cardiac functions. Several $Na_V1.7$ mutations relating to IEM, PEPD and CIP and the resulting aberrant effect on $Na_V1.7$ function have been reported. $Na_V1.7$ has also been suggested to have a role in metastasis due to the finding that $Na_V1.7$ is up-regulated in some cancer cell lines. Further, nerve growth factor (NGF) has been demonstrated to increase $Na_V1.7$ levels, which has suggested a relationship to inflammatory pain. Accordingly, these findings indicate that $Na_V1.7$ is involved in several control points critical for the perception of pain, inflammation and, perhaps, the persistence of cancer.

Conventional therapies employing nonselective sodium channel inhibitors such as, for example, lidocaine, mexiletine, and carbamazepine show some value in the treatment of pain, however they are limited due to significant motor, cognitive and cardiac side effects from their inhibition on $Na_V$ channels not involved in the pain response. The use of analgesics, anticonvulsants and anti-arrhythmics for treating abnormal $Na_V$ activity has been met with similar results. This reveals the importance and immediate need for specific Nay inhibitors. Identification of therapeutics that selectively inhibit $Na_V1.7$ could prove effective to treat pain and inflammation in humans and the assessment of such therapeutics requires a suitable animal model that expresses human $Na_V1.7$. The present invention fulfils this and other needs.

Cell lines that stably express $Na_V$ channel proteins have proved difficult to construct and thus the development of suitable animal models to elucidate $Na_V$ channel function and identify specific inhibitors of $Na_V$ channels has been adversely affected. Also, deletion of murine $Na_V1.7$ is lethal, caused by an alleged decrease in olfaction, which is postulated to result in the failure to feed. Deletions of $Na_V1.7$ within subsets of cells have been achieved and confirmed a role in mechanisms of pain, but the applicability of this approach is not without limitation. A mouse in which the entire and/or specific portions of the human $Na_V1.7$ protein is expressed, in various embodiments could be used to accurately reflect human pain mechanisms and pathologies associated with disorders resulting from $Na_V1.7$ mutations. Such a mouse would serve as a vital tool in the engineering, analysis and evaluation of therapeutics for treatment of human pain disorders such as, e.g., IEM, PEPD, chronic and acute pain, and inflammatory pain, by providing an animal model capable of achieving a more accurate expression and function profile of $Na_V$ channel processes in humans. Further, cell lines derived from such mice would be exceptionally useful tools for evaluating human therapeutics.

Mice Expressing Heterologous $Na_V1.7$ Channels

Genetically modified non-human animals are provided that express fully or partially human $Na_V1.7$ protein. $Na_V1.7$ protein can be expressed on the surface of excitable cells, e.g. neurons, of the animal's nervous system.

The genetic modification, in various embodiments, comprises a deletion of a functional mouse $Na_V1.7$ gene in whole or in part, and in some embodiments a further modification comprising a replacement with a human $Na_V1.7$ gene in whole or in part, wherein the non-human animal expresses functional mouse β-subunits. Genetically modified non-human embryos, cells, and targeting constructs for making the non-human animals, non-human embryos, and cells are also provided.

Compositions and methods for making a mouse that expresses a human $Na_V1.7$ protein, including specific variants (e.g., single amino acid differences), are provided, including compositions and method for making a mouse that expresses such genes from a mouse promoter and a mouse regulatory sequence. The methods include selectively rendering an endogenous mouse $Na_V1.7$ gene nonfunctional (e.g., by a deletion of its α-subunit), and employing an α-subunit of a human $Na_V1.7$ gene at the endogenous mouse $Na_V1.7$ gene locus to express a human $Na_V1.7$ α-subunit gene in a mouse. The deletion of the mouse $Na_V1.7$ gene is made by deletion of the α-subunit gene, but not a β-subunit gene. The approach selectively renders the endogenous $Na_V1.7$ α-subunit gene nonfunctional while retaining a functional endogenous β-subunit.

The endogenous $Na_V1.7$ α-subunit replacement approach employs a relatively minimal disruption in natural $Na_V1.7$-mediated signal transduction in the animal, in various embodiments, because the genomic sequence of the $Na_V1.7$ α-subunits are replaced in a single fragment and therefore retain normal functionality by including necessary regulatory sequences. Thus, in such embodiments the $Na_V1.7$ α-subunit modification does not affect other endogenous $Na_V$ channel genes dependent upon functional β-subunits. Further, in various embodiments the modification does not affect the assembly of a functional receptor complex involving an $Na_V1.7$ α-subunit and an endogenous β-subunit, which are believed to be required for proper channel gating and modulation of channel expression of $Na_V1.7$ α-subunits on the cell surface and for downstream signaling resulting from an activated channel. Because the β-subunits are not deleted, animals containing a replacement of an endogenous $Na_V1.7$ α-subunit gene with a human $Na_V1.7$ α-subunit gene should be able to process normal voltage-gated $Na_V$ channel functions from Na+ passage into the cell through the pore of the human $Na_V1.7$ α-subunit present on the surface of neurons.

Figure 2:
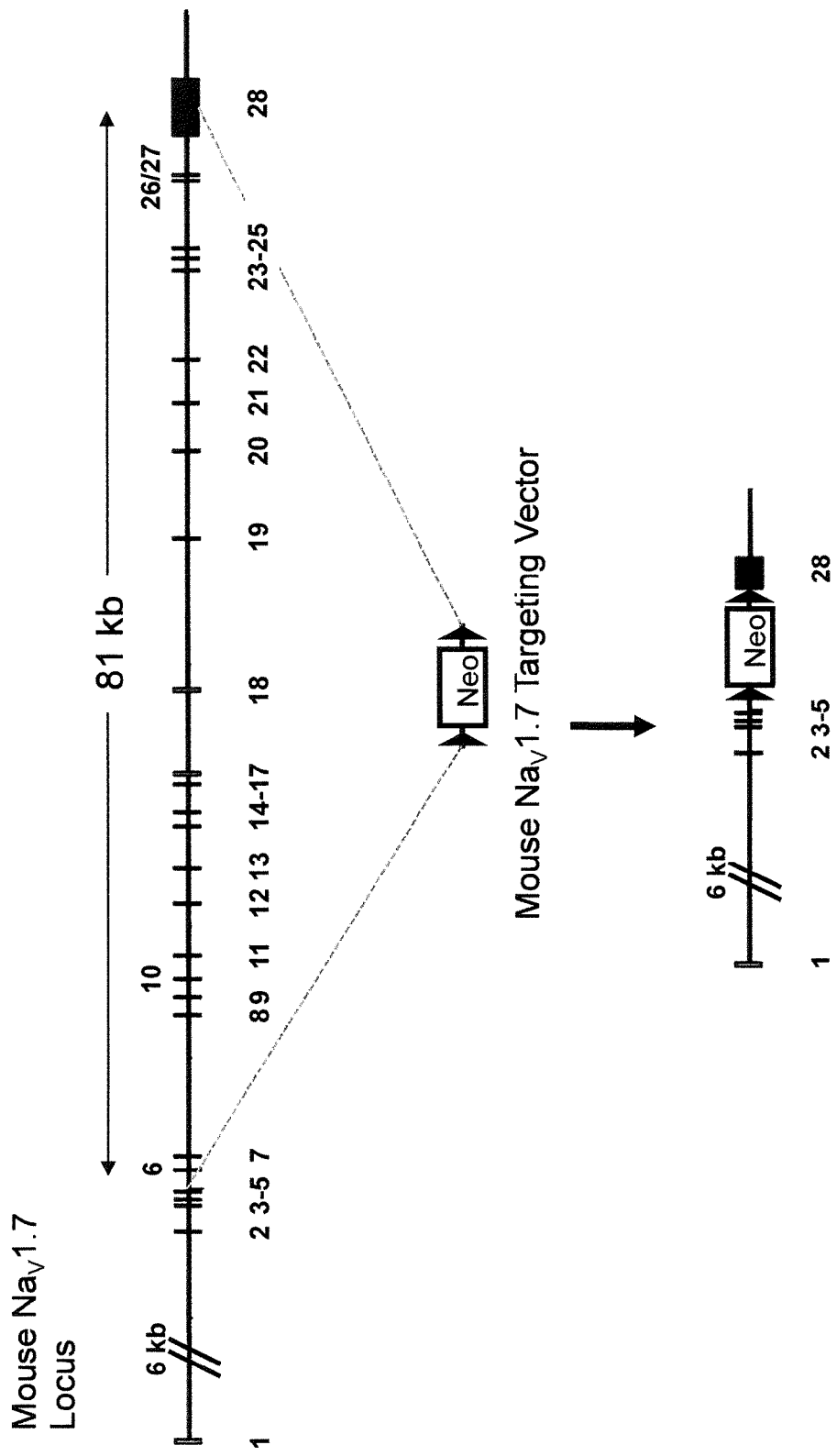
FIG. 2 shows the murine $Na_V1.7$ gene locus (top) with the exons numbered above and below the locus. The Mouse $Na_V1.7$ Targeting Vector (middle) was used to replace an 81 kb region of the endogenous locus spanning exons 6-28 with a neomycin cassette flanked by loxP sites. The targeted allele results in a deleted endogenous $Na_V1.7$ locus (bottom).

A schematic illustration (not to scale) of a deleted endogenous mouse $Na_V1.7$ gene is provided in FIG. 2. As illustrated, the mouse $Na_V1.7$ α-subunit is encoded by 28 exons spanning more than 80 kb of sequence. The endogenous mouse $Na_V1.7$ gene is deleted by a targeting construct (Mouse $Na_V1.7$ Targeting Vector) with a neomycin cassette flanked by recombination sites. This endogenous locus encodes the α-subunit of the mouse $Na_V1.7$ gene responsible for the generation of action potentials triggered by the depolarization of the cell membrane in response to flow of $Na^+$ ions into the interior of the cell.

A genetically modified mouse lacking a nucleotide sequence encoding an α-subunit of the endogenous $Na_V1.7$ gene can be made by any method known in the art. For example, a targeting vector can be made that deletes the mouse $Na_V1.7$ gene with selectable marker gene. FIG. 2 illustrates a mouse genome (bottom) targeted by a targeting construct having a 5' homology arm containing sequence upstream of exon 6 of the endogenous $Na_V1.7$ locus, followed by a drug selection cassette (e.g. a neomycin resistance gene flanked by loxP sequences), and a 3' homology arm containing sequence downstream of exon 27 of the endogenous $Na_V1.7$ locus. Upon homologous recombination at the locus, the endogenous $Na_V1.7$ locus is replaced by a drug selection cassette (FIG. 2, bottom). The endogenous $Na_V1.7$ locus is thereby deleted resulting in a cell or non-human animal that does not express endogenous $Na_V1.7$ α-subunit. The drug selection cassette may optionally be removed by the subsequent addition of a recombinase (e.g., by Cre treatment).

Genetically modifying a mouse to render endogenous $Na_V1.7$ gene nonfunctional, in various embodiments, results in a mouse that exhibits defects in processes of the nervous system, e.g. the transmission of nociceptive information, making the mouse useful for evaluating the role of the endogenous $Na_V1.7$ gene in normal and disordered neuronal function. In various embodiments, modifying the α-subunit of the endogenous $Na_V1.7$ gene, but not the β-subunits, avoids the potential reduction of other $Na_V$ genes (e.g., $Na_V1.6$, $Na_V1.8$, $Na_V1.9$, etc.) that require the β-subunits for regulating voltage-gating of the channel, thereby maintaining various other functions and processes mediated through β-subunit-dependent processes.

According to reports, complete deletions of the endogenous $Na_V1.7$ gene in mice are lethal. However, deletions in specific subsets of cells have been achieved and appear otherwise normal. Mice according to the present invention have a functionally silenced endogenous $Na_V1.7$ locus in that they lack the capacity of producing a functional $Na_V1.7$ α-subunit on the cell surface.

Figure 3:
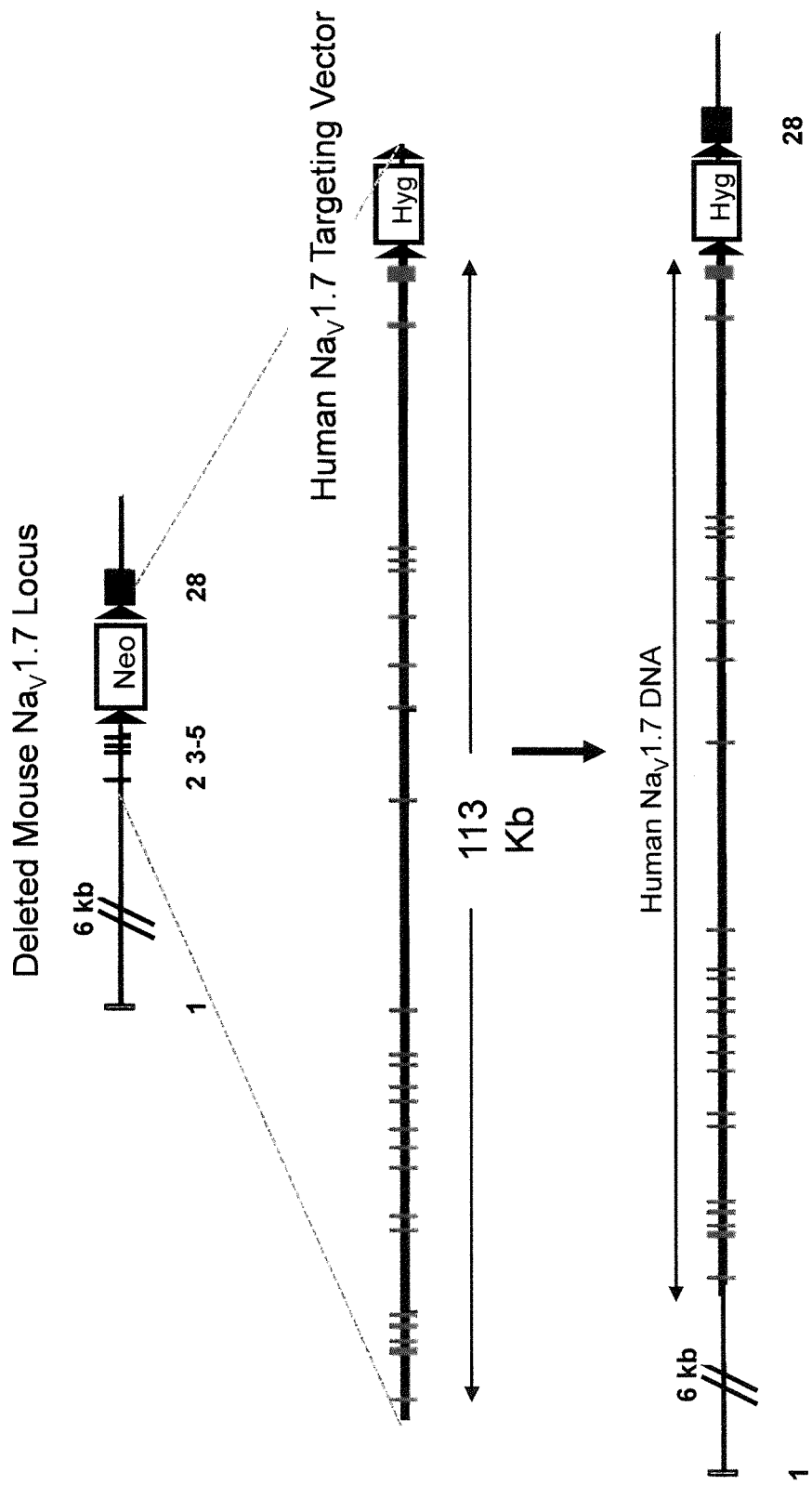
FIG. 3 shows the deleted endogenous $Na_V1.7$ locus (top) targeted with a Human $Na_V1.7$ Targeting Vector (middle). The deleted endogenous locus previously targeted with a neomycin cassette was replaced with a targeting vector comprising exons 2-28 of a human $Na_V1.7$ locus. The targeted allele results in an endogenous locus that expresses human $Na_V1.7$ protein.

A schematic illustration (not to scale) of a replaced endogenous mouse $Na_V1.7$ gene with a human $Na_V1.7$ gene is provided in FIG. 3. As illustrated, an endogenous mouse $Na_V1.7$ locus that had been deleted is replaced by a targeting construct (Human $Na_V1.7$ Targeting Vector) with a hygromycin cassette flanked by recombination sites. The resulting replaced locus encodes a human $Na_V1.7$ α-subunit protein expressed on the surface of neurons in the host animal capable of mediating action potentials triggered by the depolarization of the cell in response to flow of $Na^+$ ions into the cell within the host animal.

A genetically modified mouse that expresses a human $Na_V1.7$ α-subunit at the endogenous mouse $Na_V1.7$ locus can be made by any method known in the art. For example, a targeting vector can be made that introduces the human $Na_V1.7$ gene with a selectable marker gene. FIG. 3 illustrates a mouse genome comprising a replacement of the endogenous $Na_V1.7$ locus (bottom). The targeting construct contains a 5' homology arm containing sequence upstream of the endogenous mouse $Na_V1.7$ locus, followed by a genomic fragment containing a human $Na_V1.7$ gene, a drug selection cassette (e.g. a hygromycin resistance gene flanked on both sides by loxP sequences), and a 3' homology arm containing sequence downstream of the endogenous mouse $Na_V1.7$ locus. Upon homologous recombination at the endogenous locus, the drug selection cassette is replaced by the sequence contained in the targeting vector (bottom of FIG. 3). The deleted endogenous $Na_V1.7$ locus is thereby replaced with a human $Na_V1.7$ gene resulting in a cell or animal that expresses a human $Na_V1.7$ gene. The drug selection cassette may optionally be removed by the subsequent addition of a recombinase (e.g., by Cre treatment).

Other modifications to the endogenous locus can be achieved with minimal effort using similar techniques to create a locus comprising a chimeric gene. For example, schematic illustrations of the replacement of two extracellular pore loops between transmembrane segments 5 and 6 of Domain I and III of the endogenous mouse $Na_V1.7$ gene are provided in FIG. 4 and FIG. 5, respectively. As illustrated, discrete portions of a human $Na_V1.7$ gene are inserted into the endogenous mouse $Na_V1.7$ locus by other targeting constructs (Human $Na_V1.7$ DI/S5-S6 Targeting Vector and Human $Na_V1.7$ DIII/S5-S6 Targeting Vector) with genomic fragments that each encode an extracellular loop of a human $Na_V1.7$ gene located at the channel pore and responsible for allowing passage of Na+ ions into the intracellular space. Upon recombination with either one of the illustrated targeting vectors, a genomic fragment of the endogenous $Na_V1.7$ locus, which encodes an extracellular pore loop of the endogenous $Na_V1.7$ protein, is replaced with a human genomic fragment encoding the corresponding pore loop in a human $Na_V1.7$ protein. This creates a chimeric locus that produces a chimeric $Na_V1.7$ protein that comprises human extracellular loops in the pore of a $Na_V1.7$ channel protein.

Figure 4:
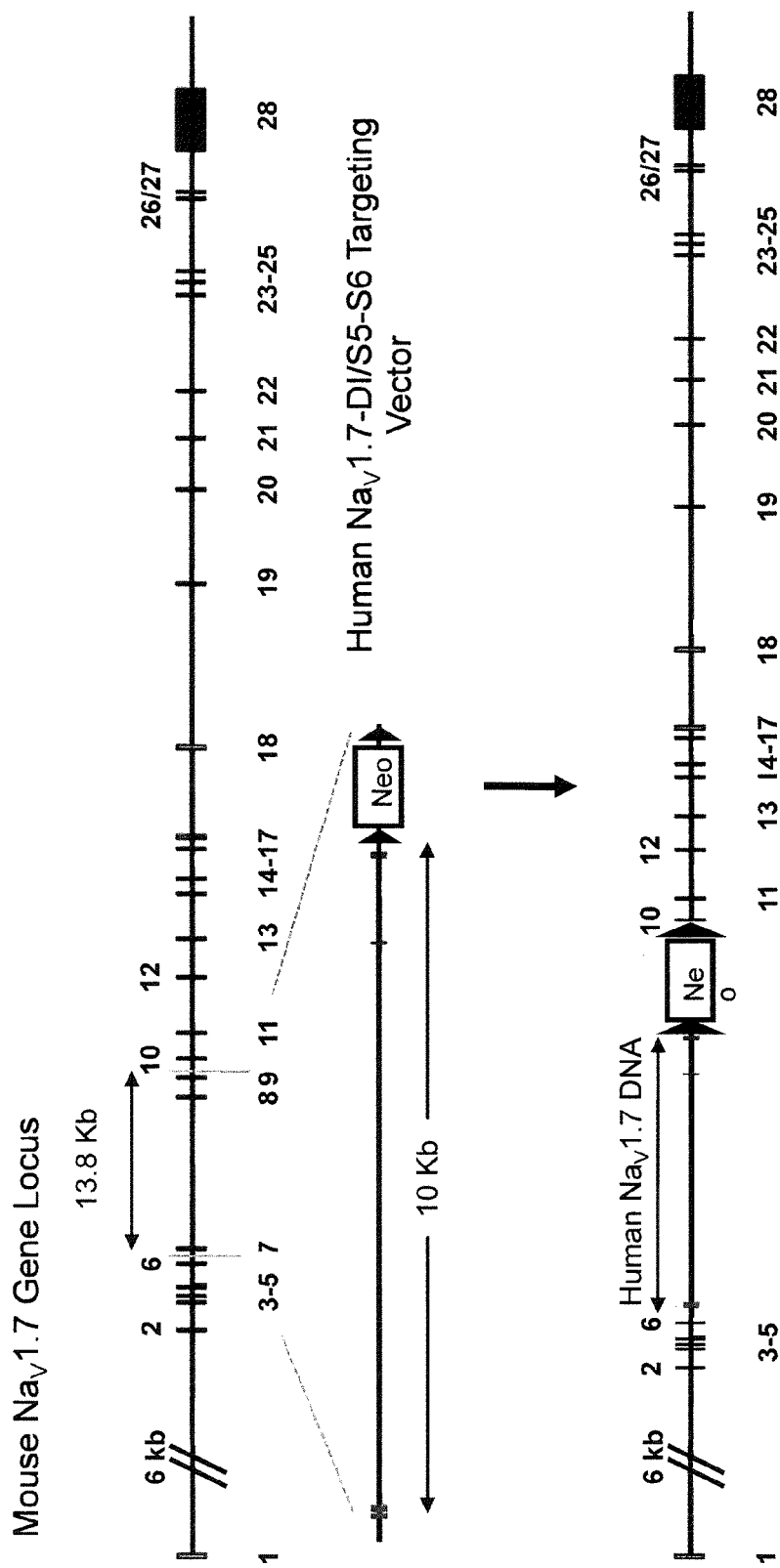
FIG. 4 shows the mouse $Na_V1.7$ locus (top) targeted with a Human $Na_V1.7$-DI/S5-S6 Targeting Vector (middle). The targeted allele results in a partially humanized endogenous $Na_V1.7$ locus that expresses a chimeric $Na_V1.7$ protein that includes a human extracellular S5-S6 pore loop in Domain I.
Figure 5:
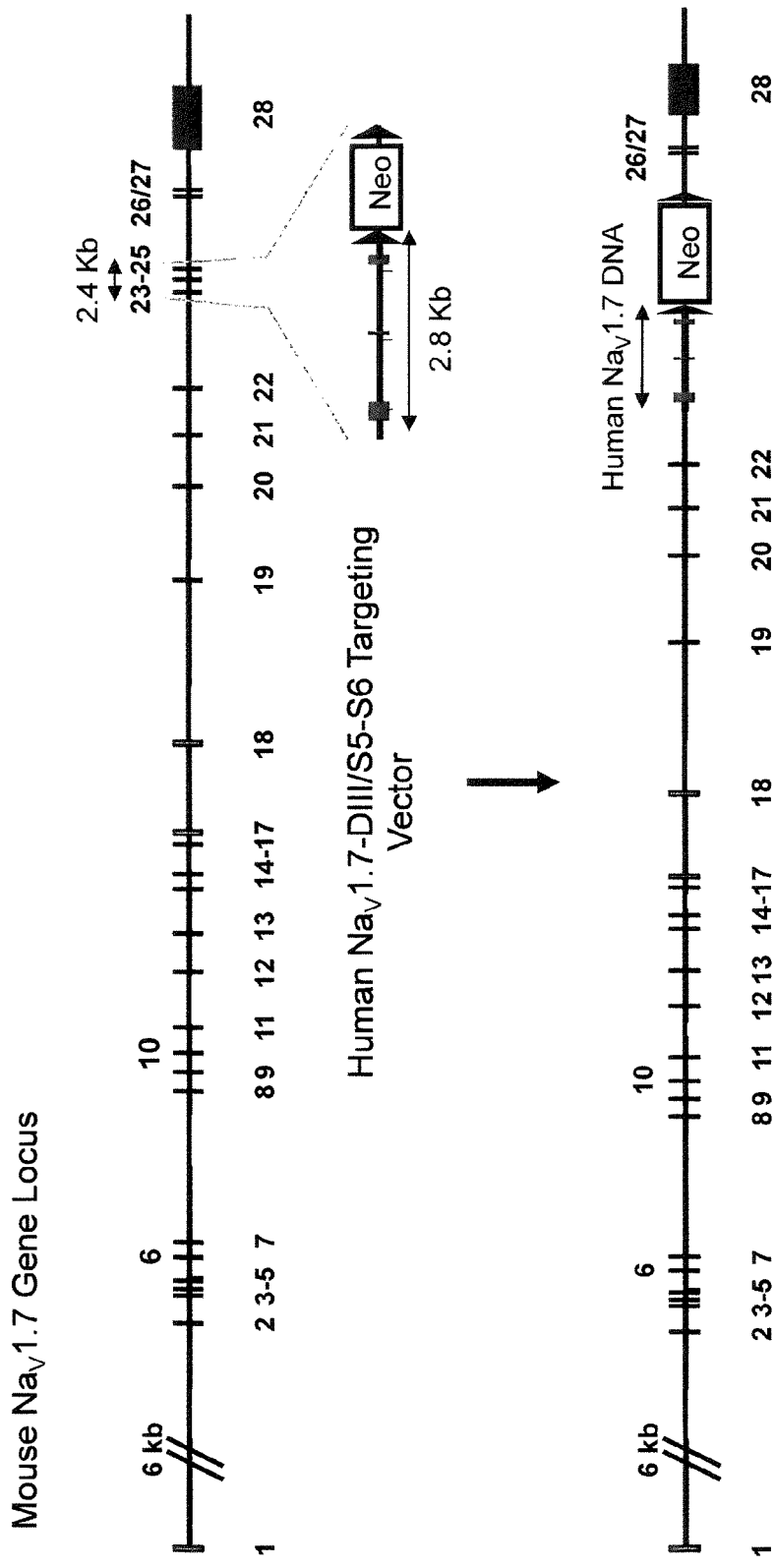
FIG. 5 shows the mouse $Na_V1.7$ locus (top) targeted with a Human $Na_V1.7$-DIII/S5-S6 Targeting Vector (middle). The targeted allele results in a partially humanized endogenous $Na_V1.7$ gene locus that expresses a chimeric $Na_V1.7$ protein that includes a human extracellular S5-S6 pore loop in Domain III.

A genetically modified mouse that expresses an extracellular pore loop of a human $Na_V1.7$ channel at the endogenous mouse $Na_V1.7$ locus can be made by any method known in the art. For example, a targeting vector can be made that introduces a genomic fragment that encodes an extracellular pore loop of a human $Na_V1.7$ channel with a selectable marker gene. FIGS. 4 and 5 each illustrate a mouse genome comprising separate replacements of extracellular loops located at the pore of a $Na_V1.7$ channel protein. Each targeting construct contains a 5' homology arm containing sequence upstream of the endogenous mouse $Na_V1.7$ sequence to be replaced, followed by a genomic fragment containing a human sequence corresponding to the endogenous mouse $Na_V1.7$ gene sequence that encodes a specific extracellular pore loop, a drug selection cassette (e.g. a neomycin resistance gene flanked on both sides by loxP sequences), followed by a 3' homology arm containing sequence downstream of the endogenous mouse Na$_V$1.7 sequence to be replaced. Upon homologous recombination at the endogenous locus with either of the targeting vectors, a genomic fragment is inserted into the endogenous mouse Na$_V$1.7 locus resulting in a chimeric locus capable of expressing a Na$_V$1.7 channel protein comprising a human sequence corresponding to an extracellular pore loop (FIGS. 4 and 5, bottom). The drug selection cassette may optionally be removed by the subsequent addition of a recombinase (e.g., by Cre treatment).

Experimental Models of Na$_V$1.7 Humanized Mice

Genetically modified non-human animals that express human Na$_V$1.7 genes are useful, e.g., to elucidate the various functions of Na$_V$1.7 in the cells of the nervous system, to measure the efficacy of a therapeutic agent that binds to the Na$_V$1.7 protein expressed on the cell surface, to determine a Na$_V$1.7 channel's role in mechanisms of pain and pain disorders, to serve as models of acute and/or chronic pain, and to serve as breeding mates to generate other genetically modified mice of interest. They are also useful for preparing membrane fractions or vesicles that comprise fully human or chimeric human-mouse Na$_V$1.7 proteins, for identifying antagonists of human Na$_V$1.7.

In one embodiment, a mouse according to the invention is used to determine the mechanism of channel gating that is regulated by the extracellular loops located in the pore of human Na$_V$ channels. In one embodiment, a mouse of the present invention is injected with toxins that bind to extracellular pore loops of a human Na$_V$ channel on the cell surface and, after a subsequent period of time, subjected to a range of stimuli to trigger firing of action potentials. The identity of the toxin is known prior to injection and the animals are analyzed for impairment of Na$_V$1.7-dependent electrical responses by comparison to electrical responses observed in wild type animals.

In another aspect, genetically modified non-human animals comprising a replacement of the endogenous Na$_V$1.7 gene with a human Na$_V$1.7 gene is provided. Such animals are useful for studying the efficacy of therapeutic agents to block Na$_V$1.7 function. In addition, human Na$_V$1.7 has been shown to exhibit mutant forms associated with disease (e.g. IEM, PEPD and CIP). Thus, genetically modified non-human animals that comprise a replacement of the endogenous Na$_V$1.7 gene with specific mutant forms of human Na$_V$1.7 genes can be used to study human disorders associated with Na$_V$1.7 mutations in the animal. In a specific embodiment, the mutant forms of human Na$_V$1.7 are associated with the pain response.

Suitable variants include mutant forms of human Na$_V$1.7 that are known in the art. Variants associated with the IEM disorder include, for example, mutations that shift activation of Na$_V$1.7 to a more negative potential. Exemplary Na$_V$1.7 mutations that lead to IEM include Q10R, I136V, F216S, S241T, N395K, V400M, L823R, I848T, L858H, L858F, A863P, V872G and F1449V. In one embodiment, the human Na$_V$1.7 sequence comprises a missense mutation that causes the IEM disorder. In a specific embodiment, the missense mutation that causes the IEM disorder is selected from I848T and L858H.

Variants associated with the PEPD disorder include, for example, mutations that compromise inactivation of a Na$_V$1.7 α-subunit. Mutations that cause PEPD have been shown to shift the steady-state fast inactivation of a Na$_V$1.7 α-subunit toward a state characterized by more depolarized potentials causing a notable increase in continuous current. Such mutations have been reported to occur, for example, in the amino acids linking DIII and DIV, which contains an inactivation motif associated with inactivating the Na$_V$1.7 α-subunit. Exemplary Na$_V$1.7 mutations that lead to PEPD include R996C, V1298D, V1298F, V1299F, I1461T, F1462V, T1464I, M1627K and A1632E. In one embodiment, the human Na$_V$1.7 sequence comprises a mutation selected from I1461T, M1627K and A1632E.

Variants associated with the CIP disorder include, for example, homozygous single-nucleotide non-sense mutations and compound heterozygous mutations, which include non-sense mutations on one allele and a deletion mutation on the other allele. The deletion mutation can be of coding or non-coding sequences, the latter of which can lead to defective splicing that functionally silence the Na$_V$1.7 α-subunit. Nonsense mutations are changes in DNA sequence, which introduce premature stop codons, causing any resulting protein to be abnormally shortened. This can cause a loss of function in the protein, as critical parts of the amino acid chain are no longer translated. Accordingly, non-human animals of the present invention comprising a human Na$_V$1.7 α-subunit with a mutation that functionally silence the human Na$_V$1.7 α-subunit demonstrate an absence of pain in response to nociceptive stimuli.

Exemplary silencing mutations in a Na$_V$1.7 gene include nonsense mutations, deletions of one or more nucleotide in a Na$_V$1.7 DNA sequence, mutations in the splice junction of exons, and frameshift mutations. In one embodiment, the genetically modified non-human animal is heterozygous for a silencing mutation that leads to CIP, wherein one allele of a Na$_V$1.7 gene comprises a non-sense mutation and the other Na$_V$1.7 allele comprises a frameshift mutation selected from F1200L and I1235L. In another embodiment, the genetically modified non-human animal is homozygous for a non-sense mutation that leads to CIP. In one embodiment, the non-sense mutation comprises a truncated Na$_V$1.7 α-subunit protein that ends at an amino acid residue selected from 259, 277, 328, 459, 693, 767, 830, 897, 1488, 1659 and 1689. In a specific embodiment, the human Na$_V$1.7 α-subunit protein ends at an amino acid residue selected from 693 and 1488.

Expression of mouse Na$_V$1.7 in whole mice was analyzed using a reporter system comprising a fusion of a LacZ reporter gene with mouse Na$_V$1.7. Analysis of LacZ signal in whole mice revealed that Na$_V$1.7 is expressed in the entire mouse nervous system, including in brain (including olfactory bulb ganglia), thalamus, hypothalamus, midbrain, pons, medulla, colliculus, optic nucleus, cerebral cortex, spinal cord gray matter (e.g., dorsal/sensory), dorsal root ganglia, sympathetic ganglion chain, trigeminal ganglia, celiac ganglion, intestine nervous plexus, and in smaller ganglia throughout the body (e.g., tongue, esophagus, trachea, bronchi, heart).

Thus, cells, cell lines, and cell cultures can be made from the above-mentioned tissues as a source of mouse Na$_V$1.7 protein. Further, genetically modified mice according to the invention express partially or fully humanized Na$_V$1.7 on the above-mentioned tissues. Thus the tissues and cells from the genetically modified mice, including cell lines and cell cultures, can be generated to serve as a source of humanized Na$_V$1.7 for use in binding and functional assays, e.g., to assay for binding or function of a Na$_V$1.7 agonist or antagonist, particularly where the agonist or antagonist is specific for a human Na$_V$1.7 sequence.

Cells from genetically modified mice can be isolated and used on an ad hoc basis, or can be maintained in culture for many generations. In one embodiment, cells from the genetically modified mice are immortalized and maintained in culture indefinitely (e.g., in serial cultures).

In one aspect, the genetically modified mice are used to make modified dorsal root ganglia (DRG) that comprise one or more of the modified $Na_V1.7$ proteins. The modified DRG(s) are employed in ex vivo assays to determine the effect of a $Na_V1.7$ binding agent on the function of the $Na_V1.7$ protein and on the function of other proteins, e.g., other $Na_V$ family members. In one embodiment, modified DRG(s) from a mouse are isolated and assayed for one or more $Na_V1.7$ functions in the presence and absence of a $Na_V1.7$ binding agent (e.g., a $Na_V1.7$ agonist or antagonist). In one embodiment, the modified DRG(s) are isolated and assayed for the function of one or more $Na_V$ family members in the presence and absence of a $Na_V1.7$ binding agent. In one embodiment, the modified DRG(s) are assayed in the presence of the binding agent for function of a non-$Na_V$ family protein or channel.

In one embodiment, a method for determining the effect of a $Na_V1.7$ binding agent on a DRG channel that is not a $Na_V$ family member is provided, comprising exposing modified DRG(s) comprising to a $Na_V1.7$ binding agent, and measuring a function of a non-$Na_V$ family member DRG channel.

In another aspect, a method is provided for determining an effect of a human therapeutic on a human $Na_V1.7$, wherein the human therapeutic does not bind a human $Na_V1.7$ protein, comprising exposing a modified DRG to the human therapeutic in an ex vivo assay, and measuring an effect of the human therapeutic on a function of a human $Na_V1.7$ protein.

In various embodiments and aspects, a DRG or modified DRG is assayed or a function of a DRG protein or modified DRG protein is ascertained in a patch clamp protocol, a calcium imaging protocol, a membrane-sensitive dye protocol, in an ex vivo assay.

In one aspect, a cell culture is provided, wherein the cell culture comprises a cell of a genetically modified mouse as described herein, wherein a substantial number of the cells in the culture express a human $Na_V1.7$ sequence. In one embodiment, the cells that express the human $Na_V1.7$ sequence are immortalized. In one embodiment, the cells are derived from a tissue selected from brain (including olfactory bulb ganglia), thalamus, hypothalamus, midbrain, pons, medulla, colliculus, optic nucleus, cerebral cortex, spinal cord gray matter (e.g., dorsal/sensory), dorsal root ganglia, sympathetic ganglion chain, trigeminal ganglia, celiac ganglion, intestine nervous plexus, and in smaller ganglia throughout the body (e.g., tongue, esophagus, trachea, bronchi, heart).

In one aspect, a method for determining whether a putative $Na_V1.7$ agonist or antagonist binds a human $Na_V1.7$ protein is provided, comprising exposing the putative $Na_V1.7$ agonist or antagonist to a cell as described herein, and determining whether the putative $Na_V1.7$ agonist or antagonist binds the cell.

In one embodiment, the human $Na_V1.7$ agonist or antagonist is selected from a protein, a peptide, and a small molecule (e.g., non-protein organic compound). In a specific embodiment, the protein comprises an immunoglobulin variable domain or $Na_V1.7$-binding fragment thereof. In a specific embodiment, the protein is an anti-human $Na_V1.7$ antibody.

In one aspect, a method for determining whether a pharmaceutical preparation affects a function of a human $Na_V1.7$ is provided, comprising exposing the pharmaceutical preparation to a cell as provided herein that expresses a human $Na_V1.7$ protein, and measuring a $Na_V1.7$ function of the cell.

In one embodiment, the $Na_V1.7$ function measured is primary nociceptor activation. In a specific embodiment, the function measured is calcitonin gene-related peptide (CGRP) release by the cell.

In one embodiment, the pharmaceutical preparation comprises a protein, a peptide, or a peptide analog. In a specific embodiment, the protein comprises an immunoglobulin variable domain or $Na_V1.7$-binding fragment thereof. In a specific embodiment, the protein is an anti-human $Na_V1.7$ antibody.

In one aspect, a quality assurance assay for a pharmaceutical preparation comprising an agent that binds a human $Na_V1.7$ sequence is provided, comprising obtaining a sample of a pharmaceutical preparation and exposing the preparation to a mouse or a cell as described herein, where the mouse or the cell expresses a human $Na_V1.7$ sequence, and determining (a) whether the pharmaceutical preparation binds the cell, and/or (b) determining whether the pharmaceutical preparation affects a $Na_V1.7$ function of the cell.

In one embodiment, the pharmaceutical preparation is an isolated human antibody or fragment thereof. In one embodiment, the pharmaceutical preparation is a non-antibody ion channel blocker or analog thereof.

Neuropeptide Release from Neurons of $Na_V1.7$ Humanized Mice

Primary nociceptive neurons are amenable to a number of well-established research techniques, such as electrophysiology recordings, calcium imaging and measurement of spontaneous and stimulated neuropeptide release, that provide insights in cellular and molecular functions of single neurons or neuronal subpopulations.

Calcitonin gene-related peptide (CGRP), a 37-amino-acid peptide, is predominantly synthesized and stored in sensory neurons and can be released from both central and peripheral axons (Poyner, D. R. 1992. Calcitonin gene-related peptide: multiple actions, multiple receptors. *Pharmacol. Ther.* 56(1): 23-51). The release of CGRP from sensory nerve terminals in peripheral tissues plays a key role in neurogenic inflammation whereas the release from terminals in the dorsal horn of the spinal cord modulates pain transmission (Oku, R., M. Satoh, N, Fujii, A. Otaka, H. Yajima, and H. Takagi. 1987. Calcitonin gene-related peptide promotes mechanical nociception by potentiating release of substance P from the spinal dorsal horn in rats. *Brain Res.* 403(2): 350-354). CGRP knock out mice show an attenuated response to chemical pain and inflammation (Salmon, A., M. I. Damaj, L. M. Marubio, M. P. Epping-Jordan, E. Merlo-Pich, and J. P. Changeux. 2001. Altered neuroadaptation in opiate dependence and neurogenic inflammatory nociception in αCGRP-deficient mice. *Nature Neuroscience* 4(4): 357-358), which implicates CGRP in regulating the pain response.

A variety of inflammatory mediators, such as prostaglandin $E_2$, bradykinin, and protons, or other stimulants such as low pH, neurotrophic factors and capsaicin play an essential role in the induction of pain. Further, inflammatory mediators are known to induce the release of neuropeptides by activating specific membrane receptors. For example, inflammatory mediators such as prostaglandin $E_2$ and bradykinin excite and sensitize DRG neurons leading to action potentials that are blocked by tetrodotoxin (Noda, K., Y. Ueda, K. Suzuki, and K. Yoda. 1997. Excitatory effects of algesic compounds on neuronal processes in murine dorsal root ganglion cell culture. *Brain Res.* 751 (2): 348-351; Nicol G. D. and M. Cui. 1994. Enhancement by prostaglandin $E_2$ of bradykinin activation of embryonic rat sensory neurones. *Journal Physiol.* 480(Pt 3): 485-492; Momin A. and P. A. McNaughton. 2009. Regulation of firing frequency in nociceptive neurons by pro-inflammatory mediators. *Exp Brain Res.* 196(1): 45-52). These mediators have also been shown to regulate CGRP expression in cultured dorsal root ganglion (DRG) neurons (Supowit S. C., H. Zhao, K. A. Katki, P. Gupta, and D. J. Dipette 2011. Bradykinin and prostaglandin $E_1$ regulate calcitonin gene-related peptide expression in cultured rat sensory neurons. *Regul Pept.* 167(1): 105-111; Averbeck, B., I. Izydorczyk, and M. Kress. 2000. Inflammatory mediators release calcitonin gene-related peptide from dorsal root ganglion neurons of the rat. *Neuroscience* 98(1): 135-140). Moreover, prostaglandin $E_2$ enhances bradykinin- and capsaicin-stimulated release of CGRP (Vasko M. R., W. B. Campbell, and K. J. Waite. 1994. Prostaglandin $E_2$ enhances bradykinin-stimulated release of neuropeptides from rat sensory neurons in culture. *J. Neurosci.* 14(8): 4987-4997; Southhall, M. D. and M. R. Vasko. 2001. Prostaglandin receptor subtypes EP3C and EP4 mediate the prostaglandin $E_2$-induced cAMP production and sensitization of sensory neurons. *J. Biol. Chem.* 276: 16083-16091). The release of CGRP from stimulated nerves is blocked by the sodium channel antagonist tetrodotoxin (TTX) and by omega conotoxin (CTX) but not nifedipine, a known calcium channel blocker (Lundberg, J. M., A. Franco-Cereceda, K. Alving, P. Delay-Goyet, and Y. Lou. 1992. Release of Calcitonin Gene-Related Peptide from Sensory Neurons. *Ann NY Acad. Sci.* 657:187-93). These latter findings suggest that while N-type calcium channels are important for peptide exocytosis from stores located in large dense cored vesicles of primary afferents, sodium channels also play a role in CGRP release. Similar characteristics have been demonstrated for the peptide release evoked by low concentrations of capsaicin, which is also sensitive to both TTX and CTX. However, high concentration of capsaicin causes a massive release of CGRP which is only marginally inhibited, if at all, by TTX or CTX (Lou Y. P., A. Franco-Cereceda, and J. M. Lundberg. 1992. Different ion channel mechanisms between low concentrations of capsaicin and high concentrations of capsaicin and nicotine regarding peptide release from pulmonary afferents. *Acta Physiol. Scand.* 146(1): 119-127). These reports suggest that the CGRP release induced by different inflammatory agents is dependent on different channels/receptors and/or pathways. Thus, the correct stimulation for engagement of specific target receptors known to be associated with pain responses can be identified through the measurement of CGRP release from neurons. This allows for the specific functional analysis of a target receptor and the discovery of how the target receptor functions in pain responses.

Depolarization of neurons leads to an increase in neuropeptide expression and release, in particular an increase in expression of CGRP. The release of CGRP has been used in several studies to assess the mediation of the pain response and characterization of neuronal function including the generation of action potentials with respect to other channels (although not sodium channels). As described above, inflammatory mediators, e.g., bradykinin and prostanglin $E_2$, have been shown to induce CGRP release from dorsal root ganglion (DRG) in culture (Averbeck, B. et al., supra; Tumati, S., W. R. Roeske, T. W. Vanderah, and E. V. Varga. 2010. Sustained morphine treatment augments prostaglandin $E_2$-evoked calcitonin gene-related peptide release from primary sensory neurons in a PKA-dependent manner. *Eur. J. Pharmacol.* 648(1-3):95-101). Although in vitro CGRP release from DRG has revealed an essential role for calcium channels, involvement in sodium channels has remained less clear (Ai, X., S. E. MacPhedran, and A. K. Hall. 1998. Depolarization stimulates initial CGRP expression by embryonic sensory neurons in vitro. *J. Neurosci.* 18(22): 9294-9302; Strecker, T., K. Messlinger, M. Weyand, and P. W. Reeh 2005. Role of different proton-sensitive channels in releasing calcitonin gene-related peptide from isolated hearts of mutant mice. *Cardiovasc. Res.* 65(2):405-410; Spitzer, M. J., P. W. Reeh, and S. K. Sauer. 2008. Mechanisms of potassium- and capsaicin-induced axonal calcitonin gene-related peptide release: involvement of L- and T-type calcium channels and TRPV1 but not sodium channels. *Neurosci.* 151(3):836-842). Thus, there remains a need to develop assays that assess neuronal function mediated by sodium channels, in particular through the application of DRGs that express a human $Na_V1.7$ protein.

Methods for the measurement of neuropeptide release from neurons isolated from mice that express human $Na_V1.7$ are useful, e.g., to elucidate the function of nociceptive neurons expressing a human $Na_V1.7$ protein in response to inflammatory mediators by measurement of CGRP release. They are also useful for identification of $Na_V1.7$-specific antagonists through the assessment of their ability to alter or modify inflammatory mediator-induced release of CGRP in DRG isolated from mice expressing a human $Na_V1.7$ protein.

DRG neurons, known to express $Na_V1.7$, release CGRP upon depolarization. This property of DRG neurons suggests that DRGs that express human $Na_V1.7$ can be used in an assay as a means to identify antagonists of $Na_V1.7$ using measurement of CGRP released from isolated DRG in culture. Thus, neurons (for example, DRG neurons) that express a human $Na_V1.7$ or a chimeric $Na_V1.7$ may be employed in an assay to identify $Na_V1.7$ antagonists that engage human or chimeric $Na_V1.7$ channels in DRG neurons and assess the functional activity of the channel through measurement of CGRP release. In such an assay, e.g., the human or chimeric $Na_V1.7$ is incubated with an inhibitor of $Na_V1.7$ (e.g., tetrodotoxin) for about twenty minutes, followed by stimulation with one or more inflammatory mediators (e.g., prostaglandin $E_2$, bradykinin, and capsaicin) for an additional twenty minutes. Additional candidate antagonists may be employed in this assay to assess their therapeutic potential and ability to block $Na_V1.7$ channel function. Once baseline measurements of CGRP release from the neurons that express a human or chimeric NaV1.7 are determined both in the presence of a known inhibitor of $Na_V1.7$ (e.g., TTX) and the absence of a known inhibitor (i.e., inflammatory mediators only), increase in CGRP release can be easily determined when employing candidate antagonists in this assay. Thus, an assay adapted to engage a $Na_V$ channel protein such as $Na_V1.7$ is useful, e.g., for identification of $Na_V1.7$-specific antagonists through the assessment of their ability to alter or modify the level of CGRP release in DRG isolated from mice expressing a human $Na_V1.7$ protein that are exposed to inflammatory mediators.

Assays are described herein that measure neuropeptide release in neuronal cells in response to one or more inflammatory mediators, which can be used as functional tests for selecting antagonists to a target receptor. Specifically, assays are described herein that measure CGRP release from cultured DRGs for assessment of sodium channel function in the presence and absence of specific antagonists, in particular the DRGs express a human $Na_V1.7$ protein, and that provide novel in vitro methods for the evaluation of primary nociceptor activation. In one embodiment, DRG neurons are contacted with one or more inflammatory mediators (e.g., prostaglandin $E_2$, bradykinin and capsaicin, to specifically engage TTX-sensitive $Na_V$ channels, specifically $Na_V1.7$) and the release of CGRP induced by the inflammatory mediators is determined.

Neurotrophins such as GDNF, neurturin and artemin have been shown to enhance capsaicin-induced release of CGRP (Schmutzler, B. S., S. Roy, and C. M. Hingtgen. 2009. Glial cell line-derived neurotrophic factor family ligands enhance capsaicin-stimulated release of calcitonin gene-related peptide from sensory neurons. *Neurosci.* 161:148-156; Schmutzler, B. S., S. Roy, S. K. Pittman, R. M. Meadows, and C. M. Hingtgen. 2011. Ret-dependent and Ret-independent mechanisms of Gfl-induced sensitization. *Molecular Pain* 7:1-22). Neurotrophins preferentially bind to their own GDNF family receptor (GFRα1, GFRα2 and GFRα3), and there is a 90% co-expression of GFRα3 with TRPV1, which is also known as the capsaicin receptor. Capsaicin is an agonist of TRPV1 and almost all neurons expressing TRPV1 also express CGRP. Artemin alone does not change the basal level of CGRP release. However, pre-incubation with artemin for ten minutes before stimulation with 1 μM capsaicin significantly enhances CGRP release. Thus, an assay in which neurons are incubated with artemin (e.g., at 10 ng/mL) or GDNF (e.g., at 10 ng/mL) for ten minutes, followed by capsaicin stimulation for an additional ten minutes, may be employed to specifically engage GFRα3 and assess functional activity of the receptor through measurement of CGRP release from DRG neurons in vitro. Additionally, the assay may employ specific antagonists of, e.g., GFRα3 to determine their ability to block receptor activity and/or function.

The assay principle can be adapted for another target receptor, for example, TRPA1. Mustard oil, a specific agonist of TRPA1, has been shown to induce the release of CGRP from isolated rat hindpaw skin (Ruparel, N. B., A. M. Patwardhan, A. N. Akopian, and K. M. Hargreaves. 2008. Homologous and heterologous desensitization of capsaicin and mustard oil responses utilize different cellular pathways in nociceptors. *Pain* 135:271-279). Thus, an assay in which DRG neurons isolated from a mouse as described herein, are exposed to mustard oil could be used to specifically engage TRPA1 to serve as a means to functionally assess activity of TRPA1 through measurement of CGRP release from DRG neurons in vitro. Additionally, specific antagonists could be employed in the assay to determine their ability to block TRPA1 activity and/or function.

The assay principle can be adapted for yet another target receptor, for example, ASIC1 and/or ASIC3. ASIC1 and ASIC3 are proton-gated cationic channels that are activated by external pH variations ranging from pH 6.8 to 4.0. Low pH has been shown to trigger CGRP release. Thus, an assay in which DRG neurons isolated from a mouse as described herein, are exposed to low pH conditions in culture could be used to specifically engage ASIC1 (or ASIC3) to serve as a means to functionally assess activity of ASIC1 (or ASIC3) through measurement of CGRP release from DRG neurons in vitro. Additionally, specific antagonists could be employed in the assay to determine their ability to block ASIC1 (or ASIC3) activity and/or function.

In one aspect, a method for measuring activity of a target receptor is provided, comprising contacting an inflammatory mediator to a cell having a target receptor encoded by a humanized mouse gene, wherein the inflammatory mediator binds the target receptor, and determining target receptor-mediated neuropeptide release from the cell. In one embodiment, the inflammatory mediator is a $Na_V1.7$ ligand, and the target receptor is a humanized mouse $Na_V1.7$.

In one aspect, a method for selectively engaging a target receptor is provided, comprising contacting an isolated cell from a mouse as described herein with one or more inflammatory mediators, thereby selectively engaging the target receptor and determining the release of a neuropeptide from the isolated cell.

In one embodiment, the target receptor is a sodium channel. In a specific embodiment, the sodium channel is $Na_V1.7$.

In one embodiment, the cell is a neuronal cell. In a specific embodiment, the neuronal cell is a dorsal root ganglion cell (DRG). In one embodiment, the cell is an immortalized cell.

In one embodiment, the one or more inflammatory mediators are selected from prostaglandin $E_2$, bradykinin, capsaicin, protons, low pH, a neurotrophic factor and a combination thereof.

In one embodiment, the neuropeptide is calcitonin gene-related peptide (CGRP).

In one embodiment, the method is employed as a functional assay to select an antagonist for the target receptor.

In one embodiment, a method is provided for selectively engaging a $Na_V1.7$ protein on the surface of an isolated DRG from a mouse as described herein, comprising contacting the DRG with one or more inflammatory mediators thereby selectively stimulating $Na_V1.7$ and determining the release of CGRP.

In one embodiment, the one or more inflammatory mediators comprises prostaglandin $E_2$, bradykinin and capsaicin.

In one embodiment, the method is employed as a functional assay to select an antagonist for $Na_V1.7$. In a specific embodiment, the antagonist is an antibody.

In one aspect, a method for measuring the release of CGRP from an isolated DRG from a mouse as described herein is provided, in particular to determine the effect of a $Na_V$-specific antagonist on CGRP release associated with depolarization of a human $Na_V1.7$ channel protein, in particular through stimulation with one or more inflammatory mediators (e.g., prostanglin $E_2$, bradykinin, serotonin, histamine and capsaicin).

In one embodiment, the DRG is immortalized.

In one embodiment, the Nay-specific antagonist is selected from a protein, a small molecule, and a small interfering RNA (siRNA). In a specific embodiment, the $Na_V$-specific antagonist is a protein.

In one embodiment, an isolated DRG from a mouse as described herein is cultured in the presence of a Nay-specific toxin and, after a subsequent period of time, the release of CGRP is determined, wherein an elevated level of CGRP expression indicates inhibition of $Na_V$-specific function in the DRG cell. The identity of the $Na_V$-specific antagonist is known prior to culture with the DRG and the DRG is analyzed for baseline level of CGRP expression in the presence and absence of the one or more inflammatory mediators.

In one embodiment, the Nay-specific toxin is selected from tetrodotoxin (TTX), ProTx-II, and lidocaine. In a specific embodiment, the $Na_V$-specific toxin is TTX.

In one embodiment, an isolated DRG from a mouse as described herein is cultured in the presence of a $Na_V1.7$-specific antibody, and CGRP release is determined, wherein an elevated level of CGRP expression indicates inhibition of $Na_V1.7$ function in the DRG cell. The identity and biochemical profile (e.g., affinity, specificity, etc.) of the $Na_V1.7$-specific antibody is known prior to culture with the DRG and the DRG is analyzed for baseline level of CGRP expression in the presence and absence of the one or more inflammatory mediators.

In one embodiment, the $Na_V1.7$-specific antibody is a human antibody. In one embodiment, the $Na_V1.7$-specific antibody is a mouse antibody. In one embodiment, the $Na_V1.7$-specific antibody is a bispecific antibody.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example I

Deletion of an Endogenous $Na_V1.7$ Locus

The targeting vector for introducing a deletion of the endogenous $Na_V1.7$ gene was made using VELOCIGENE® technology (see, e.g., U.S. Pat. No. 6,586,251 and Valenzuela, D. M., Murphy, A. J., Frendewey, D., Gale, N. W., Economides, A. N., Auerbach, W., Poueymirou, W. T., Adams, N. C., Rojas, J., Yasenchak, J., Chemomorsky, R., Boucher, M., Elsasser, A. L., Esau, L., Zheng, J., Griffiths, J. A., Wang, X., Su, H., Xue, Y., Dominguez, M. G., Noguera, I., Torres, R., Macdonald, L. E., Stewart, A. F., DeChiara, T. M., Yancopoulos, G. D. 2003. High-throughput engineering of the mouse genome coupled with high-resolution expression analysis. *Nature Biotech.* 21(6): 652-659) to modify the Bacterial Artificial Chromosome (BAC) RP23-454H3 (Invitrogen). RP23-454H3 BAC DNA was modified to delete the endogenous $Na_V1.7$ gene comprising the α-subunit of this $Na_V$ channel gene that is expressed on the cell surface (FIG. 2).

Briefly, upstream and downstream homology arms were derived mouse BAC DNA from locations 5' of exon 6 and 3' of exon 28 of the endogenous $Na_V1.7$ locus, respectively. These homology arms were used to make a cassette that deleted ~81 kb of the endogenous $Na_V1.7$ locus comprising exons 6 to 28. This region was replaced with a neomycin cassette flanked by loxP sites (FIG. 2, middle). The final targeting vector from 5' to 3' included a 17 kb homology arm comprising mouse genomic sequence 5' to exon 6 of the endogenous $Na_V1.7$ locus, a 5' loxP site, a neomycin cassette, a 3' loxP site and a 29 kb homology arm comprising mouse genomic sequence 3' to exon 28 of the endogenous $Na_V1.7$ locus. The targeting vector was linearized by digesting with AgeI and then used in homologous recombination in bacterial cells containing the mouse BAC clone RP23-454h3 to achieve a targeted deletion of the endogenous $Na_V1.7$ locus (FIG. 2, bottom).

The targeted BAC DNA (described above) was used to electroporate mouse ES cells to created modified ES cells comprising a deletion of the endogenous $Na_V1.7$ locus. Positive ES cells containing a deleted endogenous $Na_V1.7$ locus were identified by the quantitative PCR assay using TAQ-MAN® probes (Lie, Y. S. and C. J. Petropoulos. 1998. *Curr. Opin. Biotechnology* 9: 43-48). The upstream region of the deleted locus was confirmed by PCR using primers 867TUP2F (GGGACTTCTC TGGGTTCAGT TA; SEQ ID NO: 1) and 867TUP2R (AAAGGCTCTC AATGGGAAAC AAG; SEQ ID NO: 2) and probe 867TUP2P (TCAATGACTT GACATAATGC ATGCACTCC; SEQ ID NO: 3), whereas the downstream region of the deleted locus was confirmed using primers 867TDPF (ATGTCAGCCA ATCCTTCTAA AGTG; SEQ ID NO:4) and 867TDPR (CGTTTTGCCT AAGGCGGTAC; SEQ ID NO:5) and probe 867TDPP (TCCTATGAGC CCATCACAAC CACAC; SEQ ID NO: 6). The presence of the neomycin cassette from the targeting vector was confirmed using primers NEOF (GGTGGAGAGG CTATTCGGC; SEQ ID NO:7) and NEOR (GAACACGGCG GCATCAG; SEQ ID NO: 8) and probe NEOP (TGGGCACAAC AGACAATCGG CTG; SEQ ID NO: 9). The nucleotide sequence across the upstream deletion point included the following, which indicates endogenous mouse sequence upstream of the deletion point (contained within the parentheses below) linked contiguously to cassette sequence present at the deletion point: (CTAGCTGAGC TGTCACCACA CATTGCTCCT ACCACGTATT GTACAGCTAC TGCAAGAGCA CCACAGTTGG CTTTCTGTAT C) ATAACTTCGT ATAATGTATG CTATACGAAG TTAT (SEQ ID NO: 10). The nucleotide sequence across the downstream deletion point included the following, which indicates cassette sequence contiguous with endogenous mouse sequence downstream of the deletion point (contained within the parentheses below): ATAACTTCGT ATAATGTATG CTATACGAAG TTAT (AGCTTCGGTT TTGATACACT GTTTACAGCC TGCGAAGGTG ACTCACTCGT GTTAATAAGA CTCTTTTACG GAGGTCTATG CCAAACTCTT TTTATCAAAT ATTCTCAAAG GCAG) (SEQ ID NO: 11). Positive ES cell clones were then used to implant female mice using the VELOCIMOUSE® method (described below) to generate a litter of pups containing a deletion of the endogenous $Na_V1.7$ locus.

Targeted ES cells described above were used as donor ES cells and introduced into an 8-cell stage mouse embryo by the VELOCIMOUSE® method (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. 2007. F0 generation mice that are essentially fully derived from the donor gene-targeted ES cells allowing immediate phenotypic analyses. *Nature Biotech.* 25(1): 91-99). Mice bearing a deletion of exons 6 to 28 in the endogenous $Na_V1.7$ locus were identified by genotyping using a modification of allele assay (Valenzuela et al., supra) that detected the presence of the neomycin cassette and confirmed the absence of endogenous $Na_V1.7$ sequences.

Mice bearing a deletion of exons 6 to 28 in the endogenous $Na_V1.7$ locus can be bred to a Cre deletor mouse strain (see, e.g., International Patent Application Publication No. WO 2009/114400) in order to remove any loxed neomycin cassette introduced by the targeting vector that is not removed, e.g., at the ES cell stage or in the embryo. Optionally, the hygromycin cassette is retained in the mice.

Pups are genotyped and a pup heterozygous for the deleted endogenous $Na_V1.7$ sequences is selected for characterizing endogenous $Na_V1.7$ deletion.

Example II

Humanization of an Endogenous $Na_V1.7$ Locus

A targeting vector for replacement of the endogenous $Na_V1.7$ locus with the human $Na_V1.7$ locus (FIG. 3) was constructed using a two step process involving ligation of BAC DNA and GAP repair (Zhang, Y., J. P. P. Muyrers, G. Testa, and F. A. Stewart. 2000. DNA cloning by homologous recombination in *Escherichia coli. Nature Biotechnology* 18:1314-1317; Zhang, Y., F. Buchholz, J. P. P. Muyrers, and F. A. Stewart. 1998. A new logic for DNA engineering using recombination in *Escherichia coli. Nature Genetics* 20:123-128).

The first step in constructing the replacement targeting vector was performed by ligation of a DNA fragment of mouse BAC DNA clone RP23-454H3 with a human DNA fragment from human BAC clone RP11-1002M1 (Invitrogen). This ligation of mouse and human BAC DNA fragments created a modified BAC clone containing a replacement of exons 5 to 28 of the mouse $Na_V1.7$ locus (about 81 kb) with exons 5 to 28 of the human $Na_V1.7$ locus (about 100 kb).

The second step in constructing the replacement targeting vector was performed by GAP repair (referenced above)

using mouse BAC clone RP23-454H3 and human BAC clone RP11-45AJ20 to add additional exons of the human $Na_v1.7$ locus to the modified BAC clone made in the first step. GAP repair was performed on using these mouse and human BAC clones to replaced exons 2 to 7 of the endogenous $Na_v1.7$ locus with exons 2 to 7 of the human $Na_v1.7$ locus (~13 kb). This second step added the ~13 kb of human $Na_v1.7$ sequence to the ~100 kb of human $Na_v1.7$ sequence to make the replacement of the endogenous $Na_v1.7$ locus. A hygromycin cassette flanked by loxP sites was added to the 3' end of the ~113 kb BAC fragment containing the human $Na_v1.7$ locus (FIG. 3, middle)

Upstream and downstream homology arms were derived from mouse BAC DNA at positions 5' and 3' of the endogenous $Na_v1.7$ locus for addition to the human DNA fragment-hygromycin cassette to create the final targeting vector for replacement of the endogenous $Na_v1.7$ locus which contained from 5' to 3' a 5' homology arm containing 70 kb of mouse DNA 5' of the endogenous $Na_v1.7$ locus, a ~113 kb DNA fragment containing exons 2 to 28 of the human $Na_v1.7$ locus, a hygromycin cassette flanked by loxP sites, and a 3' homology arm containing 147 kb of mouse DNA 3' of the endogenous $Na_v1.7$ locus. The targeting vector was linearized by digesting with NotI and then used in homologous recombination in bacterial cells to achieve a targeted replacement of the endogenous $Na_v1.7$ locus with exons 2 to 28 of the human $Na_v1.7$ locus (FIG. 3, bottom).

The targeted BAC DNA (described above) was used to electroporate mouse ES cells to created modified ES cells comprising a replacement of the endogenous mouse $Na_v1.7$ locus with a genomic fragment comprising a human $Na_v1.7$ locus. Positive ES cells containing a deleted endogenous $Na_v1.7$ locus replaced by a genomic fragment comprising a human $Na_v1.7$ locus were identified by a quantitative PCR assay using Taqman probes (Lie and Petropoulos, supra). The upstream and downstream regions outside of the modified locus were confirmed by PCR using the same primers and probes as described in Example 1 (867TUP2F/867TUP2R/867TUP2P and 867TDPF/867TDPR/867TDPP). The insertion of the human $Na_v1.7$ sequence was confirmed by PCR using primers 935HF (ATCAAAGGAA CCCAAAGAAG; SEQ ID NO: 12) and 935HR (GAAGGGCAGC TGTTTGC-CAG; SEQ ID NO: 13) and probe 935HP (ATGAAGAAGC CCCAAAGCCA AGCA; SEQ ID NO: 14). The presence of the hygromycin cassette from the targeting vector was confirmed with primers HYGF (TGCGGCCGATCTTAGCC; SEQ ID NO: 15) and HYGR (TTGACCGATTCCTTGCGG; SEQ ID NO: 16) and probe HYGP (ACGAGCGGGTTCG-GCCCATTC; SEQ ID NO: 17). The nucleotide sequence across the upstream insertion point included the following, which indicates endogenous mouse sequence upstream of the insertion point (contained within the parentheses below) linked contiguously to human $Na_v1.7$ genomic sequence present at the insertion point: (TTAGGTAAGG ATC-CGAAGGG GAAATAAAAC CTACAGGATG AGAAG) ATGGCAATGT TGCCTCCCCC AGGACCTCAG AGCTTTGTCC ATTTCACAAA ACAG (SEQ ID NO: 18). The nucleotide sequence across the downstream insertion point at the 5' end of the hygromycin cassette included the following, which indicates human $Na_v1.7$ genomic sequence contiguous with cassette sequence downstream of the insertion point (contained within the parentheses below): GTAT-GAATAA AAAAGCATTG AAATAGGGAT TCTTGC-CAAC TTGCTC (TCTCGAGATA ACTTCGTATA ATGTATGCTA TACGAAGTTA T) (SEQ ID NO: 19). The nucleotide sequence across the downstream insertion point at the 3' end of the hygromycin cassette included the following, which indicates cassette sequence contiguous with mouse genomic sequence at the 3' end of the endogenous $Na_v1.7$ locus (contained within the parentheses below): TATAC-GAAGT TATGCTAGTA ACTATAACGG TCCTAAGGTA GCGAGCTAG (CAGCTTCGGT TTTGATACAC TGTT-TACAGC CTGCGAAGGT G) (SEQ ID NO: 20). Positive ES cell clones were then used to implant female mice using the VELOCIMOUSE® method (supra) to generate a litter of pups containing a replacement of the endogenous $Na_v1.7$ locus with a human $Na_v1.7$ locus.

Targeted ES cells described above were used as donor ES cells and introduced into an 8-cell stage mouse embryo by the VELOCIMOUSE® method (supra). Mice bearing a human $Na_v1.7$ locus were identified by genotyping using a modification of allele assay (Valenzuela et al., supra) that detected the presence of a human $Na_v1.7$ locus.

Mice bearing a human $Na_v1.7$ locus can be bred to a Cre deletor mouse strain (see, e.g., International Patent Application Publication No. WO 2009/114400) in order to remove any loxed hygromycin cassette introduced by the targeting vector that is not removed, e.g., at the ES cell stage or in the embryo. Optionally, the hygromycin cassette is retained in the mice.

Pups are genotyped and a pup heterozygous for a human $Na_v1.7$ locus is selected for characterizing $Na_v1.7$ humanization.

Example III

Humanization of the Extracellular Loop of Transmembrane Segments 5 to 6 in Domain I of an Endogenous $Na_v1.7$ Locus A targeting vector for humanization of the extracellular pore loop connecting transmembrane segments 5 and 6 of Domain I (DI/S5-S6) was constructed by the GAP repair method (described above) using mouse BAC clone RP23-20C24 and human BAC clone RP11-45AJ20 (FIG. 4). The GAP repair method was used to replace a 13.8 kb DNA fragment containing exons 7 to 9 of the endogenous $Na_v1.7$ locus with a 10 kb DNA fragment containing exons 7 to 9 of the human $Na_v1.7$ locus. A neomycin cassette flanked by loxP sites was added to the end of the 10 kb human DNA fragment containing exons 7 to 9 of the human $Na_v1.7$ locus (FIG. 4, middle).

Upstream and downstream homology arms were derived from mouse BAC DNA at positions 5' and 3' of exons 7 and 9, respectively, and added to the 10 kb human fragment-neomycin cassette to create the final targeting vector for humanization of the extracellular pore loop connecting transmembrane segments 5 and 6 of Domain I of the endogenous $Na_v1.7$ locus which contained from 5' to 3' a 5' homology arm containing 35 kb of mouse DNA 5' of exon 7 of the endogenous $Na_v1.7$ locus, a 10 kb DNA fragment containing exons 7 to 9 of the human $Na_v1.7$ locus, a neomycin cassette flanked by loxP sites, and a 3' homology arm containing 27 kb of mouse DNA 3' of exon 9 of the endogenous $Na_v1.7$ locus. The targeting vector was linearized by digesting with PspX and SalI and then used in homologous recombination in bacterial cells to achieve a targeted replacement of exons 7 to 9 in endogenous $Na_v1.7$ locus with exons 7 to 9 of a human $Na_v1.7$ gene (FIG. 4, bottom).

The targeted BAC DNA (described above) was used to electroporate mouse ES cells to created modified ES cells comprising a replacement of exons 7 to 9 in the endogenous mouse $Na_v1.7$ locus with a genomic fragment comprising exons 7 to 9 of a human $Na_v1.7$ locus. Positive ES cells containing a genomic fragment comprising exons 7 to 9 of a human Na$_v$1.7 gene were identified by the quantitative PCR assay using Taqman probes (Lie and Petropoulos, supra). The upstream region outside of the modified region of the endogenous locus were confirmed by PCR using primers 869TUPF (GGACTACAAC TGTTTATGGG CAAC; SEQ ID NO: 21) and 869TUPR (TCAATTCTTC TTCACTCTCA GCAG; SEQ ID NO: 22) and probe 869TUPP (TCCGGAAGGA CCTTGAGCAG AATGA; SEQ ID NO: 23), whereas the downstream region outside the modified region of the endogenous locus was confirmed with primers 869TDPF (CAA-CAGGTGA GCAGCAACAG; SEQ ID NO: 24) and 869TDPR (GCAGGAGACA CATACACCAG AC; SEQ ID NO: 25) and probe 869TDPP (AAACACGCAT GTCT-GAAGGC AGTCGG; SEQ ID NO: 26). The presence of the neomycin cassette from the targeting vector was confirmed using the same primers and probe as described in Example 1. The nucleotide sequence across the upstream insertion point included the following, which indicates endogenous mouse sequence upstream of the insertion point (contained within the parentheses below) linked contiguously to human Na$_v$1.7 genomic sequence present at the insertion point: (TACATTT-TAA GGACTAAAAA CCATCGTGGG GGCCCTGATC CAATCAGTGA AGAAGCTCTC TGACGTCATG ATCCT-CACTG TGTTCTGTCT CAGTGTGTTC) GCACTAATTG GACTACAGCT GTTCATGGGA AACCTGAAGC ATAAATGTTT TCGAAATTCA CTTGAAAATA ATGAAACATT AGAAAGCATA ATGAATACCC T (SEQ ID NO: 27). The nucleotide sequence across the downstream insertion point at the 5' end of the neomycin cassette included the following, which indicates human Na$_v$1.7 genomic sequence contiguous with cassette sequence downstream of the insertion point (contained within the parentheses below): AGGTGAGTAC CAAGAGAAAC ATGCATTGTA TTTTTGAATG GCATATGTAC CTGGTGTATG TTAA-GAGCCT GTATTAGGAG GTTTTTTATT TATTTGAGAA TGGAGGAAAC TCTATTA (CTCGAGATAA CTTCG-TATAA TGTATGCTAT ACGAAGTTAT) (SEQ ID NO: 28). The nucleotide sequence across the downstream insertion point at the 3' end of the neomycin cassette included the following, which indicates cassette sequence contiguous with mouse genomic sequence 3' of exon 9 of the endogenous Na$_v$1.7 locus (contained within the parentheses below): TATACGAAGT TATGCTAGC (TCTGCAGACA GTCTGGGACT CCCTAATGTG CATTATTAAA ATTA-CAGGCA ATTTACTTGG CTGATATGAG AACAGATAGT TCTGAAGTCA TCAATAATTT TCTGCTGTGT CTGAC-CAGCG TT) (SEQ ID NO: 29). Positive ES cell clones were then used to implant female mice using the VELOCI-MOUSE® method (described below) to generate a litter of pups containing a replacement of exons 7 to 9 of the endogenous Na$_v$1.7 locus with the corresponding exons from the human Na$_v$1.7 locus.

Targeted ES cells described above were used as donor ES cells and introduced into an 8-cell stage mouse embryo by the VELOCIMOUSE® method (supra). Mice bearing the humanization of exons 7 to 9 of the endogenous Na$_v$1.7 locus were identified by genotyping using a modification of allele assay (Valenzuela et al., supra) that detected the presence of the human Na$_v$1.7 sequences.

Mice bearing the humanized DI/S5-S6 in the endogenous Na$_v$1.7 locus can be bred to a Cre deletor mouse strain (see, e.g., International Patent Application Publication No. WO 2009/114400) in order to remove any loxed neomycin cassette introduced by the targeting vector that is not removed, e.g., at the ES cell stage or in the embryo. Optionally, the neomycin cassette is retained in the mice.

Pups are genotyped and a pup heterozygous for the humanized DI/S5-S6 in the endogenous Na$_v$1.7 locus is selected for characterizing Na$_v$1.7 DI/S5-S6 humanization.

Example IV

Humanization of the Extracellular Loop of Transmembrane Segments 5 to 6 in Domain III of an Endogenous Na$_v$1.7 Locus A targeting vector for humanization of the extracellular pore loop connecting transmembrane segments 5 and 6 of Domain III (DIII/S5-S6) was constructed by polymerase chain reaction (PCR) using mouse BAC clone BMQ-311E20 and human BAC clone RP11-746P5 (FIG. 5). Exons 23 to 25 of the human Na$_v$1.7 locus were amplified from human BAC clone RP11-746P5. A neomycin cassette flanked by loxP sites was ligated to the 3' end of the 2.8 kb PCR fragment (FIG. 5, middle). This ligated DNA fragment containing exons 23 to 25 of the human Na$_v$1.7 locus and the neomycin cassette was used to replace a 2.4 kb section of the endogenous mouse Na$_v$1.7 locus containing exons 23 to 25 in the mouse BAC clone BMQ-311E20 (FIG. 5).

Upstream and downstream homology arms were derived from mouse BAC DNA at positions 5' and 3' of exons 23 and 25, respectively, and added to the human DNA fragment-neomycin cassette to create the final targeting vector for humanization of DIII/S5-S6 of the endogenous Na$_v$1.7 locus which contained from 5' to 3' a 5' homology arm containing 21 kb of mouse DNA 5' of exon 23 of the endogenous Na$_v$1.7 locus, a 2.8 kb DNA fragment containing exons 23 to 25 of the human Na$_v$1.7 locus, a neomycin cassette flanked by loxP sites, and a 3' homology arm containing 108 kb of mouse DNA 3' of exon 25 of the endogenous Na$_v$1.7 locus. The targeting vector was linearized by digesting with NotI and then used in homologous recombination in bacterial cells to achieve a targeted replacement of exons 23 to 25 in endogenous Na$_v$1.7 locus with exons 23 to 25 of the human Na$_v$1.7 locus (FIG. 5, bottom).

The targeted BAC DNA (described above) was used to electroporate mouse ES cells to created modified ES cells comprising a replacement of exons 23 to 25 in the endogenous mouse Na$_v$1.7 locus with a genomic fragment comprising exons 23 to 25 of a human Na$_v$1.7 locus. Positive ES cells containing a genomic fragment comprising exons 23 to 25 of a human Na$_v$1.7 gene were identified by the quantitative PCR assay using TAQMAN® probes (Lie and Petropoulos, supra). The upstream region outside of the modified region of the endogenous locus were confirmed by PCR using primers 892TUPF (GCTTGGGCTT GCACCTTTA; SEQ ID NO: 30) and 892TUPR (TGCGTTGACC ACTACCTGAT AC; SEQ ID NO: 31) and probe 892TUPP (TCTGCATTGG CGTCT-GTTTG TCA; SEQ ID NO: 32), whereas the downstream region outside the modified region of the endogenous locus was confirmed with primers 892TDP3F (TGACTTGCCC TATCAATCTG AGATC; SEQ ID NO: 33) and 892TDP3R (GCTCACACTG TATACACACA AAATCTTC; SEQ ID NO: 34) and probe 892TDP3P (TCACTGCCTA TGATAAAGT; SEQ ID NO: 35). The presence of the neomycin cassette from the targeting vector was confirmed using the same primers and probe as described in Example 1. The insertion of exons 23 to 25 of the human Na$_v$1.7 gene was confirmed by PCR using primers 892HF (CACGGTTTCC TGCAAGTCAA; SEQ ID NO: 36) and 892HR (GGGA-CACTTA CAACTTGAAG CA; SEQ ID NO: 37) and probe 892HP (TCGTTCCGAA TGTTTTGCCC TTATGA; SEQ ID NO: 38). The nucleotide sequence across the upstream insertion point included the following, which indicates mouse genomic sequence upstream of exon 23 of the endogenous $Na_V1.7$ locus (contained within the parentheses below) linked contiguously to human $Na_V1.7$ genomic sequence present at the insertion point: (TTTCATTTAT TTGAAGTGCA ATAT-CATCTT GGCCATCTAC TCCTCTGTAT GCTAGTAG) GTAAGCCTGG TGATCACAGA (SEQ ID NO: 39). The nucleotide sequence across the downstream insertion point at the 5' end of the neomycin cassette included the following, which indicates human $Na_V1.7$ genomic sequence contiguous with cassette sequence downstream of the insertion point (contained within the parentheses below): GACTAGTATA CAATTACAAA TATGC (CTCGAGATAA CTTCGTATAA TGTATGCTAT ACGAAGTTAT) (SEQ ID NO: 40). The nucleotide sequence across the downstream insertion point at the 3' end of the neomycin cassette included the following, which indicates cassette sequence contiguous with mouse genomic sequence 3' of exon 25 of the endogenous $Na_V1.7$ locus (contained within the parentheses below): TATAC-GAAGT TATGCTAGC (TTTCCTGCTA ACCATCATTC TGGGGTATGT GTTATGATGG AAGTTAAGTG ACAGT-TACTT ATAATATGGC TGCT) (SEQ ID NO: 41). Positive ES cell clones were then used to implant female mice using the VELOCIMOUSE® method (described below) to generate a litter of pups containing a replacement of exons 23 to 25 of the endogenous $Na_V1.7$ locus with the corresponding exons from the human $Na_V1.7$ locus.

Mice containing a humanization of exons 23 to 25 in the endogenous $Na_V1.7$ locus with the human $Na_V1.7$-DIII/S5-S6 targeting vector were generated through electroporation of a targeted BAC DNA (described above) into mouse ES cells. Positive ES cells clones were confirmed by Taqman™ screening and karyotyping. Positive ES cell clones were then used to implant female mice using the VELOCIMOUSE® method (described below) to generate a litter of pups containing a humanization of exons 23 to 25 in the endogenous $Na_V1.7$ locus.

Targeted ES cells described above were used as donor ES cells and introduced into an 8-cell stage mouse embryo by the VELOCIMOUSE® method (see, e.g., U.S. Pat. No. 7,294, 754 and Poueymirou et al., supra). Mice bearing the humanization of exons 23 to 25 of the endogenous $Na_V1.7$ locus were identified by genotyping using a modification of allele assay (Valenzuela et al., supra) that detected the presence of the human $Na_V1.7$ sequences.

Mice bearing the humanized DIII/S5-S6 in the endogenous $Na_V1.7$ locus can be bred to a Cre deleter mouse strain (see, e.g., International Patent Application Publication No. WO 2009/114400) in order to remove any loxed neomycin cassette introduced by the targeting vector that is not removed, e.g., at the ES cell stage or in the embryo. Optionally, the neomycin cassette is retained in the mice.

Pups are genotyped and a pup heterozygous for the humanized DIII/S5-S6 in the endogenous $Na_V1.7$ locus is selected for characterizing $Na_V1.7$ DIII/S5-S6 humanization.

Example V

Behavioral Phenotyping of Humanized $Na_V1.7$ Mice

Current methods for studying the effects of pharmacological manipulation of human $Na_V1.7$ rely on transfected cells that are cultured in vitro. These cells that are engineered to express human $Na_V1.7$ protein lack auxiliary proteins and might not be fully representative of the mechanisms by which human $Na_V1.7$ functions in vivo. Thus, mice engineered to express human $Na_V1.7$ or a chimeric $Na_V1.7$ having a humanized extracellular pore loop as described in Examples 2-4 were generated and analyzed to understand the function of $Na_V1.7$ in vivo.

Figure 6A:
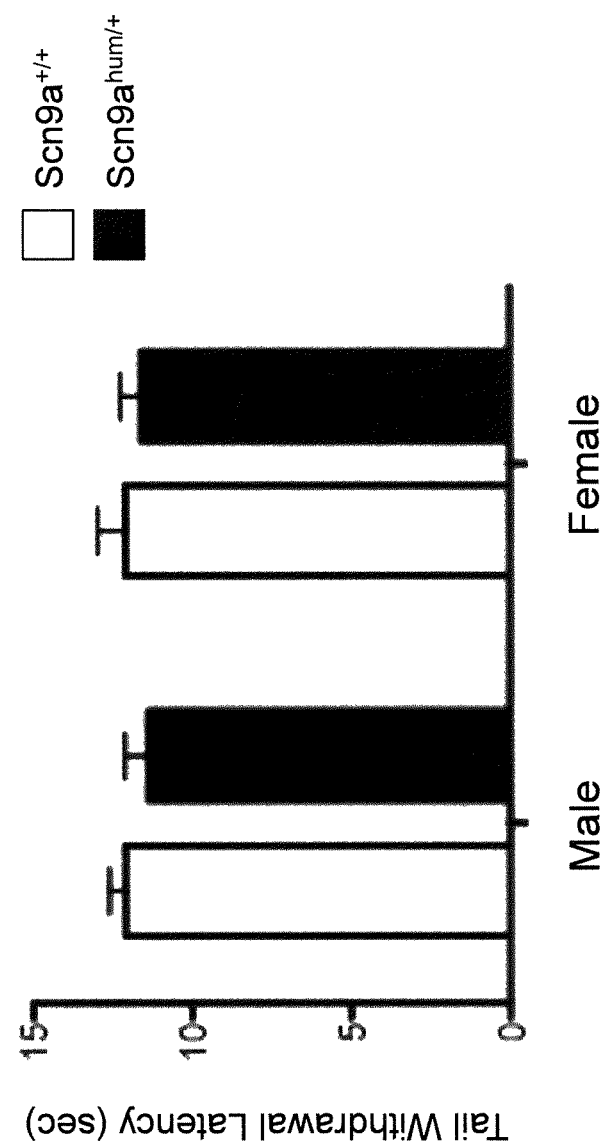
FIG. 6A shows the tail withdrawal latency (in seconds) in response to a nociceptive simulus (tail flick) in male and female cohorts of wild type ($Scn9A^{+/+}$) and mice heterozygous for a full length human $Na_V1.7$ gene ($Scn9A^{hum/+}$).
Figure 6B:
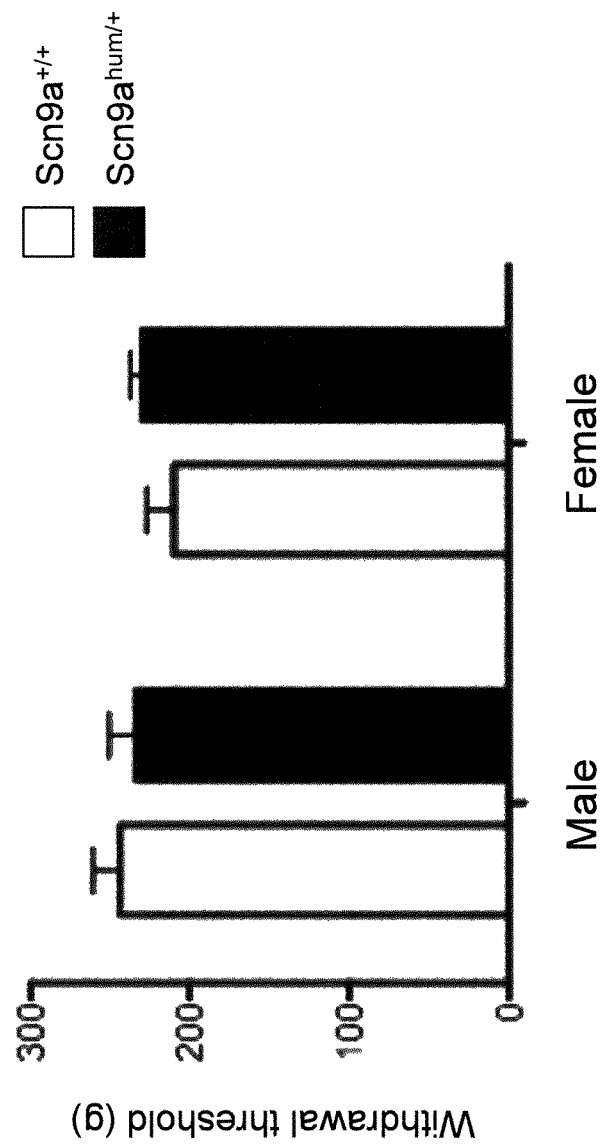
FIG. 6B shows the withdrawal threshold (in grams) in response to a nociceptive simulus (tail pinch) in male and female cohorts of wild type ($Scn9A^{+/+}$) and mice heterozygous for a full length human $Na_V1.7$ gene ($Scn9A^{hum/+}$).
Figure 6C:
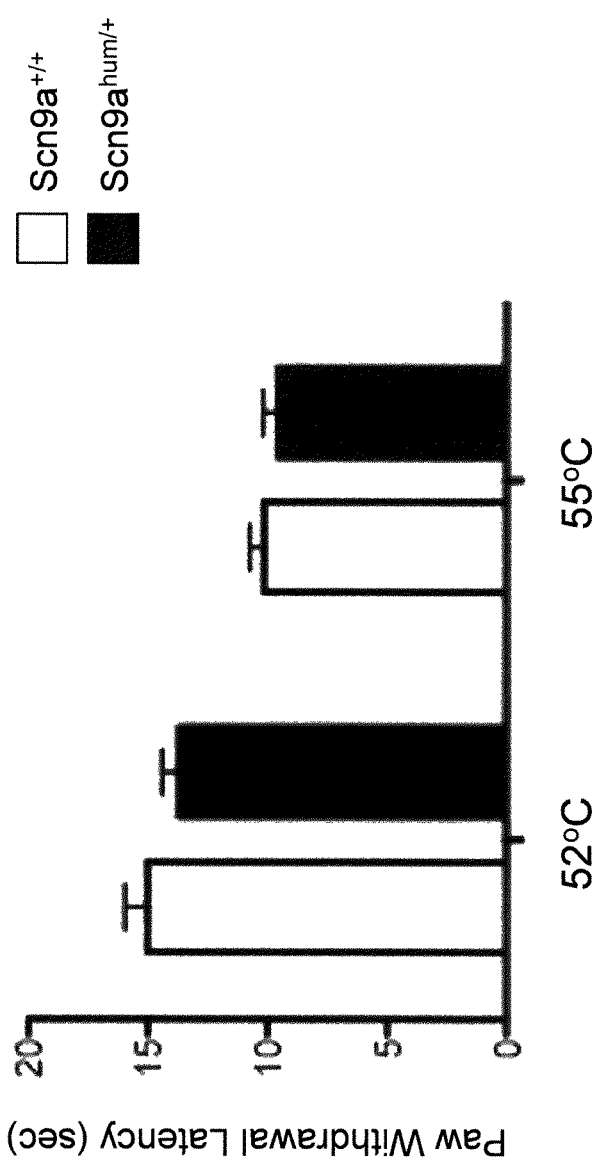
FIG. 6C shows the paw withdrawal latency (in seconds) in response to a nociceptive simulus (52° C. and 55° C. hot plate) in cohorts of wild type ($Scn9A^{+/+}$) and mice heterozygous for a full length human $Na_V1.7$ gene ($Scn9A^{hum/+}$).
Figure 7A:
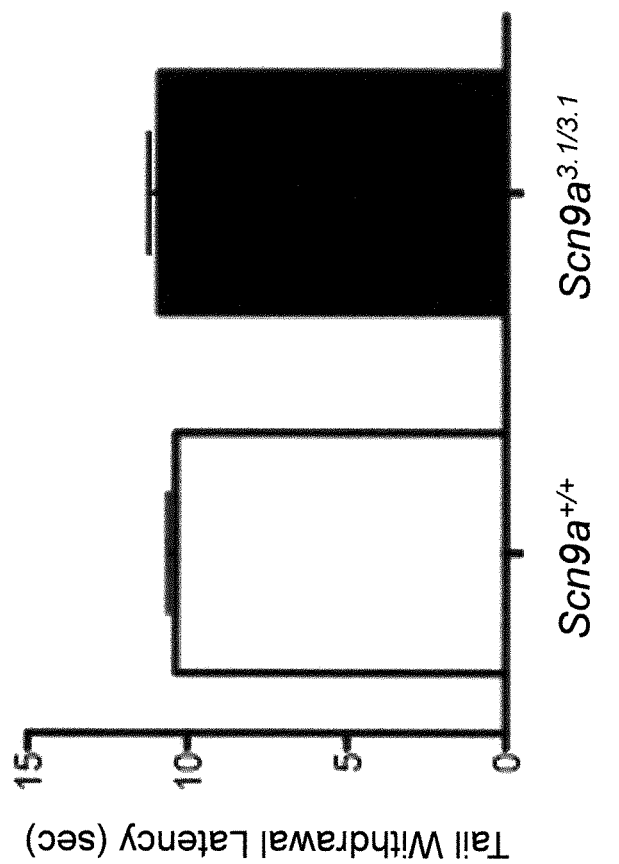
FIG. 7A shows the tail withdrawal latency (in seconds) in response to a nociceptive simulus (tail flick) in female cohorts of wild type ($Scn9A^{+/+}$) and mice homozygous for chimeric $Na_V1.7$ gene containing a human extracellular pore loop connecting transmembrane segments 5 and 6 of Domain I ($Scn9A^{3.1/3.1}$).
Figure 7B:
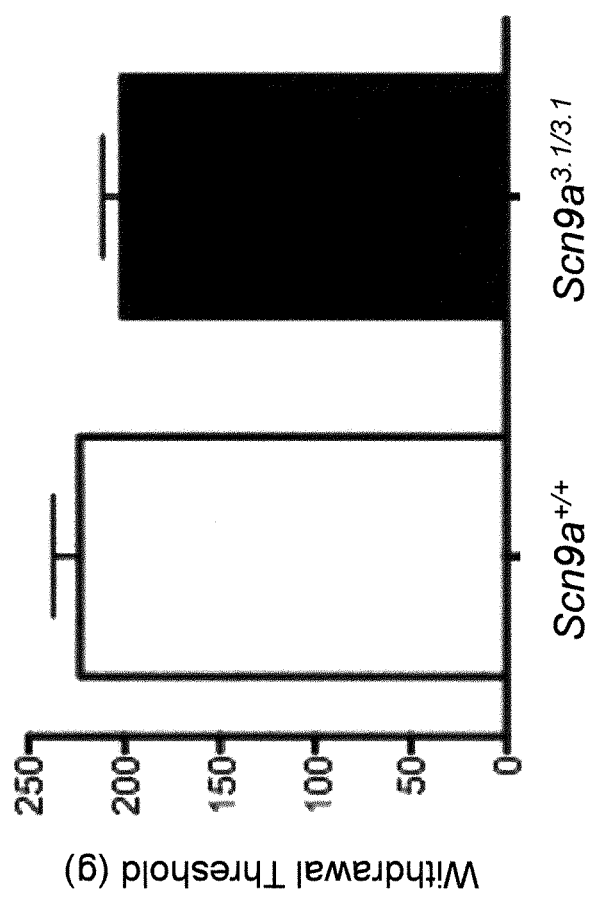
FIG. 7B shows the withdrawal threshold (in grams) in response to a nociceptive simulus (tail pinch) in female cohorts of wild type ($Scn9A^{+/+}$) and mice homozygous for chimeric $Na_V1.7$ gene containing a human extracellular pore loop connecting transmembrane segments 5 and 6 of Domain I ($Scn9A^{3.1/3.1}$).
Figure 7C:
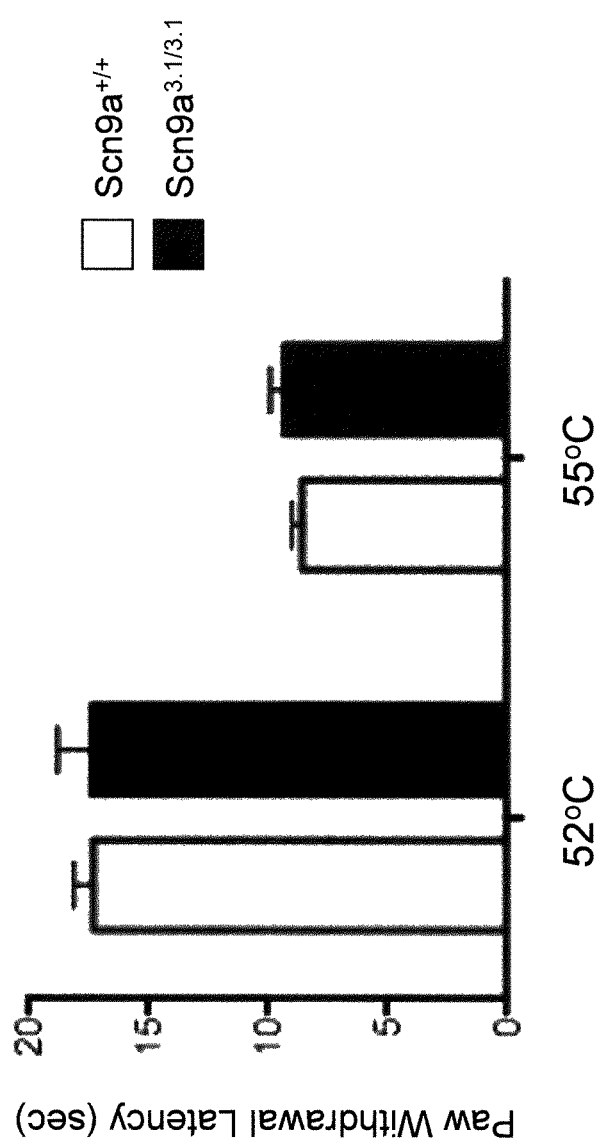
FIG. 7C shows the paw withdrawal latency (in seconds) in response to a nociceptive simulus (52° C. and 55° C. hot plate) in female cohorts of wild type ($Scn9A^{+/+}$) and mice homozygous for chimeric $Na_V1.7$ gene containing a human extracellular pore loop connecting transmembrane segments 5 and 6 of Domain I ($Scn9A^{3.1/3.1}$).
Figure 7D:
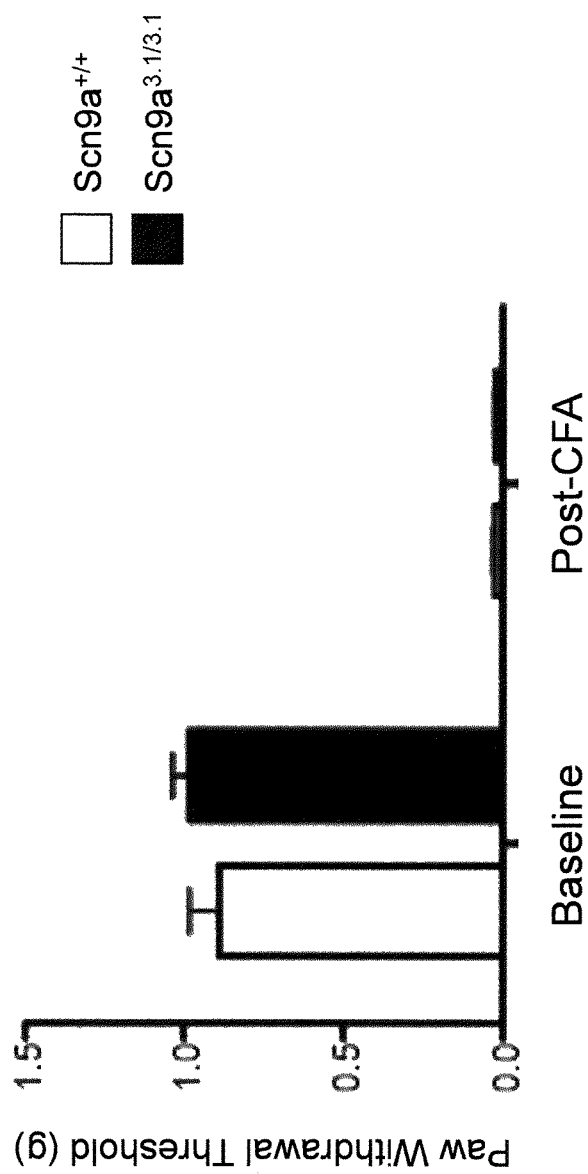
FIG. 7D shows mechanical allodynia measured as paw withdrawal threshold (in grams) before (baseline) and after (Post-CFA) administration of Complete Freund's Adjuvant in female cohorts of wild type ($Scn9A^{+/+}$) and mice homozygous for chimeric $Na_V1.7$ gene containing a human extracellular pore loop connecting transmembrane segments 5 and 6 of Domain I ($Scn9A^{3.1/3.1}$).
Figure 7E:
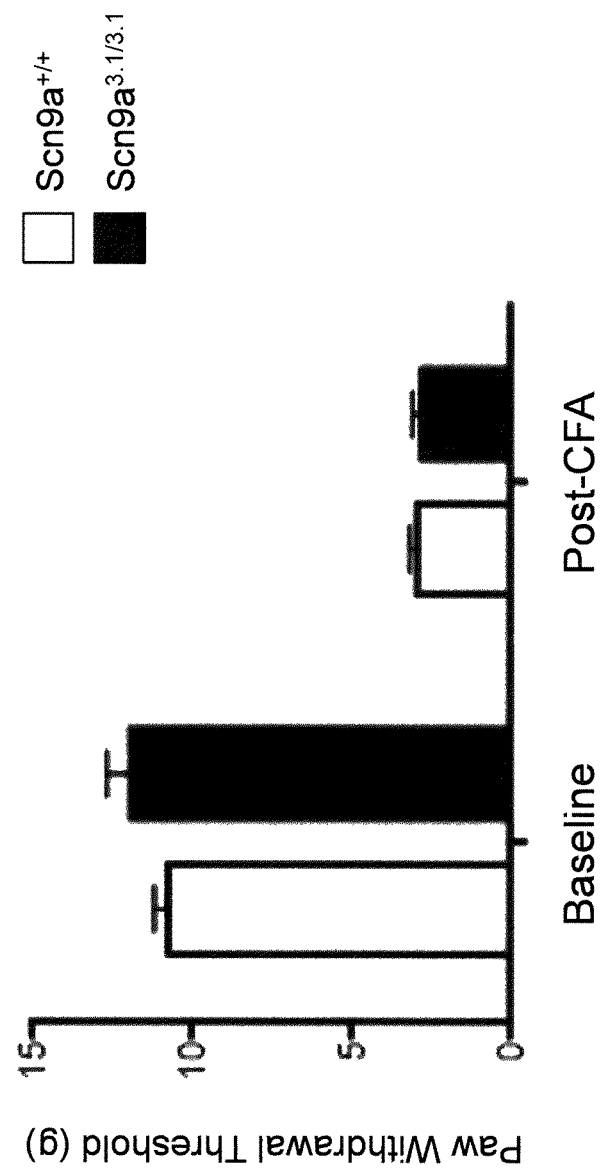
FIG. 7E shows thermal hyperalgesia measured as paw withdrawal threshold (in grams) before (baseline) and after (Post-CFA) administration of Complete Freund's Adjuvant in female cohorts of wild type ($Scn9A^{+/+}$) and mice homozygous for chimeric $Na_V1.7$ gene containing a human extracellular pore loop connecting transmembrane segments 5 and 6 of Domain I ($Scn9A^{3.1/3.1}$).
Figure 7F:
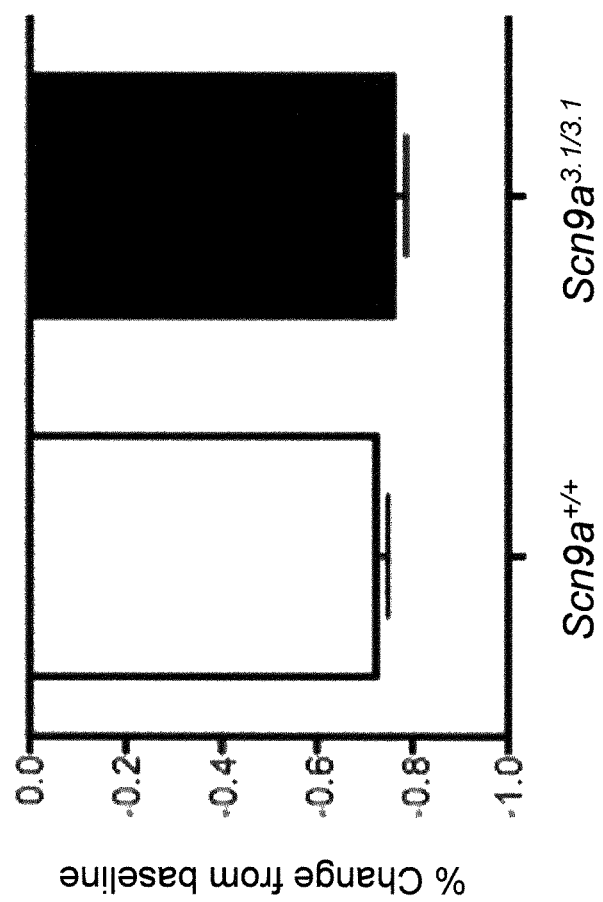
FIG. 7F shows the percent change from baseline in response to nociceptive stimuli in female cohorts of wild type ($Scn9A^{+/+}$) and mice homozygous for chimeric $Na_V1.7$ gene containing a human extracellular pore loop connecting transmembrane segments 5 and 6 of Domain I ($Scn9A^{3.1/3.1}$).

Briefly, two groups (n=6/6 each; male/female at 10-20 weeks) of mice, wild type ($Scn9a^{+/+}$) and mice heterozygous for a replacement of a mouse $Na_V1.7$ gene with a human $Na_V1.7$ gene ($Scn9a^{hum/+}$), were each subjected to a variety of nocifensive stimuli (hot plate thermal, tail flick thermal and noxious mechanical pressure). Results are shown in FIGS. 6A-6C.

In a similar experiment, two groups (n=10 each; female at 10-20 weeks) of mice, wild type ($Scn9a^{+/+}$) and mice homozygous for a chimeric $Na_V1.7$ gene that contains a human sequence that encodes an extracellular pore loop (DI/S5-S6; $Scn9a^{3.1/3.1}$), were each subjected to a variety of nocifensive stimuli (hot plate thermal, tail flick thermal, noxious mechanical, and inflammatory hypernociception using Complete Freund's Adjuvant). Results are shown in FIGS. 7A-7D.

No significant difference in any of the acute endpoints between $Scn9a^{+/+}$ and $Scn9a^{hum/+}$ or $Scn9a^{+/+}$ and $Scn9a^{3.1/3.1}$ mice was observed. These results demonstrate that humanized mice containing either a full-length human $Na_V1.7$ gene in place of the endogenous gene (as described in Example 2) or a human sequence that encodes an extracellular pore loop (as described in Example 3) display normal nociceptive behaviors in response to nocifensive stimuli as compared to wild-type control mice.

As shown in this Example, mice engineered to express complete or partially human $Na_V1.7$ protein on the surface of neurons respond to nociceptive stimuli in a similar fashion as compared to wild type and thus provide a platform for identifying antagonists of the α-subunit of $Na_V1.7$ and/or a particular extracellular pore loop. Such antagonists may be useful in blocking specific functions and associated neuronal activities in the treatment of several clinical pain syndromes.

Example VI

Identification and Function of DRG in Humanized $Na_V1.7$ Mice

Human antibodies specific for human $Na_V1.7$ were generated and analyzed for binding to neuronal cells isolated from the humanized $Na_V1.7$ mice described in Examples 2-4.

Briefly, VELOCIMMUNE® mice (U.S. Pat. No. 6,596, 541) were administered human $Na_V1.7$ ($hNa_V1.7$) antigen with adjuvant (e.g. complete or incomplete Freund's adjuvant, MPL+TDM adjuvant system (Sigma), or RIBI (muramyl dipeptides) (see O'Hagan 2000 Vaccine Adjuvant, by Human Press, Totowa, N.J.)). The immune response was monitored and antibodies containing human variable regions and mouse constant regions were isolated from hybridoma cell lines made from antibody-expressing B cells harvested from immunized mice. Alternatively, antigen-specific hybridoma cells may be isolated by flow cytometry. Antibodies specific to $hNa_V1.7$ may also be identified via direct isolation of splenocytes (e.g. see U.S. Pat. No. 7,582,298). Several anti-$hNa_V1.7$ antibodies were obtained by the foregoing methods and HEK293 cells engineered to stably express human $Na_V1.7$ or human $Na_V1.5$ were used to identify antibodies that specifically bind to $Na_V1.7$ but not to $Na_V1.5$ as determined by flow cytometry.

Selected anti-$hNa_V1.7$ antibodies were tested to determine their ability to block electrophysiological function (e.g. current, ion flux, etc.) of the $Na_V1.7$ channel using the ION-WORKS QUATTRO™ system (IWQ, Molecular Devices), the Port-a-Patch® system (Nanion Technologies) and QPatch system (Sophion Bioscience). Table 1 sets forth the average percent inhibition for five selected anti-hNa$_V$1.7 antibodies: less than 15% (−), 15-30% (+), greater than 30% (++). nd: not determined.

TABLE 1

| Antibody | IWQ (222 nM) | Port-a-Patch (50 nM) | QPatch (100 nM) |
|---|---|---|---|
| Ab1 | ++ | ++ | + |
| Ab2 | ++ | nd | + |
| Ab3 | ++ | ++ | + |
| Ab4 | ++ | + | + |
| Ab5 | − | + | + |

Immunohistochemistry.

Pain processing is the result of complex interactions among several proteins, receptors and channels that are expressed in dorsal root ganglion (DRG) nociceptive neurons. Selected anti-hNa$_V$1.7 antibodies were evaluated for binding to DRG neurons harvested from mice engineered to express human Na$_V$1.7 (Scn9a$^{hum/+}$, Example 2), mice engineered to express a chimeric Na$_V$1.7 containing a human extracellular pore loop (Scn9a$^{3.1/3.1}$, Example 3) and wild type mice (Scn9a$^{+/+}$).

Briefly, harvested lumbar DRGs from Scn9a$^{hum/+}$, Scn9a$^{3.1/3.1}$ and Scn9a$^{+/+}$ mice and Scn9a$^{+/+}$ rats (rScn9a$^{+/+}$) were dissociated and plated at a density of 5.5×10$^4$ cells/well on 96 well plates treated with poly-DL-ornithine (0.1 mg/mL) and laminin (5 μg/mL) followed by incubation at 37° C. in 96.5% air and 3.5% CO$_2$. Neurons were maintained in culture for 3 to 8 days in DMEM supplemented with 50 ng/mL nerve growth factor, 100 U/mL penicillin/streptomycin, MEM vitamins, and 10% heat-inactivated fetal calf serum. Plated cells were then fixed in 4% PFA and 4% sucrose in PBS pH7.2 for 30 minutes. Cells were then washed in PBS followed by blocking in 20% normal goat serum for one hour at room temperature. Neurons were then permeabilized in 10% normal goat serum with 0.1% Triton X-100 before immunostaining to confirm binding activity to a human or chimeric Na$_V$1.7 (or mouse and/or rat) on the cell surface of the DRG neurons. Table 2 sets forth the species-specific binding (+) or no binding (−) to DRG neurons for selected anti-NaV1.7 antibodies.

TABLE 2

| | DRG Genotype | | | |
|---|---|---|---|---|
| Antibody | Scn9a$^{hum/+}$ | Scn9a$^{3.1/3.1}$ | Scn9a$^{+/+}$ | rScn9a$^{+/+}$ |
| Ab1 | − | | − | − |
| Ab2 | | | + | − |
| Ab3 | + | | − | +/− |
| Ab4 | + | + | + | + |
| Ab5 | +/− | | − | − |

Selected anti-hNa$_V$1.7 antibodies demonstrated binding to DRG neurons expressing a human Na$_V$1.7 protein (e.g., Ab3, Ab4, and Ab5), a chimeric Na$_V$1.7 protein (e.g., Ab4) or a mouse Na$_V$1.7 protein (e.g., Ab2) on the cell surface, while no binding to DRG neurons expressing a mouse or rat Na$_V$1.7 protein was observed for other antibodies (e.g., Ab1 and Ab5). Other anti-hNa$_V$1.7 antibodies demonstrated species cross-reactivity in that the antibodies showed binding to DRG neurons from humanized Na$_V$1.7 mice, wild type mice and rats (e.g., Ab3 and Ab4).

Calcitonin Gene-Related Peptide (CGRP) Release Assay.

The neuropeptide calcitonin gene-related peptide (CGRP) is released from peripheral and spinal terminals of peptidergic A- and C-fibers nociceptive neurons in response to stimuli. Neuropeptide release initiates neurogenic inflammation, degranulation of mast cells, and other inflammatory reactions, which results in hyperalgesia/pain sensation. Inflammatory mediators such as Prostanglin E2, Bradykinin, Serotonin, Histamine and Capsaicin directly sensitize and excite nociceptive DRG in vitro and in vivo thereby leading to CGRP release. Sensitized nociceptors display a lowered threshold of activation, increased spontaneous activity and an increased response to suprathreshold stimuli. Thus, sensitization of DRGs and firing of action potentials can be achieved in vitro with different inflammatory mediators resulting in the release of CGRP and thereby serve as a means to measure DRG nociceptive function. Primary nociceptor activation was determined in primary in vitro DRG cultures isolated from humanized Na$_V$1.7 and wild type mice by measurement of CGRP release using an enzyme immunoassay (EIA) kit (Cayman, distributed by SPIbio, France).

Figure 8:
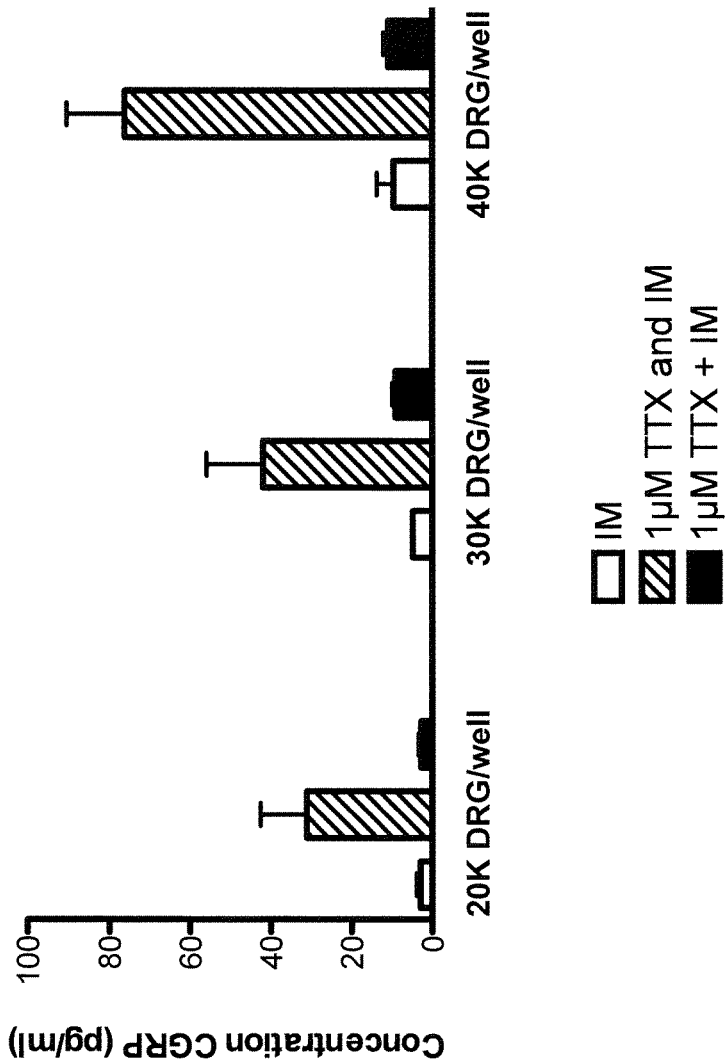
FIG. 8 shows the concentration (pg/mL) of calcitonin gene-related peptide (CGRP) released from three populations of dorsal root ganglia (DRG) isolated from wild type mice in response to exposure to an inflammatory mix (IM), 20 minute pre-incubation with 1 µM TTX followed by addition of an inflammatory mix (1 µM TTX and IM) or incubation with 1 µM TTX plus an inflammatory mix for 20 minutes (1 µM TTX+IM).

Briefly, DRGs between 3 to 8 days old were washed once in assay buffer and kept at 37° C. until addition of an inflammatory mix (e.g. 10 μM Prostanglin E2, 10 μM Bradykinin, and 1 μM Capsaicin). Two known inhibitors of Na$_V$ channels, Tetrodotoxin (TTX) and ProTx-II, were used to determine whether Na$_V$1.7 plays a role in an inflammatory mix induced-release of CGRP in vitro. TTX was tested at concentrations of 1 μM, an effective inhibitory concentration for TTX-sensitive channels, and 10 μM. ProTx-II largely inhibits Na$_V$1.7 at 10 nM (Schmalhofer, W. A, Calhoun, J., Burrows, R., Bailey, T., Kohler, M. G., Weinglass, A. B., Kaczorowski, G. J., Garcia, M. L., Koltzenburg, M., Priest, B. T. (2008) ProTx-II, a Selective Inhibitor of Na$_V$1.7 Sodium Channels, Blocks Action Potential Propagation in Nociceptors. Molecular Pharmacology 74(5):1476-1484). Neurons were incubated for 20 minutes with the inhibitor (TTX or ProTx-II), followed by stimulation with the inflammatory mix for 20 minutes or with the inhibitor combined with the inflammatory mix for 20 minutes. Compound dilutions were prepared in assay buffer and samples were added in duplicate onto a Human CGRP EIA plate and incubated overnight. Concentration of CGRP released by DRGs was measured the following day using an ELISA assay. Averages (mean+/−standard deviation) were calculated for each condition group. FIG. 8 shows the dose response for different concentrations of DRGs in the CGRP assays using TTX under the conditions mentioned above. The results for TTX are shown in Table 3. The results for ProTx-II are shown in Table 4. IM: inflammatory mix.

In a similar experiment, the role of Na$_V$1.7 in the TTX-potentiating release of CGRP in DRGs harvested from Scn9a$^{3.1/3.1}$ mice was tested using an amino amide-type local anesthetic (Lidocaine). This experiment was performed to confirm that the enhancement of CGRP release was not due to a non-specific effect of the toxins on DRG neurons. The results are shown in Table 5. IM: inflammatory mix.

In another similar experiment, selected anti-hNa$_V$1.7 antibodies were analyzed for their effect on in vitro CGRP release in DRG isolated from Scn9a$^{+/+}$, Scn9a$^{hum/+}$ and Scn9a$^{3.1/3.1}$ mice. The results are shown in Tables 6-9. IM: inflammatory mix.

As shown in this Example, when neurons (DRGs) expressing a wild type or chimeric Na$_V$1.7 protein on the cell surface are pre-incubated with known inhibitors of Na$_V$1.7 (TTX or ProTx-II, Table 3 or 4, respectively) or a non-Na$_V$1.7 specific local anesthetic (Lidocaine, Table 5), the inflammatory mix-induced release of CGRP is notably enhanced. However, when either a Na$_V$1.7 inhibitor or local anesthetic was added to the inflammatory mix prior exposure to the neurons, no enhancement of the inflammatory-induced release of CGRP was observed. Thus, these experiments show that inhibition of $Na_V1.7$ before stimulation with inflammatory mediators (Prostanglin $E_2$, Bradykinin, and Capsaicin) potentiates the release of CGRP in DRG neurons from wild type and humanized mice.

Further, when neurons (DRGs) are pre-incubated with an anti-h$Na_V1.7$ antibody, the inflammatory mix-induced release of CGRP is notably enhanced (Tables 6-9). These experiments demonstrate that the human and chimeric $Na_V1.7$ proteins expressed on the surface of DRGs in humanized mice are functional. This Example demonstrates that anti-h$Na_V1.7$ antibodies were able to mimic TTX-mediated enhancement of inflammatory mediator-induced CGRP release in DRG neurons from $Scn9a^{hum/+}$ and $Scn9a^{3.1/3.1}$ mice. Thus, the humanized $Na_V1.7$ mice ($Scn9a^{hum/+}$, $Scn9a^{3.1/3.1}$ and $Scn9a^{3.3/3.3}$) described herein provide a system for in vitro characterization of anti-h$Na_V1.7$ antibody binding and inhibition of channel function in vivo. Further, these mice represent an in vivo model system for the examination of new $Na_V1.7$-specific antagonists and evaluation of their therapeutic potential for treating responses mediated by $Na_V1.7$.

TABLE 3

CGRP Released from $Scn9a^{+/+}$ DRG Exposed to TTX

| Conditions | CGRP (pg/mL) |
| --- | --- |
| Buffer | 3 ± 1 |
| IM | 11 ± 1 |
| 1 µM TTX pre-incubation and IM | 76 ± 14 |
| 1 µM TTX + IM | 10 ± 4 |
| IM | 11 ± 4 |
| 10 µM TTX pre-incubation and IM | 44 ± 7 |

TABLE 4

CGRP Released from $Scn9a^{+/+}$ DRG Exposed to Pro-TxII

| Conditions | CGRP (pg/mL) |
| --- | --- |
| IM | 55 ± 5 |
| 10 nM Pro-TXII pre-incubation and IM | 186 ± 40 |
| 100 nM Pro-TXII pre-incubation and IM | 126 ± 25 |

TABLE 5

CGRP Released from $Scn9a^{3.1/3.1}$ DRG Exposed to Lidocaine

| Conditions | CGRP (pg/mL) |
| --- | --- |
| 5 mM Lidocaine preincubation and IM | 40 ± 6 |
| 5 mM Lidocaine + IM | 12 ± 1 |

TABLE 6

CGRP Released from $Scn9a^{+/+}$ DRG Exposed to anti-h$Na_V1.7$ antibody

| Conditions | CGRP (pg/mL) |
| --- | --- |
| IM | 172 ± 17 |
| Ab1 | 29 ± 4 |
| Ab1 pre-incubation and IM | 168 ± 11 |
| Ab2 | 35 ± 2 |
| Ab2 pre-incubation and IM | 522 ± 32 |
| Ab4 | 21 ± 5 |
| Ab4 pre-incubation and IM | 430 ± 2 |

TABLE 6-continued

CGRP Released from $Scn9a^{+/+}$ DRG Exposed to anti-h$Na_V1.7$ antibody

| Conditions | CGRP (pg/mL) |
| --- | --- |
| Ab5 | 39 ± 6 |
| Ab5 pre-incubation and IM | 62 ± 2 |

TABLE 7

CGRP Released from $Scn9a^{hum/+}$ DRG Exposed to anti-h$Na_V1.7$ antibody

| Conditions | CGRP (pg/mL) |
| --- | --- |
| Buffer | 2 ± 1 |
| IM | 21 ± 1 |
| Ab1 pre-incubation and IM | 97 ± 14 |
| Ab1 + IM | 19 ± 10 |
| Ab4 pre-incubation and IM | 122 ± 35 |
| Ab4 + IM | 26 ± 1 |
| Ab5 pre-incubation and IM | 82 ± 19 |
| Ab5 + IM | 20 ± 1 |

TABLE 8

CGRP Released from $Scn9a^{hum/+}$ DRG Exposed to anti-h$Na_V1.7$ antibody

| Conditions | CGRP (pg/mL) |
| --- | --- |
| IM | 30 ± 7 |
| Ab4 pre-incubation and IM | 81 ± 12 |
| Ab5 pre-incubation and IM | 117 ± 1 |

TABLE 9

CGRP Released from or $Scn9a^{3.1/3.1}$ DRG Exposed to anti-h$Na_V1.7$ antibody

| Conditions | CGRP (pg/mL) |
| --- | --- |
| IM | 27 ± 3 |
| Ab1 + IM | 12 ± 2 |
| Ab1 pre-incubation and IM | 38 ± 7 |
| Ab4 pre-incubation and IM | 101 ± 2 |
| Ab5 pre-incubation and IM | 47 ± 6 |

Example VII

Generation of Immortalized DRG Cell Lines from Humanized Mice

DRG neurons from humanized mice may be isolated and immortalized for continuous long-term study of human $Na_V1.7$ channel function in vitro.

DRG neurons can be immortalized by any method known in the art (e.g., see US 2009/0298095A1). Typically immortalizing isolated DRGs is accomplished by employing a vector of retroviral origin that has been engineered with DNA sequences encoding an oncogene (e.g. myc) and a selectable marker (e.g., neomycin). Suitable oncogenes that can be cloned into a vector for immortalizing an isolated DRG cell include growth factors or mitogens (e.g., c-Sis), receptor tyrosine kinases (e.g., epidermal growth factor receptor, platelet-derived growth factor receptor, and vascular endothelial growth factor receptor), cytoplasmic tyrosine kinases (e.g., Src-family, Syk-ZAP-70 family, and BTK family of tyrosine kinases), cytoplasmic serine/threonine kinases and their regulatory subunits (e.g., overexpression of Raf kinase and cyclin-dependent kinases), regulatory GTPases (e.g., Ras), and transcription factors (e.g., myc). Once the vector is constructed to harbor both DNA sequences such that they are capable of transcription within the cell, it can be used to create an immortalized DRG cell line by transfection into isolated DRGs from a humanized mouse as described in Examples 2-4.

Briefly, dissociated primary DRG neurons can be prepared by methods known in the art (e.g. see Wood J. N., Bevan, S. J., Coote, P. R., Dunn, P. M., Harmar, A. Hogan, P., Latchman, D. S., Morrison, C., Rougon, G., Theveniau, M., Wheatley, S. 1990. Novel Cell lines display properties of nociceptive sensory neurons. Proceedings of Biological Sciences, The Royal Society 241(1302):187-94; Raymond, H. K., Thode, S., Zhou, J., Friedman, G. C., Pardinas, J. R., Barrere, C., Johnson, R. M., Sah, D. W. Y. 1999. Immortalized human dorsal root ganglion cells differentiate into neurons with nociceptive properties. Journal of Neuroscience 19(13):5420-5428; Chen, W., Mi, R., Haughey, N., Oz, M., Höke, A. 2007. Immortalization and characterization of a nociceptive dorsal root ganglion sensory neuronal line. J of the Peripheral Nervous System 12:121-130). Cultures of isolated DRGs that express a human $Na_V1.7$ as described in Examples 2-4 are then transfected, e.g. by electroporation, with a candidate vector engineered as described above.

After transfection, cell cultures are grown in selection medium and maintained in the selection medium for up to 1-2 weeks until isolated colonies with 200-300 cells formed. Colonies are picked and expanded using standard culture methods when reached about 80-90% confluence. Cells from culture may be screened for expression of human $Na_V1.7$ protein by Southern or Western Blot using probes designed from the human $Na_V1.7$ sequence. Alternatively, confirmation of human $Na_V1.7$ channel protein in the transfected cells can be achieved by polymerase chain reaction on isolated DNA or RNA from the transfected cells.

Once the immortalized DRG neuronal cell line has demonstrated self-replication capability for multiple generations, it will be suitable for several different assays, including, for example, analysis of neuronal properties of the human $Na_V1.7$ channel, neuronal toxicity assays, measurement of DRG response to nociceptive stimuli, patch-clamp assays, high-throughput drug screening, and testing of $Na_V1.7$ specific blockers (e.g., an anti-NaV1.7 antibody).

---

What is claimed is:

1. A method for identifying a $Na_v1.7$ antagonist, comprising:
   (a) providing ex vivo a cell that expresses a full-length human $Na_v1.7$ α subunit protein, or a chimeric $Na_v1.7$ α subunit protein comprising an extracellular loop of domain I or III of the mouse $Na_v1.7$ α subunit that has been replaced by the corresponding loop from a human $Na_v1.7$ α subunit;
   (b) contacting the cell with a test compound that binds to, or blocks a function of, the human $Na_v1.7$ α subunit protein or the chimeric $Na_v1.7$ α subunit protein of (a) and waiting a first period of time;
   (c) contacting the cell from (b) with one or more inflammatory substances and waiting a second period of time;
   (d) determining the amount of calcitonin gene-related peptide (CGRP) released from the cell following step (c); and
   (e) comparing the amount of CGRP released in step (d) to the amount of CGRP released in the presence of a known sodium channel inhibitor, wherein an increase in CGRP released in the presence of a test compound indicates inhibition of $Na_v1.7$.

2. The method of claim 1, wherein the test compound is selected from an antibody, a peptide, an organic compound, and a toxin.

3. The method of claim 2, wherein the antibody is human.

4. The method of claim 1, wherein the one or more inflammatory substances are selected from prostaglandin $E_2$, bradykinin, capsaicin, protons, and a neurotrophic factor.

5. The method of claim 4, wherein the one or more inflammatory substances are prostaglandin $E_2$, bradykinin and capsaicin.

6. The method of claim 1, wherein the cell is a neuronal cell.

7. The method of claim 6, wherein the neuronal cell is a dorsal root ganglion cell (DRG).

8. The method of claim 6 or 7, wherein the cell is a mouse cell.

9. The method of claim 1, wherein the cell is isolated from a genetically modified mouse comprising, in its germline, a nucleotide sequence that encodes a human $Na_v1.7$α subunit or fragment thereof operably linked to a $Na_v$ promoter.

10. The method of claim 1, wherein the amount of CGRP released in the presence of the test compound inhibits one or more functions of the human or chimeric $Na_v1.7$ protein and is at least 2-fold higher than the known sodium channel inhibitor.

11. The method of claim 1, wherein the known sodium channel inhibitor is tetrodotoxin.

12. The method of claim 1, wherein the known sodium channel inhibitor is ProTx-II.

13. A method for identifying a $Na_v1.7$ antagonist, comprising:
   (a) contacting a DRG cell that expresses a full-length human $Na_v1.7$ α subunit protein, or a chimeric $Na_v1.7$ α subunit protein comprising an extracellular loop of domain I or III of the mouse $Na_v1.7$ α subunit that has been replaced by the corresponding loop from a human $Na_v1.7$ α subunit with a test compound that binds to, or blocks a function of, the human $Na_v1.7$ α subunit protein or the chimeric $Na_v1.7$ α subunit protein and waiting a first period of time;
   (b) contacting the DRG from (a) with one or more inflammatory substances and waiting a second period of time;
   (c) determining the amount of calcitonin gene-related peptide (CGRP) released from the DRG following step (b); and
   (d) comparing the amount of CGRP released in step (c) to the amount of CGRP released in the presence of a known sodium channel inhibitor, wherein an increase in CGRP released in the presence of a test compound indicates inhibition of $Na_v1.7$.

14. The method of claim 13, wherein the agent is selected from an antibody, a peptide, an organic compound, and a toxin.

15. The method of claim 14, wherein the antibody is human.

16. The method of claim 13, wherein the one or more inflammatory substances are prostaglandin $E_2$, bradykinin and capsaicin.

17. The method of claim 13, wherein the DRG is isolated from a member of the group consisting of human, mouse, rat, or monkey.

18. The method of claim 17, wherein the DRG is isolated from a mouse.

19. The method of claim 18, wherein the mouse comprises, in its germline, a nucleotide sequence that encodes a human $Na_v1.7$α subunit or fragment thereof operably linked to a $Na_v$ promoter.

20. The method of claim 13, wherein the known sodium channel inhibitor is tetrodotoxin.

21. The method of claim 13, wherein the known sodium channel inhibitor is ProTx-II.

22. A kit comprising a $Na_v1.7$ antagonist, a neuronal cell that expresses a full-length human $Na_v1.7$ α subunit protein or a chimeric $Na_v1.7$ α subunit protein comprising an extracellular pore loop sequence of the mouse $Na_v1.7$ α subunit that has been replaced by the corresponding extracellular pore loop sequence from a human $Na_v1.7$ α subunit, and one or more inflammatory substances.

23. The kit of claim 22, wherein the neuronal cell is a DRG cell.

24. The kit of claim 22, wherein the cell is immortalized.

25. The kit of claim 22, wherein the $Na_v1.7$ antagonist is an anti-$Na_v1.7$ antibody.

26. The kit of claim 22, wherein the human extracellular pore loop sequence corresponds to the extracellular pore loop sequence of domain I of a $Na_v1.7$ α subunit protein.

27. The kit of claim 22, wherein the human extracellular pore loop sequence corresponds to the extracellular pore loop sequence of domain III of a $Na_v1.7$ α subunit protein.

* * * * *

SEQUENCE LISTING

```
<160> NUMBER OF SEQ ID NOS: 43

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
gggacttctc tgggttcagt ta                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
aaaggctctc aatgggaaac aag                                             23

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
tcaatgactt gacataatgc atgcactcc                                       29

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
```

```
atgtcagcca atccttctaa agtg                                          24

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cgttttgcct aaggcggtac                                               20

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tcctatgagc ccatcacaac cacac                                         25

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
ggtggagagg ctattcggc                                                19

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
gaacacggcg gcatcag                                                  17

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
tgggcacaac agacaatcgg ctg                                           23

<210> SEQ ID NO 10
<211> LENGTH: 115
<212> TYPE: DNA
<213> ORGANISM: Artificial Sequence
<220> FEATURE:
<223> OTHER INFORMATION: Synthetic

<400> SEQUENCE: 10
ctagctgagc tgtcaccaca cattgctcct accacgtatt gtacagctac tgcaagagca   60
ccacagttgg ctttctgtat cataacttcg tataatgtat gctatacgaa gttat        115

<210> SEQ ID NO 11
<211> LENGTH: 148
```

```
<212> TYPE: DNA
<213> ORGANISM: Artificial Sequence
<220> FEATURE:
<223> OTHER INFORMATION: Synthetic

<400> SEQUENCE: 11
ataacttcgt ataatgtatg ctatacgaag ttatagcttc ggttttgata cactgtttac    60
agcctgcgaa ggtgactcac tcgtgttaat aagactcttt tacggaggtc tatgccaaac   120 tcttttatc aaatattctc aaaggcag                                       148

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
atcaaaggaa cccaaagaag                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gaagggcagc tgtttgccag                                                20

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
atgaagaagc cccaaagcca agca                                           24

<210> SEQ ID NO 15
<211> LENGTH: 17
<212> TYPE: DNA
<213> ORGANISM: Artificial Sequence
<220> FEATURE:
<223> OTHER INFORMATION: Synthetic

<400> SEQUENCE: 15
tgcggccgat cttagcc                                                   17

<210> SEQ ID NO 16
<211> LENGTH: 18
<212> TYPE: DNA
<213> ORGANISM: Artificial Sequence
<220> FEATURE:
<223> OTHER INFORMATION: Synthetic

<400> SEQUENCE: 16
ttgaccgatt ccttgcgg                                                  18

<210> SEQ ID NO 17
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 17
acgagcgggt cggcccatt c                                          21

<210> SEQ ID NO 18
<211> LENGTH: 99
<212> TYPE: DNA
<213> ORGANISM: Artificial Sequence
<220> FEATURE:
<223> OTHER INFORMATION: Synthetic

<400> SEQUENCE: 18
ttaggtaagg atccgaaggg gaaataaaac ctacaggatg agaagatggc aatgttgcct    60
cccccaggac ctcagagctt tgtccatttc acaaaacag                           99

<210> SEQ ID NO 19
<211> LENGTH: 87
<212> TYPE: DNA
<213> ORGANISM: Artificial Sequence
<220> FEATURE:
<223> OTHER INFORMATION: Synthetic

<400> SEQUENCE: 19
gtatgaataa aaaagcattg aaatagggat tcttgccaac ttgctctctc gagataactt    60
cgtataatgt atgctatacg aagttat                                        87

<210> SEQ ID NO 20
<211> LENGTH: 90
<212> TYPE: DNA
<213> ORGANISM: Artificial Sequence
<220> FEATURE:
<223> OTHER INFORMATION: Synthetic

<400> SEQUENCE: 20
tatacgaagt tatgctagta actataacgg tcctaaggta gcgagctagc agcttcggtt    60
ttgatacact gtttacagcc tgcgaaggtg                                     90

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggactacaac tgtttatggg caac                                           24

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
tcaattcttc ttcactctca gcag                                           24

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
```

```
tccggaagga ccttgagcag aatga                                              25

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
caacaggtga gcagcaacag                                                    20

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
gcaggagaca catacaccag ac                                                 22

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26
aaacacgcat gtctgaaggc agtcgg                                             26

<210> SEQ ID NO 27
<211> LENGTH: 201
<212> TYPE: DNA
<213> ORGANISM: Artificial Sequence
<220> FEATURE:
<223> OTHER INFORMATION: Synthetic

<400> SEQUENCE: 27
tacattttaa ggactaaaaa ccatcgtggg ggccctgatc caatcagtga agaagctctc        60
tgacgtcatg atcctcactg tgttctgtct cagtgtgttc gcactaattg gactacagct       120
gttcatggga aacctgaagc ataaatgttt tcgaaattca cttgaaaata atgaaacatt       180
agaaagcata atgaataccc t                                                 201

<210> SEQ ID NO 28
<211> LENGTH: 157
<212> TYPE: DNA
<213> ORGANISM: Artificial Sequence
<220> FEATURE:
<223> OTHER INFORMATION: Synthetic

<400> SEQUENCE: 28
aggtgagtac caagagaaac atgcattgta tttttgaatg gcatatgtac ctggtgtatg        60
ttaagagcct gtattaggag gttttttatt tatttgagaa tggaggaaac tctattactc       120
gagataactt cgtataatgt atgctatacg aagttat                                157

<210> SEQ ID NO 29
<211> LENGTH: 141
<212> TYPE: DNA
<213> ORGANISM: Artificial Sequence
<220> FEATURE:
<223> OTHER INFORMATION: Synthetic
```

```
<400> SEQUENCE: 29
tatacgaagt tatgctagct ctgcagacag tctgggactc cctaatgtgc attattaaaa      60
ttacaggcaa tttacttggc tgatatgaga acagatagtt ctgaagtcat caataatttt     120
ctgctgtgtc tgaccagcgt t                                                141

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
gcttgggctt gcacctttta                                                  19

<210> SEQ ID NO 31
<211> LENGTH: 22
<212> TYPE: DNA
<213> ORGANISM: Artificial Sequence
<220> FEATURE:
<223> OTHER INFORMATION: Synthetic

<400> SEQUENCE: 31
tgcgttgacc actacctgat ac                                               22

<210> SEQ ID NO 32
<211> LENGTH: 23
<212> TYPE: DNA
<213> ORGANISM: Artificial Sequence
<220> FEATURE:
<223> OTHER INFORMATION: Synthetic

<400> SEQUENCE: 32
tctgcattgg cgtctgtttg tca                                              23

<210> SEQ ID NO 33
<211> LENGTH: 25
<212> TYPE: DNA
<213> ORGANISM: Artificial Sequence
<220> FEATURE:
<223> OTHER INFORMATION: Synthetic

<400> SEQUENCE: 33
tgacttgccc tatcaatctg agatc                                            25

<210> SEQ ID NO 34
<211> LENGTH: 28
<212> TYPE: DNA
<213> ORGANISM: Artificial Sequence
<220> FEATURE:
<223> OTHER INFORMATION: Synthetic

<400> SEQUENCE: 34
gctcacactg tatacacaca aaatcttc                                         28

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
tcactgccta tgataaagt                                                   19
```

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
cacggtttcc tgcaagtcaa                                               20

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
gggacactta caacttgaag ca                                            22

<210> SEQ ID NO 38
<211> LENGTH: 26
<212> TYPE: DNA
<213> ORGANISM: Artificial Sequence
<220> FEATURE:
<223> OTHER INFORMATION: Synthetic

<400> SEQUENCE: 38
tcgttccgaa tgttttgccc ttatga                                        26

<210> SEQ ID NO 39
<211> LENGTH: 78
<212> TYPE: DNA
<213> ORGANISM: Artificial Sequence
<220> FEATURE:
<223> OTHER INFORMATION: Synthetic

<400> SEQUENCE: 39
tttcatttat ttgaagtgca atatcatctt ggccatctac tcctctgtat gctagtaggt   60
aagcctggtg atcacaga                                                 78

<210> SEQ ID NO 40
<211> LENGTH: 65
<212> TYPE: DNA
<213> ORGANISM: Artificial Sequence
<220> FEATURE:
<223> OTHER INFORMATION: Synthetic

<400> SEQUENCE: 40
gactagtata caattacaaa tatgcctcga gataacttcg tataatgtat gctatacgaa   60
gttat                                                               65

<210> SEQ ID NO 41
<211> LENGTH: 93
<212> TYPE: DNA
<213> ORGANISM: Artificial Sequence
<220> FEATURE:
<223> OTHER INFORMATION: Synthetic

<400> SEQUENCE: 41
tatacgaagt tatgctagct ttcctgctaa ccatcattct ggggtatgtg ttatgatgga   60
agttaagtga cagttactta taatatggct gct                                93

<210> SEQ ID NO 42
<211> LENGTH: 9771
<212> TYPE: DNA
<213> ORGANISM: Artificial Sequence
<220> FEATURE:
<223> OTHER INFORMATION: Synthetic

<400> SEQUENCE: 42

| | | | | | |
|---|---|---|---|---|---|
| cggggctgct | acctccacgg | gcgcgccctg | gcaggagggg | cgcagtctgc | ttgcaggcgg | 60 |
| tcgccagcgc | tccagcggcg | gctgtcggct | ttccaattcc | gccagctcgg | ctgaggctgg | 120 |
| gctagcctgg | gtgccagtgg | ctgctagcgg | caggcgtccc | ctgagcaaca | ggagcccaga | 180 |
| gaaaaagaag | cagccctgag | agagcgccgg | ggaaggagag | gcccgcgccc | tctcctggag | 240 |
| ccagattctg | caggtgcact | gggtggggat | gatcggcggg | ctaggttgca | agcctcttat | 300 |
| gtgaggagct | gaagaggaat | taaaatatac | aggatgaaaa | gatggcaatg | ttgcctcccc | 360 |
| caggacctca | gagctttgtc | catttcacaa | aacagtctct | tgccctcatt | gaacaacgca | 420 |
| ttgctgaaag | aaaatcaaag | gaacccaaag | aagaaaagaa | agatgatgat | gaagaagccc | 480 |
| caaagccaag | cagtgacttg | gaagctggca | aacagctgcc | cttcatctat | ggggacattc | 540 |
| ctcccggcat | ggtgtcagag | cccctggagg | acttggaccc | ctactatgca | gacaaaaaga | 600 |
| cttttcatagt | attgaacaaa | gggaaaacaa | tcttccgttt | caatgccaca | cctgctttat | 660 |
| atatgctttc | tcctttcagt | cctctaagaa | gaatatctat | taagatttta | gtacactcct | 720 |
| tattcagcat | gctcatcatg | tgcactattc | tgacaaactg | catatttatg | accatgaata | 780 |
| acccaccgga | ctggaccaaa | aatgtcgagt | acacttttac | tggaatatat | acttttgaat | 840 |
| cacttgtaaa | aatccttgca | agaggcttct | gtgtaggaga | attcactttt | cttcgtgacc | 900 |
| cgtggaactg | gctggatttt | gtcgtcattg | tttttgcgta | tttaacagaa | tttgtaaacc | 960 |
| taggcaatgt | ttcagctctt | cgaactttca | gagtattgag | agctttgaaa | actatttctg | 1020 |
| taatcccagg | cctgaagaca | attgtagggg | ctttgatcca | gtcagtgaag | aagctttctg | 1080 |
| atgtcatgat | cctgactgtg | ttctgtctga | gtgtgtttgc | actaattgga | ctacagctgt | 1140 |
| tcatgggaaa | cctgaagcat | aaatgttttc | gaaattcact | tgaaaataat | gaaacattag | 1200 |
| aaagcataat | gaatacccta | gagagtgaag | aagactttag | aaaatatttt | tattacttgg | 1260 |
| aaggatccaa | agatgctctc | ctttgtggtt | tcagcacaga | ttcaggtcag | tgtccagagg | 1320 |
| ggtacacctg | tgtgaaaatt | ggcagaaacc | ctgattatgg | ctacacgagc | tttgacactt | 1380 |
| tcagctgggc | cttcttagcc | ttgtttaggc | taatgaccca | agattactgg | gaaaaccttt | 1440 |
| accaacagac | gctgcgtgct | gctggcaaaa | cctacatgat | cttctttgtc | gtagtgattt | 1500 |
| tcctgggctc | ctttatcta | ataaacttga | tcctggctgt | ggttgccatg | gcatatgaag | 1560 |
| aacagaacca | ggcaaacatt | gaagaagcta | aacagaaaga | attagaattt | caacagatgt | 1620 |
| tagaccgtct | taaaaagag | caagaagaag | ctgaggcaat | tgcagcggca | gcggctgaat | 1680 |
| atacaagtat | taggagaagc | agaattatgg | gcctctcaga | gagttcttct | gaaacatcca | 1740 |
| aactgagctc | taaagtgct | aaagaagaa | gaaacagaag | aaagaaaaag | aatcaaaaga | 1800 |
| agctctccag | tggagaggaa | aagggagatg | ctgagaaatt | gtcgaaatca | gaatcagagg | 1860 |
| acagcatcag | aagaaaagt | ttccaccttg | gtgtcgaagg | gcataggcga | gcacatgaaa | 1920 |
| agaggttgtc | taccccaat | cagtcaccac | tcagcattcg | tggctccttg | ttttctgcaa | 1980 |
| ggcgaagcag | cagaacaagt | cttttagtt | tcaaaggcag | aggaagagat | ataggatctg | 2040 |
| agactgaatt | tgccgatgat | gagcacagca | ttttggaga | caatgagagc | agaagggcct | 2100 |
| cactgttgt | gccccacaga | ccccaggagc | gacgcagcag | taacatcagc | caagccagta | 2160 |

```
ggtccccacc aatgctgccg gtgaacggga aaatgcacag tgctgtggac tgcaacggtg    2220
tggtctccct ggttgatgga cgctcagccc tcatgctccc aatggacag cttctgccag     2280 agggcacgac caatcaaata cacaagaaaa ggcgttgtag ttcctatctc ctttcagagg    2340
atatgctgaa tgatcccaac ctcagacaga gagcaatgag tagagcaagc atattaacaa   2400
acactgtgga agaacttgaa gagtccagac aaaaatgtcc accttggtgg tacagatttg   2460
cacacaaatt cttgatctgg aattgctctc catattggat aaaattcaaa aagtgtatct   2520
attttattgt aatggatcct tttgtagatc ttgcaattac catttgcata gttttaaaca   2580
cattatttat ggctatggaa caccacccaa tgactgagga attcaaaaat gtacttgcta   2640
taggaaattt ggtctttact ggaatctttg cagctgaaat ggtattaaaa ctgattgcca   2700
tggatccata tgagtatttc caagtaggct ggaatatttt tgacagcctt attgtgactt   2760
taagtttagt ggagctcttt ctagcagatg tggaaggatt gtcagttctg cgatcattca   2820
gactgctccg agtcttcaag ttggcaaaat cctggccaac attgaacatg ctgattaaga   2880
tcattggtaa ctcagtaggg gctctaggta acctcacctt agtgttggcc atcatcgtct   2940 tcattttgc tgtggtcggc atgcagctct ttggtaagag ctacaaagaa tgtgtctgca   3000
agatcaatga tgactgtacg ctcccacggt ggcacatgaa cgacttcttc cactccttcc   3060
tgattgtgtt ccgcgtgctg tgtggagagt ggatagagac catgtgggac tgtatggagg   3120
tcgctggtca agctatgtgc cttattgttt acatgatggt catggtcatt ggaaacctgg   3180
tggtcctaaa cctatttctg gccttattat tgagctcatt tagttcagac aatcttacag   3240
caattgaaga agaccctgat gcaaacaacc tccagattgc agtgactaga attaaaaagg   3300
gaataaatta tgtgaaacaa accttacgtg aatttattct aaaagcattt tccaaaaagc   3360
caaagatttc cagggagata agacaagcag aagatctgaa tactaagaag gaaaactata   3420
tttctaacca tacacttgct gaaatgagca aaggtcacaa tttcctcaag gaaaagata   3480 aaatcagtgg ttttggaagc agcgtggaca acacttgat ggaagacagt gatggtcaat   3540
catttattca caatcccagc ctcacagtga cagtgccaat tgcacctggg gaatccgatt   3600
tggaaaatat gaatgctgag gaacttagca gtgattcgga tagtgaatac agcaaagtga   3660
gattaaaccg gtcaagctcc tcagagtgca gcacagttga taacccttg cctggagaag    3720 gagaagaagc agaggctgaa cctatgaatt ccgatgagcc agaggcctgt ttcacagatg   3780
gttgtgtacg gaggttctca tgctgccaag ttaacataga gtcagggaaa ggaaaaatct    3840
ggtggaacat caggaaaaacc tgctacaaga ttgttgaaca cagttggttt gaaagcttca   3900
ttgtcctcat gatcctgctc agcagtggtg ccctggcttt tgaagatatt tatattgaaa   3960
ggaaaaagac cattaagatt atcctggagt atgcagacaa gatcttcact tacatcttca   4020
ttctggaaat gcttctaaaa tggatagcat atggttataa aacatatttc accaatgcct   4080
ggtgttggct ggatttccta attgttgatg tttctttggt tactttagtg gcaaacactc   4140
ttggctactc agatcttggc cccattaaat cccttcggac actgagagct ttaagacctc   4200
taagagcctt atctagattt gaaggaatga gggtcgttgt gaatgcactc ataggagcaa   4260
ttccttccat catgaatgtg ctacttgtgt gtcttatatt ctggctgata ttcagcatca   4320
tgggagtaaa tttgtttgct ggcaagttct atgagtgtat taacaccaca gatgggtcac   4380
ggtttcctgc aagtcaagtt ccaaatcgtt ccgaatgttt tgcccttatg aatgttagtc   4440
aaaatgtgcg atggaaaaac ctgaaagtga actttgataa tgtcggactt ggttacctat   4500
ctctgcttca agttgcaact tttaagggat ggacgattat tatgtatgca gcagtggatt   4560
```

```
ctgttaatgt agacaagcag cccaaatatg aatatagcct ctacatgtat atttattttg   4620
tcgtctttat catctttggg tcattcttca ctttgaactt gttcattggt gtcatcatag   4680
ataatttcaa ccaacagaaa aagaagcttg gaggtcaaga catctttatg acagaagaac   4740
agaagaaata ctataatgca atgaaaaagc tggggtccaa gaagccacaa aagccaattc   4800
ctcgaccagg gaacaaaatc caaggatgta tatttgacct agtgacaaat caagcctttg   4860
atattagtat catggttctt atctgtctca acatggtaac catgatggta gaaaaggagg   4920
gtcaaagtca acatatgact gaagttttat attggataaa tgtggttttt ataatccttt   4980
tcactggaga atgtgtgcta aaactgatct ccctcagaca ctactacttc actgtaggat   5040
ggaatatttt tgattttgtg gttgtgatta tctccattgt aggtatgttt ctagctgatt   5100
tgattgaaac gtattttgtg tccctaccc tgttccgagt gatccgtctt gccaggattg    5160
gccgaatcct acgtctagtc aaaggagcaa aggggatccg cacgctgctc tttgctttga   5220
tgatgtccct tcctgcgttg tttaacatcg gcctcctgct cttcctggtc atgttcatct   5280
acgccatctt tggaatgtcc aactttgcct atgttaaaaa ggaagatgga attaatgaca   5340
tgttcaattt tgagaccttt ggcaacagta tgatttgcct gttccaaatt acaacctctg   5400
ctggctggga tggattgcta gcacctattc ttaacagtaa gccacccgac tgtgacccaa   5460
aaaaagttca tcctggaagt tcagttgaag gagactgtgg taacccatct gttgaatat    5520 tctactttgt tagttatatc atcatatcct tcctggttgt ggtgaacatg tacattgcag   5580
tcatactgga gaatttagt gttgccactg aagaaagtac tgaacctctg agtgaggatg    5640
actttgagat gttctatgag gtttgggaga gtttgatcc cgatgcgacc cagtttatag    5700
agttctctaa actctctgat tttgcagctg ccctggatcc tcctcttctc atagcaaaac   5760
ccaacaaagt ccagctcatt gccatggatc tgcccatggt tagtggtgac cggatccatt   5820
gtcttgacat cttatttgct tttacaaagc gtgttttggg tgagagtggg gagatggatt   5880
ctcttcgttc acagatggaa gaaaggttca tgtctgcaaa tccttccaaa gtgtcctatg   5940
aacccatcac aaccacacta aaacggaaac aagaggatgt gtctgctact gtcattcagc   6000
gtgcttatag acgttaccgc ttaaggcaaa atgtcaaaaa tatatcaagt atatacataa   6060
aagatggaga cagagatgat gatttactca ataaaaaaga tatggctttt gataatgtta   6120
atgagaactc aagtccagaa aaaacagatg ccacttcatc caccacctct ccaccttcat   6180
atgatagtgt aacaaagcca gacaaagaga aatatgaaca agacagaaca gaaaaggaag   6240
acaaagggaa agacagcaag gaaagcaaaa aatagagctt cattttgat atattgttta    6300 cagcctgtga aagtgattta tttgtgttaa taaaactctt ttgaggaagt ctatgccaaa   6360 atcctttta tcaaaatatt ctcgaaggca gtgcagtcac taactctgat ttcctaagaa    6420
aggtgggcag cattagcaga tggttatttt tgcactgatg attctttaag aatcgtaaga   6480
gaactctgta ggaattattg attatagcat acaaaagtga ttcagttttt tggtttttaa   6540
taaatcagaa gaccatgtag aaaacttta catctgcctt gtcatctttt cacaggattg    6600
taattagtct tgtttcccat gtaaataaac aacacacgca tacagaaaaa tctattattt   6660
atctattatt tggaaatcaa caaaagtatt tgccttggct ttgcaatgaa atgcttgata   6720
gaagtaatgg acattagtta tgaatgttta gttaaaatgc attattaggg agcttgactt   6780
tttatcaatg tacagaggtt attctatatt ttgaggtgct taaatttatt ctacattgca   6840
tcagaaccaa tttatatgtg cctataaaat gccatgggat taaaaatata tgtaggctat   6900
tcatttctac aaatgttttt cattcatctt gactcacatg ccaacaagga taagacttac   6960
```

```
ctttagagta ttgtgtttca tagcctttct tctttcatat cccttttttgt tcatagaata    7020 accacagaac ttgaaaaatt attctaagta catattacac tcctcaaaaa aaacaaagat    7080
aactgagaaa aaagttattg acagaagttc tatttgctat tatttacata gcctaacatt    7140
tgactgtgct gcccaaaata ctgataatag tctcttaaac tcttttgtca aatttttcctg   7200 ctttcttatg cagtattgtt tagtcatcct ttcgctgtaa gcaaagttga tgaaatcctt    7260
cctgatatgc agttagttgt tgaccacgg tacatacttg agcagataat aacttgggca    7320
cagtatttat tgcatcactt gtatacaatc ccgtgtttgg caagcttca aatcatgtaa     7380 tatgacagac tttacacaga tatgtgttta gtatgaataa aaaagcattg aaatagggat    7440
tcttgccaac ttgctctctt gccaccaact tactttccta aattatggaa gtaatctttt    7500
ttggatatac ttcaatgtat acaatgagga agatgtcacc ttctccttaa aattctatga    7560
tgtgaaatat attttgcctc aatcaacaca gtaccatggg cttctaattt atcaagcaca    7620
tattcatttt gcattagctg tagacatcta gttttttgaa aacacctatt aatagtaatt    7680
tgaaaagaaa taaccataat gcttttttc gtgagtttat ttcaggaata tgagatcttt     7740
cttctataaa gttattcatg cacaggcaaa aattgagcta cacaggtaga atgtagtttt    7800
acttagaaga ttttgtggg aggttttgaa gcaaatatat aaaacaactt tcactaattt     7860
gctttccata tttaaaaaat aataaattac atttatataa taaatgttta aagcacatat    7920
tttttgttgt tctggcaatt taaaagaaa gaggatttaa acgtacctat agaaacaaag     7980
atttatggtt aaagaatgag atcagaagtc tagaatgttt ttaaattgtg atatatttta    8040
caacatccgt tattactttg agacatttgt cctaatctac gtataaaact caatctaggg    8100
ctaaagattc tttataccat cttaggttca ttcatcttag gctatttgaa ccacttttta    8160
atttaatatg aaagacacca tgcagtgttt tccgagacta catagatcat tttatcacat    8220
acctaccaag cctgttggaa ataggttttg ataatttaag tagggaccta tacaaaatat    8280
attacattta tcagattttt aaatacattc aattaagaat ttaacatcac cttaaatttg    8340
aattcaatct accgttattt caaactcaca aatataactg cattatgaat acttacataa    8400
tgtagtaaga caagatgttt gacaggttcg tgtgtaattt tctattaatg ttttttacatt   8460 gccttgtttt tatgtaaaat aaaaaatatg ggcaactggt ttgttaacaa cacaatttct    8520
tcttagcatt tcaaaaatat atataaagtt gttctttttc ctatttcatg aactatgttt    8580
ttttttaaaa taacatggtt aagttttata tatatttacg tttgtttcag gaatgtctac    8640
ttgtgacttt ttatcaatta aaaataatat ttggaagaaa gagcttatta agtataagct    8700
tgaagtaaaa ttagacctct ctttccatgt agattactgt ttgtactgat ggtttcaccc    8760
ttcagaaggc actgtcatat taatatttaa attttataat cgctgaactt attacaccca    8820
acaatacaga aaggcagtta cactgaagaa cttaacttag aataaaatgg aagcaaacag    8880 gtttttctaaa aactttttta agtgaccagg tctcgctctg tcacccaggc tagagtgcaa   8940
tggcatgatc atagctctct gcagcctcaa ctctgggctc aagcaaccct cctgcctcag    9000
cctcccaagt agctaagact acaggtacat gccaccatgc ctggctaata tttaaatttt    9060
tgtagataag gggtcttgct atgttgccca ggctagtctc aaactcctgg cttcaagtgt    9120
tcctactgtc atgacctgcc aacatgctgg ggttacaggg atgagccacc atgcccaaa     9180 caggtttgaa cacaaatctt tcggatgaaa attagagaac ctaattttag cttttttgata   9240 gttacctagt ttgcaaaaga tttgggtgac ttgtgagctg ttttttaaatg ctgattgttg   9300 aacatcacaa cccaaaatac ttagcatgat tttatagagt tttgatagct ttattaaaaa    9360
```

```
gagtgaaaat aaaatgcata tgtaaataaa gcagttctaa atagctattt cagagaaatg    9420
ttaatagaag tgctgaaaga agggccaact aaattaggat ggccagggaa ttggcctggg    9480
tttaggacct atgtatgaag gccaccaatt ttttaaaaat atctgtggtt tattatgtta    9540
ttatcttctt gaggaaaaca atcaagaatt gcttcatgaa aataaataaa tagccatgaa    9600
tatcataaag ctgtttacat aggattcttt acaaatttca tagatctatg aatgctcaaa    9660
atgtttgagt ttgccataaa ttatattgta gttatattgt agttatactt gagactgaca    9720
cattgtaata taatctaaga ataaagtta tacaaaataa aaaaaaaaa a              9771
```

```
<210> SEQ ID NO 43
<211> LENGTH: 1977
<212> TYPE: PRT
<213> ORGANISM: Artificial Sequence
<220> FEATURE:
<223> OTHER INFORMATION: Synthetic

<400> SEQUENCE: 43
```

```
Met Ala Met Leu Pro Pro Gly Pro Gln Ser Phe Val His Phe Thr
 1               5                  10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
```

-continued

```
            290                 295                 300
Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                    325                 330                 335

Pro Asp Tyr Gly Tyr Thr Ser Phe Asp Thr Phe Ser Trp Ala Phe Leu
                340                 345                 350

Ala Leu Phe Arg Leu Met Thr Gln Asp Tyr Trp Glu Asn Leu Tyr Gln
                355                 360                 365

Gln Thr Leu Arg Ala Ala Gly Lys Thr Tyr Met Ile Phe Phe Val Val
370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
                420                 425                 430

Glu Gln Glu Glu Ala Glu Ala Ile Ala Ala Ala Ala Glu Tyr Thr
                435                 440                 445

Ser Ile Arg Arg Ser Arg Ile Met Gly Leu Ser Glu Ser Ser Ser Glu
450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
                500                 505                 510

Ser Phe His Leu Gly Val Glu Gly His Arg Arg Ala His Glu Lys Arg
                515                 520                 525

Leu Ser Thr Pro Asn Gln Ser Pro Leu Ser Ile Arg Gly Ser Leu Phe
530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
                580                 585                 590

Arg Pro Gln Glu Arg Arg Ser Ser Asn Ile Ser Gln Ala Ser Arg Ser
                595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
                675                 680                 685

Val Glu Glu Leu Glu Glu Ser Arg Gln Lys Cys Pro Pro Trp Trp Tyr
                690                 695                 700

Arg Phe Ala His Lys Phe Leu Ile Trp Asn Cys Ser Pro Tyr Trp Ile
705                 710                 715                 720
```

-continued

```
Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys Glu
    1010                1015                1020

Asn Tyr Ile Ser Asn His Thr Leu Ala Glu Met Ser Lys Gly His Asn
1025                1030                1035                1040

Phe Leu Lys Glu Lys Asp Lys Ile Ser Gly Phe Gly Ser Ser Val Asp
                1045                1050                1055

Lys His Leu Met Glu Asp Ser Asp Gly Gln Ser Phe Ile His Asn Pro
            1060                1065                1070

Ser Leu Thr Val Thr Val Pro Ile Ala Pro Gly Glu Ser Asp Leu Glu
        1075                1080                1085

Asn Met Asn Ala Glu Glu Leu Ser Ser Asp Ser Asp Ser Glu Tyr Ser
    1090                1095                1100

Lys Val Arg Leu Asn Arg Ser Ser Ser Ser Glu Cys Ser Thr Val Asp
1105                1110                1115                1120

Asn Pro Leu Pro Gly Glu Gly Glu Ala Glu Ala Glu Pro Met Asn
                1125                1130                1135

Ser Asp Glu Pro Glu Ala Cys Phe Thr Asp Gly Cys Val Arg Arg Phe
            1140                1145                1150
```

```
Ser Cys Cys Gln Val Asn Ile Glu Ser Gly Lys Gly Lys Ile Trp Trp
        1155                1160                1165

Asn Ile Arg Lys Thr Cys Tyr Lys Ile Val Glu His Ser Trp Phe Glu
    1170                1175                1180

Ser Phe Ile Val Leu Met Ile Leu Ser Ser Gly Ala Leu Ala Phe
1185                1190                1195                1200

Glu Asp Ile Tyr Ile Glu Arg Lys Lys Thr Ile Lys Ile Ile Leu Glu
            1205                1210                1215

Tyr Ala Asp Lys Ile Phe Thr Tyr Ile Phe Ile Leu Glu Met Leu Leu
        1220                1225                1230

Lys Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val Ala
1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
            1285                1290                1295

Arg Val Val Val Asn Ala Leu Ile Gly Ala Ile Pro Ser Ile Met Asn
                1300                1305                1310

Val Leu Leu Val Cys Leu Ile Phe Trp Leu Ile Phe Ser Ile Met Gly
        1315                1320                1325

Val Asn Leu Phe Ala Gly Lys Phe Tyr Glu Cys Ile Asn Thr Thr Asp
            1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
            1365                1370                1375

Asn Phe Asp Asn Val Gly Leu Gly Tyr Leu Ser Leu Leu Gln Val Ala
        1380                1385                1390

Thr Phe Lys Gly Trp Thr Ile Ile Met Tyr Ala Ala Val Asp Ser Val
    1395                1400                1405

Asn Val Asp Lys Gln Pro Lys Tyr Glu Tyr Ser Leu Tyr Met Tyr Ile
        1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
            1445                1450                1455

Gly Gly Gln Asp Ile Phe Met Thr Glu Glu Gln Lys Lys Tyr Tyr Asn
            1460                1465                1470

Ala Met Lys Lys Leu Gly Ser Lys Lys Pro Gln Lys Pro Ile Pro Arg
        1475                1480                1485

Pro Gly Asn Lys Ile Gln Gly Cys Ile Phe Asp Leu Val Thr Asn Gln
    1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
            1525                1530                1535

Tyr Trp Ile Asn Val Val Phe Ile Ile Leu Phe Thr Gly Glu Cys Val
        1540                1545                1550

Leu Lys Leu Ile Ser Leu Arg His Tyr Tyr Phe Thr Val Gly Trp Asn
    1555                1560                1565

Ile Phe Asp Phe Val Val Val Ile Ile Ser Ile Val Gly Met Phe Leu
```

-continued

```
              1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
              1605                1610                1615

Lys Gly Ile Arg Thr Leu Leu Phe Ala Leu Met Met Ser Leu Pro Ala
              1620                1625                1630

Leu Phe Asn Ile Gly Leu Leu Leu Phe Leu Val Met Phe Ile Tyr Ala
              1635                1640                1645

Ile Phe Gly Met Ser Asn Phe Ala Tyr Val Lys Lys Glu Asp Gly Ile
              1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
              1685                1690                1695

Leu Asn Ser Lys Pro Pro Asp Cys Asp Pro Lys Val His Pro Gly
              1700                1705                1710

Ser Ser Val Glu Gly Asp Cys Gly Asn Pro Ser Val Gly Ile Phe Tyr
              1715                1720                1725

Phe Val Ser Tyr Ile Ile Ile Ser Phe Leu Val Val Asn Met Tyr
              1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
              1765                1770                1775

Lys Phe Asp Pro Asp Ala Thr Gln Phe Ile Glu Phe Ser Lys Leu Ser
              1780                1785                1790

Asp Phe Ala Ala Ala Leu Asp Pro Pro Leu Leu Ile Ala Lys Pro Asn
              1795                1800                1805

Lys Val Gln Leu Ile Ala Met Asp Leu Pro Met Val Ser Gly Asp Arg
              1810                1815                1820

Ile His Cys Leu Asp Ile Leu Phe Ala Phe Thr Lys Arg Val Leu Gly
1825                1830                1835                1840

Glu Ser Gly Glu Met Asp Ser Leu Arg Ser Gln Met Glu Glu Arg Phe
              1845                1850                1855

Met Ser Ala Asn Pro Ser Lys Val Ser Tyr Glu Pro Ile Thr Thr Thr
              1860                1865                1870

Leu Lys Arg Lys Gln Glu Asp Val Ser Ala Thr Val Ile Gln Arg Ala
              1875                1880                1885

Tyr Arg Arg Tyr Arg Leu Arg Gln Asn Val Lys Asn Ile Ser Ser Ile
              1890                1895                1900

Tyr Ile Lys Asp Gly Asp Arg Asp Asp Leu Leu Asn Lys Lys Asp
1905                1910                1915                1920

Met Ala Phe Asp Asn Val Asn Glu Asn Ser Ser Pro Glu Lys Thr Asp
              1925                1930                1935

Ala Thr Ser Ser Thr Thr Ser Pro Pro Ser Tyr Asp Ser Val Thr Lys
              1940                1945                1950

Pro Asp Lys Glu Lys Tyr Glu Gln Asp Arg Thr Glu Lys Glu Asp Lys
              1955                1960                1965

Gly Lys Asp Ser Lys Glu Ser Lys Lys
              1970                1975
```